US012790311B2

(12) United States Patent
Bhuniya et al.

(10) Patent No.: US 12,790,311 B2
(45) Date of Patent: Nov. 10, 2026

(54) COMPOUNDS USEFUL AS POLY(ADP-RIBOSE) POLYMERASE (PARP) INHIBITORS

(71) Applicant: RHIZEN PHARMACEUTICALS AG, Basel (CH)

(72) Inventors: Debnath Bhuniya, Shameerpet (IN); Srikant Viswanadha, Shameerpet (IN); Gayatri Swaroop Merikapudi, Shameerpet (IN); Swaroop Kumar Venkata Satya Vakkalanka, Basel (CH)

(73) Assignee: RHIZEN PHARMACEUTICALS AG, Basel (CH)

( * ) Notice: Subject to any disclaimer, the term of this patent is extended or adjusted under 35 U.S.C. 154(b) by 878 days.

(21) Appl. No.: 17/996,030

(22) PCT Filed: Apr. 23, 2021

(86) PCT No.: PCT/IB2021/053382

§ 371 (c)(1),
(2) Date: Oct. 12, 2022

(87) PCT Pub. No.: WO2021/220120

PCT Pub. Date: Nov. 4, 2021

(65) Prior Publication Data

US 2023/0234938 A1 Jul. 27, 2023

(30) Foreign Application Priority Data

Apr. 28, 2020 (IN) ............................ 202041018149
Nov. 2, 2020 (IN) ............................ 202041047713

(51) Int. Cl.
*C07D 401/14* (2006.01)
*C07D 401/10* (2006.01)
*C07D 411/04* (2006.01)
*C07D 471/04* (2006.01)

(52) U.S. Cl.
CPC ......... *C07D 401/14* (2013.01); *C07D 401/10* (2013.01); *C07D 471/04* (2013.01)

(58) Field of Classification Search
CPC .. C07D 401/10; C07D 401/14; C07D 471/04; C07D 403/10; A61P 35/00; A61K 31/502
See application file for complete search history.

(56) References Cited

U.S. PATENT DOCUMENTS 7,470,688 B2 12/2008 Javaid et al.

FOREIGN PATENT DOCUMENTS

| | | | | |
|---|---|---|---|---|
| CN | 106458993 | A | 2/2017 | |
| IN | 201848001910 | A | 1/2018 | |
| WO | 0042040 | A1 | 7/2000 | |
| WO | 0116136 | A2 | 3/2001 | |
| WO | 0236576 | A1 | 5/2002 | |
| WO | 02090334 | A1 | 11/2002 | |
| WO | 03093261 | A1 | 11/2003 | |
| WO | 03106430 | A1 | 12/2003 | |
| WO | 2004080976 | A1 | 9/2004 | |
| WO | 2004087713 | A1 | 10/2004 | |
| WO | 2005012305 | A2 | 2/2005 | |
| WO | 2005012524 | A1 | 2/2005 | |
| WO | 2005053662 | A1 | 6/2005 | |
| WO | 2006021801 | A1 | 3/2006 | |
| WO | 2006033003 | A1 | 3/2006 | |
| WO | 2006033006 | A2 | 3/2006 | |
| WO | 2006033007 | A2 | 3/2006 | |
| WO | 2006067472 | A1 | 6/2006 | |
| WO | 2007144637 | A1 | 12/2007 | |
| WO | 2007144639 | A1 | 12/2007 | |
| WO | 2007144652 | A2 | 12/2007 | |
| WO | 2008047082 | A2 | 4/2008 | |
| WO | 2008114114 | A2 | 9/2008 | |
| WO | WO-2008114023 | A2 * | 9/2008 | ........... C07D 417/14 |
| WO | 2009050469 | A1 | 4/2009 | |
| WO | 2011098971 | A1 | 8/2011 | |
| WO | 2014036022 | A1 | 3/2014 | |
| WO | 2015108986 | A1 | 7/2015 | |
| WO | 2016028689 | A1 | 2/2016 | |
| WO | 2016165650 | A1 | 10/2016 | |
| WO | 2017123156 | A1 | 7/2017 | |
| WO | 2017140283 | A1 | 8/2017 | |
| WO | 2017153958 | A1 | 9/2017 | |
| WO | 2017191562 | A1 | 11/2017 | |
| WO | 2018038680 | A1 | 3/2018 | |

(Continued)

OTHER PUBLICATIONS

"Bioisosterism: A Rational Approach in Drug Design" GS Patani, EJ LaVoie. Chem Rev Dec. 19, 1996 ;96(8):3147-3176. doi: 10.1021/cr950066q. (Year: 1996).*

(Continued)

*Primary Examiner* — Kara R. Mcmillian
*Assistant Examiner* — Sophia P Hirakis
(74) *Attorney, Agent, or Firm* — Blank Rome LLP

(57) ABSTRACT

The present invention provides novel poly(ADP-ribose) polymerase (PARP) inhibitors, methods of preparing them, pharmaceutical compositions containing them and methods for the treatment, prevention and/or amelioration of PARP mediated diseases or disorders using them. In particular, the compounds described herein are useful for the treatment of carcinoma of the breast, ovarian cancer, carcinoma of the liver, carcinoma of the lung, small cell lung cancer, esophageal cancer, gall bladder cancer, pancreatic cancer and stomach cancer.

28 Claims, No Drawings

(56) References Cited

FOREIGN PATENT DOCUMENTS

| | | | |
|---|---|---|---|
| WO | 2018108152 | A1 | 6/2018 |
| WO | 2018197463 | A1 | 11/2018 |

OTHER PUBLICATIONS

Loh, Vincent M. Jr, et al., "Phthalazinones. Part 1: The design and synthesis of a novel series of potent inhibitors of poly(ADP-ribose)polymerase", Bioorganic & Medicinal Chemistry Letters, 2005, 15:2235-2238.

* cited by examiner

COMPOUNDS USEFUL AS POLY(ADP-RIBOSE) POLYMERASE (PARP) INHIBITORS

This application is the U.S. national phase of International Patent Application No. PCT/IB2021/053382, filed Apr. 23, 2021, which claims the benefit of Indian patents application Nos. 202041018149, filed Apr. 28, 2020, and 202041047713, filed Nov. 2, 2020, the entire contents of each of which are hereby incorporated by reference.

FIELD OF THE INVENTION

The present invention relates to compounds useful as poly(ADP-ribose) polymerase (PARP) inhibitors, to methods of preparing them, pharmaceutical compositions containing them, and to methods for the treatment, prevention and/or amelioration of diseases or disorders involving PARP.

BACKGROUND OF THE INVENTION

Poly(ADP-ribose) polymerase (PARP) defines a family of 17 enzymes that cleaves NAD+ to nicotinamide and ADP-ribose to form long and branched (ADP-ribose) polymers on glutamic acid residues of a number of target proteins, including PARP itself. The addition of negatively charged polymers profoundly alters the properties and functions of the acceptor proteins. Poly(ADP-ribosyl)ation is involved in the regulation of many cellular processes, such as DNA repair, gene transcription, cell cycle progression, cell death, chromatin functions and genomic stability. These functions have been mainly attributed to PARP-1 that is regarded as the best characterized member of the PARP family. However, the identification of novel genes encoding PARPs, together with the characterization of their structure and subcellular localization, have disclosed different roles for poly(ADP-ribosyl)ation in cells, including telomere replication and cellular transport.

Recently, poly(ADP-ribose) binding sites have been identified in many DNA damage checkpoint proteins, such as tumor suppressor p53, cyclin-dependent kinase inhibitor p21Cip1/Waf1, DNA damage recognition factors (i.e., the nucleotide excision repair xeroderma pigmentosum group A complementing protein and the mismatch repair protein MSH6), base excision repair (BER) proteins (i.e. DNA ligase III, X-ray repair cross-complementing 1, and XRCC1), DNA-dependent protein kinase (DNA-PK), cell death and survival regulators (i.e., NF-kB, inducible nitric oxide synthase, and telomerase). These findings suggest that the different components of the PARP family might be involved in the DNA damage signal network, thus regulating protein-protein and protein-DNA interactions and, consequently, different types of cellular responses to genotoxic stress. In addition to its involvement in BER and single strand breaks (SSB) repair, PARP-1 appears to aid in the non-homologous end-joining (NHEJ) and homologous recombination (HR) pathways of double strand breaks (DSB) repair. See Lucio Tentori et al., *Pharmacological Research*, Vol. 45, No. 2, 2002, page 73-85.

PARP inhibition might be a useful therapeutic strategy not only for the treatment of BRCA mutations but also for the treatment of a wider range of tumors bearing a variety of deficiencies in the HR pathway. Further, the existing clinical data (e.g., Csaba Szabo et al., *British Journal of Pharmacology* (2018) 175:192-222) also indicate that stroke, traumatic brain injury, circulatory shock and acute myocardial infarction are some of the indications where PARP activation has been demonstrated to contribute to tissue necrosis and inflammatory responses.

As of now, four PARP inhibitors, namely olaparib, talazoparib, niraparib, and rucaparib have been approved for human use by regulatory authorities around the world.

Patent literature related to PARP inhibitors includes International Publication Nos. WO 2000/42040, WO 2001/016136, WO 2002/036576, WO 2002/090334, WO2003/093261, WO 2003/106430, WO 2004/080976, WO 2004/087713, WO 2005/012305, WO 2005/012524, WO 2005/012305, WO 2005/012524, WO 2005/053662, WO2006/033003, WO2006/033007, WO 2006/033006, WO 2006/021801, WO 2006/067472, WO 2007/144637, WO 2007/144639, WO 2007/144652, WO 2008/047082, WO 2008/114114, WO 2009/050469, WO 2011/098971, WO 2015/108986, WO 2016/028689, WO 2016/165650, WO 2017/153958, WO 2017/191562, WO 2017/123156, WO 2017/140283, WO 2018/197463, WO 2018/038680 and WO 2018/108152, each of which is incorporated herein by reference in its entirety for all purposes.

There still remains an unmet need for new PARP inhibitors for the treatment of various diseases and disorders associated with cell proliferation, such as cancer.

SUMMARY OF THE INVENTION

The present invention relates to compounds of formula (I) and pharmaceutically acceptable salts thereof, pharmaceutical compositions containing them, methods for their preparation, and methods of treatment with them. In particular, the compounds of formula (I) and pharmaceutically acceptable salts thereof are useful in the treatment, prevention and/or amelioration of diseases or disorders involving PARP.

In one aspect, the present invention relates to a compound of formula (I):

(I)

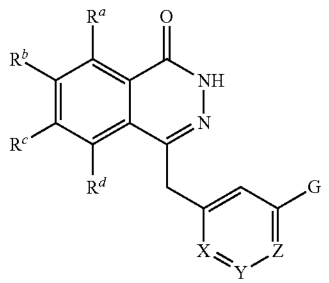

or a tautomer thereof, prodrug thereof, N-oxide thereof, stereoisomer thereof, pharmaceutically acceptable ester thereof or pharmaceutically acceptable salt thereof, wherein $R^a$, $R^b$, $R^c$ and $R^d$ are each independently selected from hydrogen, halogen, and substituted or unsubstituted $C_{1-3}$ alkyl (e.g., $C_{1-3}$ haloalkyl);

X is $CR^x$ or N;

Y is $CR^y$ or N;

Z is $CR^z$ or N;

$R^x$, $R^y$ and $R^z$ may be the same or different and are each independently selected from hydrogen, halogen, and substituted or unsubstituted alkyl;

G is selected from (a)

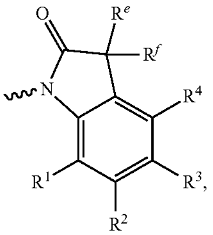

(b)

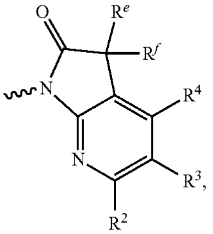

(c)

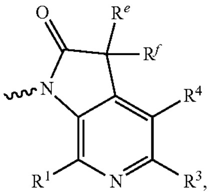

(d)

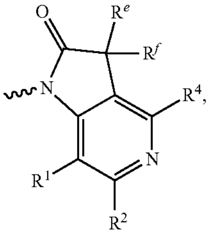

and (e)

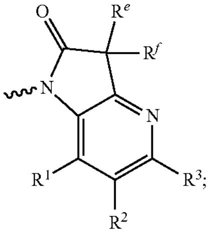

wherein $R^e$ and $R^f$ are the same or different and are each independently selected from hydrogen, halogen, hydroxy, substituted or unsubstituted alkyl (e.g., haloalkyl), substituted or unsubstituted alkoxy, and —$OR^g$, or both $R^e$ and $R^f$ directly bound to a common atom, may be joined to form a $C_{3-6}$ cycloalkyl or heterocyclic ring (e.g., a 3- to 7-member heterocyclic ring);

$R^g$ is selected from hydrogen, substituted or unsubstituted $C_{1-3}$ alkyl, and —(CO)$R^h$;

$R^h$ is selected from hydrogen and substituted or unsubstituted alkyl; and $R^1$, $R^2$, $R^3$ and $R^4$ are each independently selected from hydrogen, halogen, and substituted or unsubstituted alkyl (e.g., haloalkyl).

In another aspect, the present invention relates to a compound of formula (I):

(I)

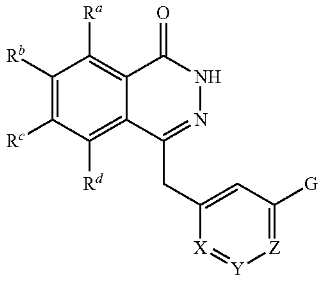

or a tautomer thereof, prodrug thereof, N-oxide thereof, stereoisomer thereof, pharmaceutically acceptable ester thereof or pharmaceutically acceptable salt thereof, wherein $R^a$, $R^b$, $R^c$ and $R^d$ are each independently selected from hydrogen, halogen, and substituted or unsubstituted $C_{1-3}$ alkyl;

X is $CR^x$ or N;

Y is $CR^y$ or N;

Z is $CR^z$ or N;

$R^x$, $R^y$ and $R^2$ may be the same or different and are each independently selected from hydrogen, halogen and substituted or unsubstituted $C_{1-3}$ alkyl; G is selected from (a1)

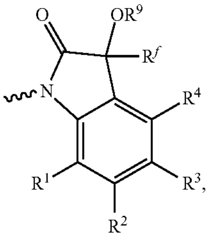

(b1)

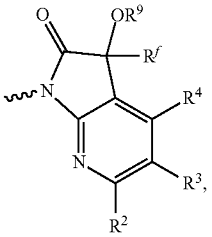

(c1)

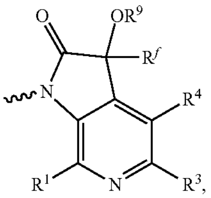

-continued (d1)

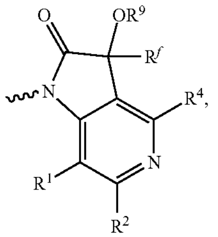

(e1)

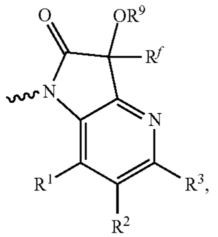

(a2)

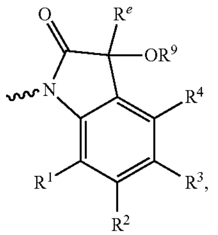

(b2)

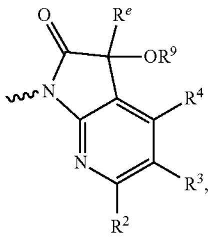

(c2)

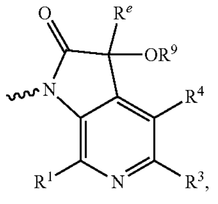

(d2)

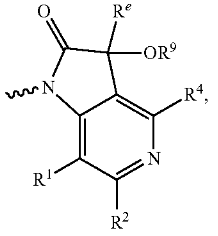

-continued (e2)

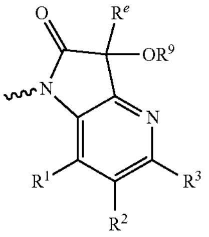

wherein $R^e$ and $R^f$ may be same or different and are each independently selected from hydrogen, halogen, hydroxy, substituted or unsubstituted $C_{1-3}$ alkyl (e.g., $C_{1-3}$ haloalkyl), substituted or unsubstituted $C_{1-3}$ alkoxy and —O (CO)$R^h$; $R^g$ is selected from hydrogen, substituted or unsubstituted $C_{1-3}$ alkyl, and —(CO)$R^h$; $R^h$ is selected from hydrogen and substituted or unsubstituted alkyl; and $R^1$, $R^2$, $R^3$ and $R^4$ are each independently selected from hydrogen, halogen, and substituted or unsubstituted $C_{1-3}$ alkyl (e.g., $C_{1-3}$ haloalkyl).

In another aspect, the present invention relates to a compound of formula (IA) or (IB):

(IA)

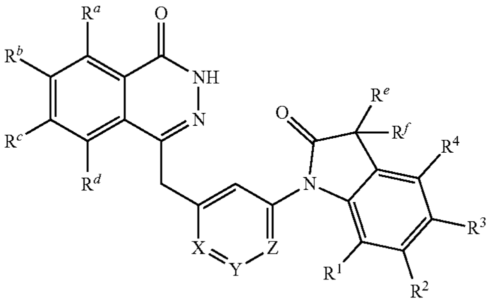

(IB)

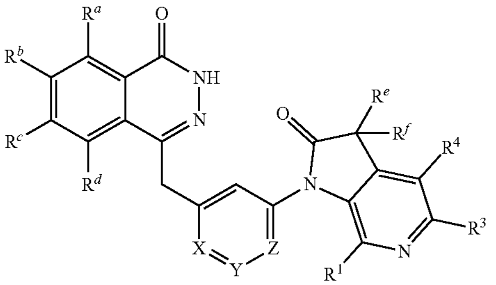

or a tautomer thereof, prodrug thereof, N-oxide thereof, stereoisomer thereof, pharmaceutically acceptable ester thereof or pharmaceutically acceptable salt thereof, wherein variables $R^a$, $R^b$, $R^c$, $R^d$, X, Y, Z, $R^e$, $R^f$, $R^1$, $R^2$, $R^3$ and $R^4$ are as defined above in relation to the compound of formula (I).

One particular embodiment is a compound of formula (I), (IA) or (IB), wherein any one or more of $R^a$, $R^b$, $R^c$ and $R^d$ is halogen.

Another embodiment is a compound of formula (I), (IA) or (IB), wherein any one or more of $R^a$, $R^b$, $R^c$ and $R^d$ is hydrogen.

Another embodiment is a compound of formula (I), (IA) or (IB), wherein $R^a$, $R^c$ and Rd are hydrogen and $R^b$ is halogen.

Another embodiment is a compound of formula (I), (IA) or (IB), wherein $R^b$ is fluorine or chlorine.

Another embodiment is a compound of formula (I), (IA) or (IB), wherein $R^a$, $R^b$ and Rd are hydrogen and $R^e$ is halogen.

Another embodiment is a compound of formula (I), (IA) or (IB), wherein $R^c$ is fluorine or chlorine.

Another embodiment is a compound of formula (I), (IA) or (IB), wherein X, Y and Z are each independently CH or N.

Another embodiment is a compound of formula (I), (IA) or (IB), wherein X is CH or

N.

Another embodiment is a compound of formula (I), (IA) or (IB), wherein Y is CH or N.

Another embodiment is a compound of formula (I), (IA) or (IB), wherein Z is CH or N.

Another embodiment is a compound of formula (I), (IA) or (IB), wherein X is N.

Another embodiment is a compound of formula (I), (IA) or (IB), wherein Y is N.

Another embodiment is a compound of formula (I), (IA) or (IB), wherein Z is N.

Another embodiment is a compound of formula (I), (IA) or (IB), wherein Y and Z are CH and X is N.

Another embodiment is a compound of formula (I), (IA) or (IB), wherein X and Z are CH and Y is N.

Another embodiment is a compound of formula (I), (IA) or (IB), wherein X and Y are CH and Z is N.

Another embodiment is a compound of formula (I), (IA) or (IB), wherein and Y is CH and Z is $CR^z$ (where $R^z$ is defined as above).

Another embodiment is a compound of formula (I), (IA) or (IB), wherein X and Y are CH and Z is $CR^z$ wherein $R^z$ is halogen.

Another embodiment is a compound of formula (I), (IA) or (IB), wherein X and Y are CH and Z is $CR^z$ wherein $R^z$ is fluorine.

Another embodiment is a compound of formula (I), (IA) or (IB), wherein Z is CH;

Another embodiment is a compound of formula (I), (IA) or (IB), wherein X, Y and Z are CH.

Another embodiment is a compound of formula (I), (IA) or (IB), wherein $R^e$ and Rf are each independently selected from hydrogen, hydroxy, substituted or unsubstituted $C_{1-3}$ alkyl (e.g., $C_{1-3}$ haloalkyl), substituted or unsubstituted $C_{1-3}$ alkoxy and acetyloxy.

Another embodiment is a compound of formula (I), (IA) or (IB), wherein $R^e$ is hydroxy, substituted or unsubstituted $C_{1-3}$ alkoxy or acetyloxy.

Another embodiment is a compound of formula (I), (IA) or (IB), wherein $R^e$ is hydroxy.

Another embodiment is a compound of formula (I), (IA) or (IB), wherein $R^f$ is substituted or unsubstituted $C_{1-3}$ alkyl (e.g., $C_{1-3}$ haloalkyl).

Another embodiment is a compound of formula (I), (IA) or (IB), wherein $R^f$ is substituted or unsubstituted $C_{1-3}$ alkyl.

Another embodiment is a compound of formula (I), (IA) or (IB), wherein $R^e$ is hydroxy and $R^f$ is substituted or unsubstituted $C_{1-3}$ alkyl.

Another embodiment is a compound of formula (I), (IA) or (IB), wherein (i)$R^e$ and $R^f$ are both hydrogen;

(ii)$R^e$ and $R^f$ are each independently selected from substituted or unsubstituted $C_1$-3 alkyl; or (iii) both $R^e$ and $R^f$ directly bound to a common atom, are joined to form an $C_{3-6}$ cycloalkyl or heterocyclic ring (e.g., a 3- to 7-member heterocyclic ring).

Another embodiment is a compound of formula (I), (IA) or (IB), wherein (i)$R^1$, $R^2$, $R^3$ and $R^4$ are independently selected from hydrogen or halogen;

(ii)$R^1$, $R^2$, $R^3$ and $R^4$ are hydrogen;

(iii)$R^1$, $R^2$, $R^3$ and $R^4$ are halogen;

(iv)$R^1$, $R^3$ and $R^4$ are hydrogen and $R^2$ is halogen; or (v)$R^1$, $R^2$ and $R^4$ are hydrogen and $R^3$ is halogen.

Another embodiment is a compound of formula (I), (IA) or (IB), wherein (i) any one or more of $R^1$, $R^2$, $R^3$ and $R^4$ is fluorine or chlorine;

(ii)$R^1$, $R^3$ and $R^4$ are hydrogen and $R^2$ is fluorine; or (iii)$R^1$, $R^2$ and $R^4$ are hydrogen and $R^3$ is fluorine.

Another embodiment is a compound of formula (I), (IA) or (IB), wherein $R^e$ and $R^f$ are hydrogen.

Another embodiment is a compound of formula (I), (IA) or (IB), wherein $R^e$ and $R^f$ are methyl.

Another embodiment is a compound of formula (I), (IA) or (IB), wherein both $R^e$ and $R^f$ directly bound to a common atom are joined to form a $C_{3-6}$ cycloalkyl ring or heterocyclic ring (e.g., a 3- to 7-member heterocyclic ring).

Another embodiment is a compound of formula (I), (IA) or (IB), wherein any one or more of $R^1$, $R^2$, $R^3$ and $R^4$ is selected from hydrogen and halogen.

Another embodiment is a compound of formula (I), (IA) or (IB), wherein any one or more of $R^1$, $R^2$, $R^3$ and $R^4$ is hydrogen.

Another embodiment is a compound of formula (I), (IA) or (IB), wherein any one or more of $R^1$, $R^2$, $R^3$ and $R^4$ is halogen.

Another embodiment is a compound of formula (I), (IA) or (IB), wherein any one or more of $R^1$, $R^2$, $R^3$ and $R^4$ is fluorine or chlorine.

Another embodiment is a compound of formula (I), (IA) or (IB), wherein $R^1$, $R^3$ and $R^4$ are hydrogen and $R^2$ is halogen.

Another embodiment is a compound of formula (I), (IA) or (IB), wherein $R^1$, $R^3$ and $R^4$ are hydrogen and $R^2$ is fluorine.

Another embodiment is a compound of formula (I), (IA) or (IB), wherein $R^1$, $R^2$ and $R^4$ are hydrogen and $R^3$ is halogen.

Another embodiment is a compound of formula (I), (IA) or (IB), wherein $R^1$, $R^2$ and $R^4$ are hydrogen and $R^3$ is fluorine.

Another embodiment is a compound of formula (I), wherein G is selected from

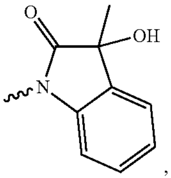 ,
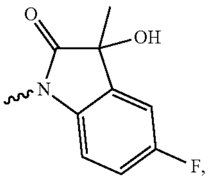 ,
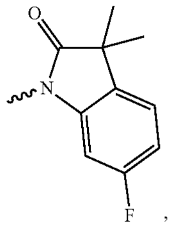 ,
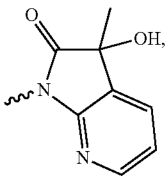 ,
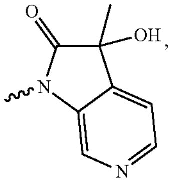 ,
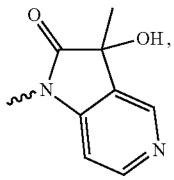 ,

-continued

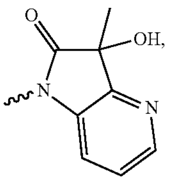
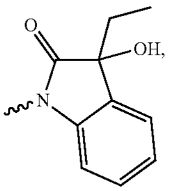
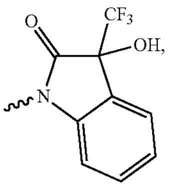

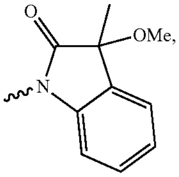
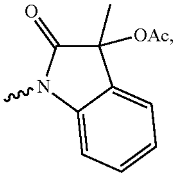
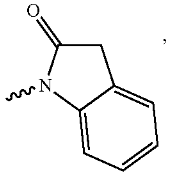
,

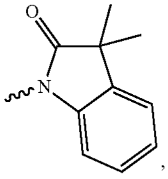
,
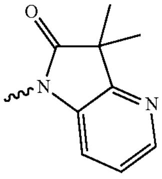
and

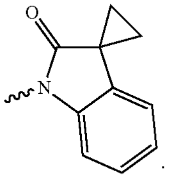

Another embodiment is a compound of formula (I), wherein G is selected from

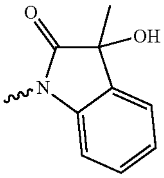
,
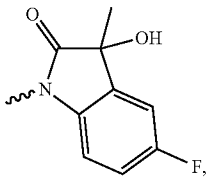
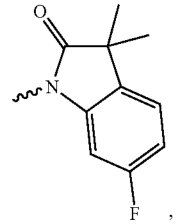
,

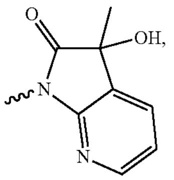
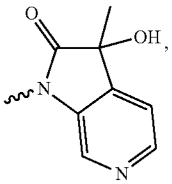
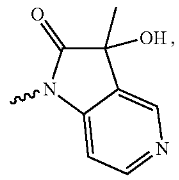

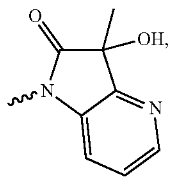
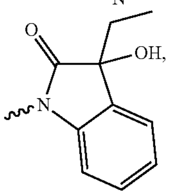
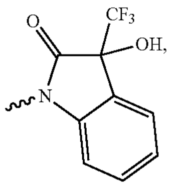

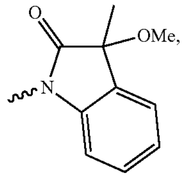
or
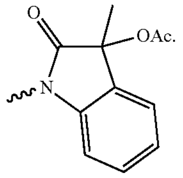

Representative compounds of the present invention include those specified below and pharmaceutically acceptable salts thereof. The present invention should not be construed to be limited to these specific compounds.

In one embodiment, the present invention relates to a compound selected from:

1. 4-((5-(3-Hydroxy-3-methyl-2-oxoindolin-1-yl)pyridin-3-yl)methyl)phthalazin-1(2H)-one;
2. (R)-(+)-4-((5-(3-Hydroxy-3-methyl-2-oxoindolin-1-yl)pyridin-3-yl)methyl)phthalazin-1(2H)-one;
3. (S)-(−)-4-((5-(3-Hydroxy-3-methyl-2-oxoindolin-1-yl)pyridin-3-yl)methyl)phthalazin-1(2H)-one;
4. 4-(4-Fluoro-3-(3-hydroxy-3-methyl-2-oxoindolin-1-yl)benzyl)phthalazin-1(2H)-one;
5. 4-((5-(3-Ethyl-3-hydroxy-2-oxoindolin-1-yl)pyridin-3-yl)methyl)phthalazin-1(2H)-one;
6. 7-Fluoro-4-((5-(3-hydroxy-3-methyl-2-oxoindolin-1-yl)pyridin-3-yl)methyl)phthalazin-1(2H)-one;
7. (+)-7-Fluoro-4-((5-(3-hydroxy-3-methyl-2-oxoindolin-1-yl)pyridin-3-yl)methyl)phthalazin-1(2H)-one;
8. (−)-7-Fluoro-4-((5-(3-hydroxy-3-methyl-2-oxoindolin-1-yl)pyridin-3-yl)methyl)phthalazin-1(2H)-one;
9. 6-Fluoro-4-((5-(3-hydroxy-3-methyl-2-oxoindolin-1-yl)pyridin-3-yl)methyl)phthalazin-1(2H)-one;
10. 7-Fluoro-4-((5-(5-fluoro-3-hydroxy-3-methyl-2-oxoindolin-1-yl)pyridin-3-yl)methyl)phthalazin-1(2H)-one;
11. (+)-7-Fluoro-4-((5-(5-fluoro-3-hydroxy-3-methyl-2-oxoindolin-1-yl)pyridin-3-yl)methyl)phthalazin-1(2H)-one;
12. (−)-7-Fluoro-4-((5-(5-fluoro-3-hydroxy-3-methyl-2-oxoindolin-1-yl)pyridin-3-yl)methyl)phthalazin-1(2H)-one;
13. 4-((5-(5-Fluoro-3-hydroxy-3-methyl-2-oxoindolin-1-yl)pyridin-3-yl)methyl)phthalazin-1(2H)-one;
14. (+)-4-((5-(5-Fluoro-3-hydroxy-3-methyl-2-oxoindolin-1-yl)pyridin-3-yl)methyl)phthalazin-1(2H)-one;
15. (−)-4-((5-(5-Fluoro-3-hydroxy-3-methyl-2-oxoindolin-1-yl)pyridin-3-yl)methyl)phthalazin-1(2H)-one;
16. 7-Fluoro-4-((5-(6-fluoro-3-hydroxy-3-methyl-2-oxoindolin-1-yl)pyridin-3-yl)methyl)phthalazin-1(2H)-one;
17. 7-Fluoro-4-((5-(6-fluoro-3-hydroxy-3-methyl-2-oxoindolin-1-yl)pyridin-3-yl)methyl)phthalazin-1(2H)-one;
18. 4-((2-(3-hydroxy-3-methyl-2-oxoindolin-1-yl)pyridin-4-yl)methyl)phthalazin-1(2H)-one;
19. (−)-4-((2-(3-Hydroxy-3-methyl-2-oxoindolin-1-yl)pyridin-4-yl)methyl)phthalazin-1(2H)-one;
20. (+)-4-((2-(3-Hydroxy-3-methyl-2-oxoindolin-1-yl)pyridin-4-yl)methyl)phthalazin-1(2H)-one;
21. 7-Fluoro-4-((2-(3-hydroxy-3-methyl-2-oxoindolin-1-yl)pyridin-4-yl)methyl)phthalazin-1(2H)-one;
22. (−)-7-Fluoro-4-((2-(3-hydroxy-3-methyl-2-oxoindolin-1-yl)pyridin-4-yl)methyl)phthalazin-1(2H)-one;
23. (+)-7-Fluoro-4-((2-(3-hydroxy-3-methyl-2-oxoindolin-1-yl)pyridin-4-yl)methyl)phthalazin-1(2H)-one;
24. 7-Fluoro-4-((2-(5-fluoro-3-hydroxy-3-methyl-2-oxoindolin-1-yl)pyridin-4-yl)methyl)phthalazin-1(2H)-one;
25. 4-((5-(3-Hydroxy-2-oxo-3-(trifluoromethyl)indolin-1-yl)pyridin-3-yl)methyl)phthalazin-1(2H)-one;
26. (+)-4-((5-(3-Hydroxy-2-oxo-3-(trifluoromethyl)indolin-1-yl)pyridin-3-yl)methyl)phthalazin-1(2H)-one;
27. (−)-4-((5-(3-Hydroxy-2-oxo-3-(trifluoromethyl)indolin-1-yl)pyridin-3-yl)methyl)phthalazin-1(2H)-one;
28. 4-(3-(3-Hydroxy-3-methyl-2-oxoindolin-1-yl)benzyl)phthalazin-1(2H)-one;

29. 7-Fluoro-4-(4-fluoro-3-(3-hydroxy-3-methyl-2-oxoindolin-1-yl)benzyl)phthalazin-1(2H)-one;
30. 4-((5-(3-methoxy-3-methyl-2-oxoindolin-1-yl)pyridin-3-yl)methyl)phthalazin-1(2H)-one;
31. 4-(3-(3-Hydroxy-3-methyl-2-oxo-2,3-dihydro-1H-pyrrolo[2,3-c]pyridin-1-yl)benzyl)phthalazin-1(2H)-one;
32. 3-Methyl-2-oxo-1-(5-((4-oxo-3,4-dihydrophthalazin-1-yl)methyl)pyridin-3-yl)indolin-3-yl acetate;
33. 4-(4-Fluoro-3-(2-oxoindolin-1-yl)benzyl)phthalazin-1(2H)-one;
34. 4-(3-(3,3-Dimethyl-2-oxoindolin-1-yl)-4-fluorobenzyl)phthalazine-1(2H)-one;
35. 4-((5-(3,3-Dimethyl-2-oxoindolin-1-yl)pyridin-3-yl)methyl)phthalazin-1(2H)-one;
36. 4-((5-(3,3-Dimethyl-2-oxo-2,3-dihydro-1H-pyrrolo[3,2-b]pyridin-1-yl)pyridin-3-yl)methyl)phthalazin-1(2H)-one;
37. 4-(3-(3,3-Dimethyl-2-oxo-2,3-dihydro-1H-pyrrolo[3,2-b]pyridin-1-yl)-4-fluorobenzyl)phthalazin-1(2H)-one;
38. 1'-(5-((4-Oxo-3,4-dihydrophthalazin-1-yl)methyl)pyridin-3-yl)spiro[cyclopropane-1,3'-indolin]-2'-one;

and pharmaceutically acceptable salts thereof.

TABLE 1

| Ex. No. | Structure |
|---|---|
| 1 | 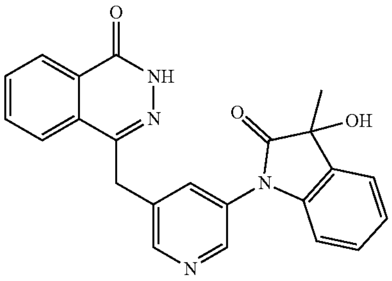 [SMILES: CC1(O)C(=O)N(c2cncc(Cc3n[nH]c(=O)c4ccccc34)c2)c2ccccc21] |
| 2 | 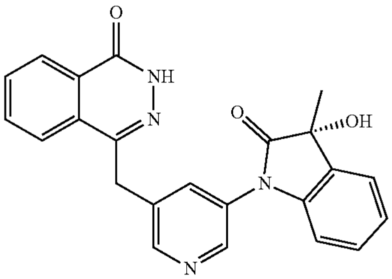 [SMILES: C[C@]1(O)C(=O)N(c2cncc(Cc3n[nH]c(=O)c4ccccc34)c2)c2ccccc21] |
| 3 | 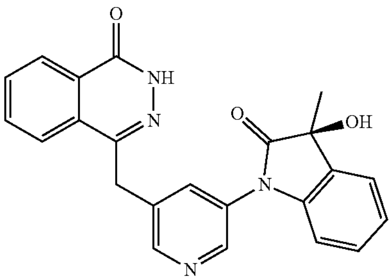 [SMILES: C[C@@]1(O)C(=O)N(c2cncc(Cc3n[nH]c(=O)c4ccccc34)c2)c2ccccc21] |

TABLE 1-continued

| Ex. No. | Structure |
|---|---|
| 4 | 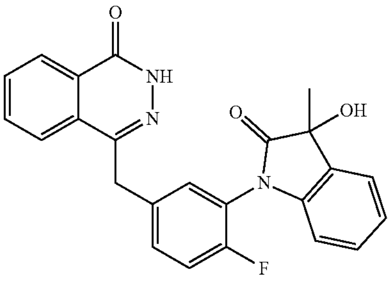 [SMILES: CC1(O)C(=O)N(c2cc(Cc3n[nH]c(=O)c4ccccc34)ccc2F)c2ccccc21] |
| 5 | 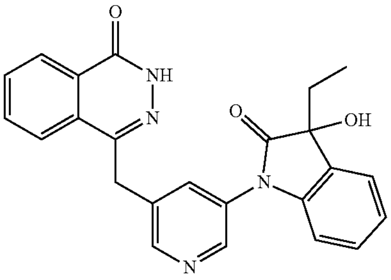 [SMILES: CCC1(O)C(=O)N(c2cncc(Cc3n[nH]c(=O)c4ccccc34)c2)c2ccccc21] |
| 6 | 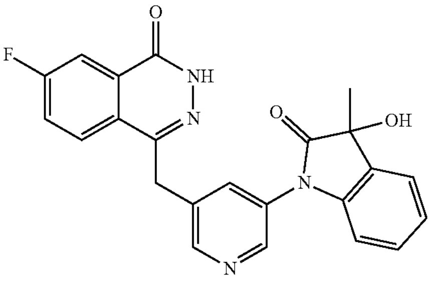 [SMILES: CC1(O)C(=O)N(c2cncc(Cc3n[nH]c(=O)c4cc(F)ccc34)c2)c2ccccc21] |
| 7 | 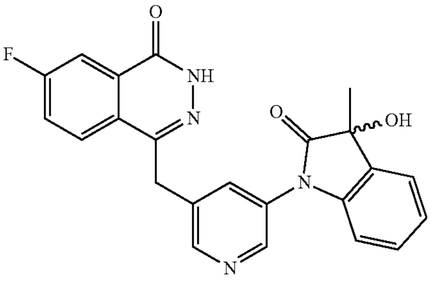 [SMILES: CC1(O)C(=O)N(c2cncc(Cc3n[nH]c(=O)c4cc(F)ccc34)c2)c2ccccc21] |
| 8 | 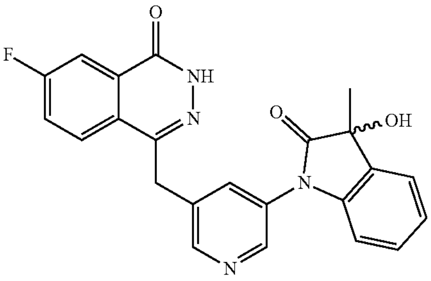 [SMILES: CC1(O)C(=O)N(c2cncc(Cc3n[nH]c(=O)c4cc(F)ccc34)c2)c2ccccc21] |

TABLE 1-continued
| Ex. No. | Structure |
|---|---|
| 9 | 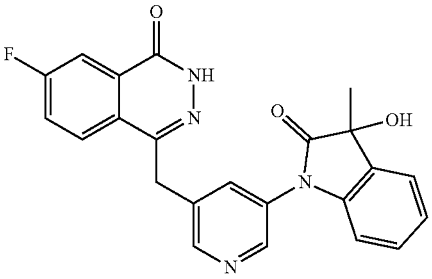 [SMILES: CC1(O)C(=O)N(c2cncc(Cc3n[nH]c(=O)c4cc(F)ccc34)c2)c2ccccc21] |
| 10 | 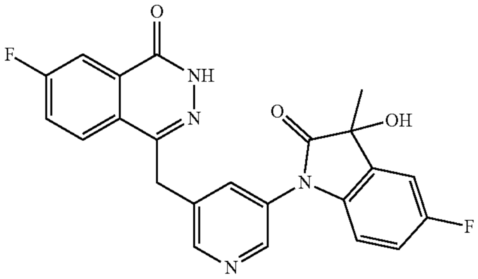 [SMILES: CC1(O)C(=O)N(c2cncc(Cc3n[nH]c(=O)c4cc(F)ccc34)c2)c2ccc(F)cc21] |
| 11 | 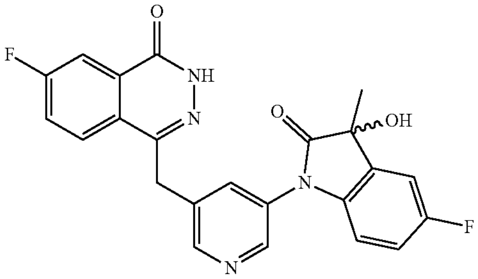 [SMILES: CC1(O)C(=O)N(c2cncc(Cc3n[nH]c(=O)c4cc(F)ccc34)c2)c2ccc(F)cc21] |
| 12 | 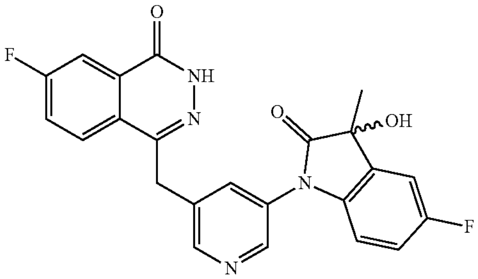 [SMILES: CC1(O)C(=O)N(c2cncc(Cc3n[nH]c(=O)c4cc(F)ccc34)c2)c2ccc(F)cc21] |
| 13 | 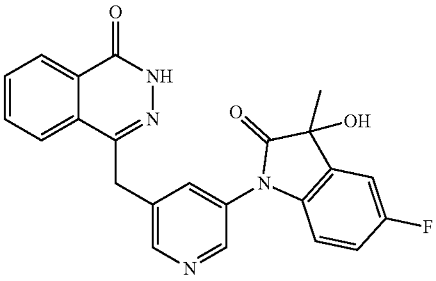 [SMILES: CC1(O)C(=O)N(c2cncc(Cc3n[nH]c(=O)c4ccccc34)c2)c2ccc(F)cc21] |
TABLE 1-continued
| Ex. No. | Structure |
|---|---|
| 14 | 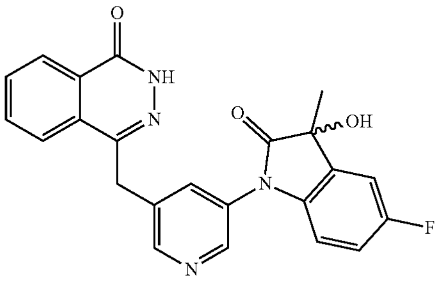 [SMILES: CC1(O)C(=O)N(c2cncc(Cc3n[nH]c(=O)c4ccccc34)c2)c2ccc(F)cc21] |
| 15 | 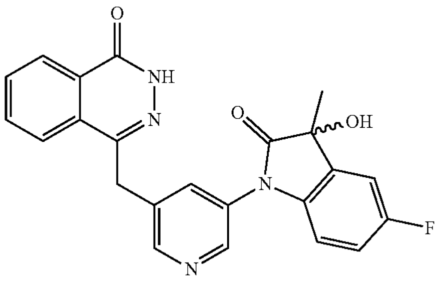 [SMILES: CC1(O)C(=O)N(c2cncc(Cc3n[nH]c(=O)c4ccccc34)c2)c2ccc(F)cc21] |
| 16 | 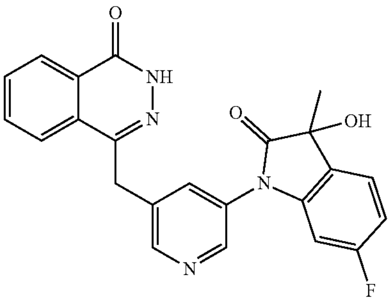 [SMILES: CC1(O)C(=O)N(c2cncc(Cc3n[nH]c(=O)c4ccccc34)c2)c2cc(F)ccc21] |
| 17 | 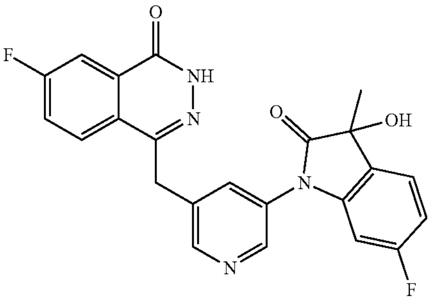 [SMILES: CC1(O)C(=O)N(c2cncc(Cc3n[nH]c(=O)c4cc(F)ccc34)c2)c2cc(F)ccc21] |
| 18 | 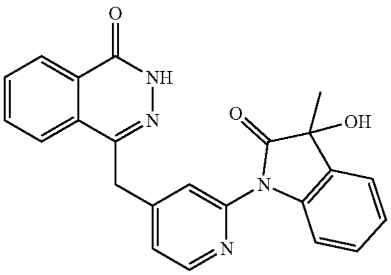 [SMILES: CC1(O)C(=O)N(c2cc(Cc3n[nH]c(=O)c4ccccc34)ccn2)c2ccccc21] |

TABLE 1-continued
| Ex. No. | Structure |
|---|---|
| 19 | 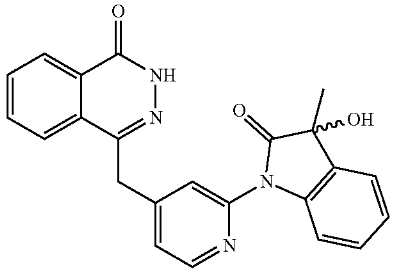 [SMILES: CC1(O)C(=O)N(c2cc(Cc3n[nH]c(=O)c4ccccc34)ccn2)c2ccccc21] |
| 20 | 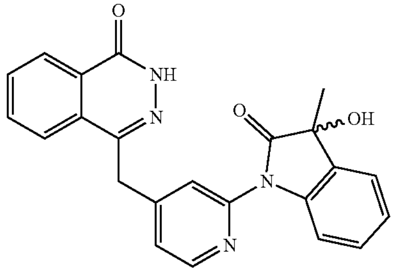 [SMILES: CC1(O)C(=O)N(c2cc(Cc3n[nH]c(=O)c4ccccc34)ccn2)c2ccccc21] |
| 21 | 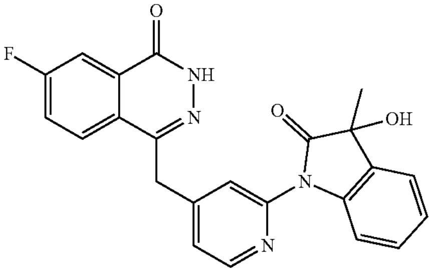 [SMILES: CC1(O)C(=O)N(c2cc(Cc3n[nH]c(=O)c4cc(F)ccc34)ccn2)c2ccccc21] |
| 22 | 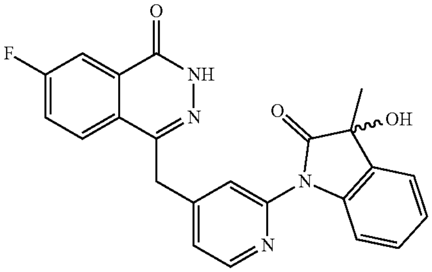 [SMILES: CC1(O)C(=O)N(c2cc(Cc3n[nH]c(=O)c4cc(F)ccc34)ccn2)c2ccccc21] |
| 23 | 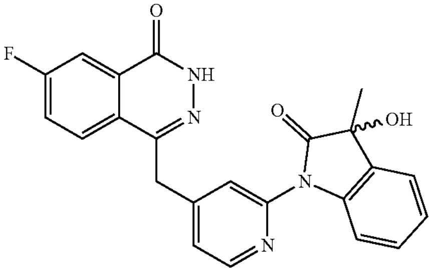 [SMILES: CC1(O)C(=O)N(c2cc(Cc3n[nH]c(=O)c4cc(F)ccc34)ccn2)c2ccccc21] |
TABLE 1-continued
| Ex. No. | Structure |
|---|---|
| 24 | 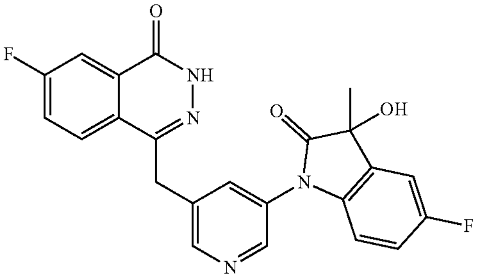 [SMILES: CC1(O)C(=O)N(c2cncc(Cc3n[nH]c(=O)c4cc(F)ccc34)c2)c2ccc(F)cc21] |
| 25 | 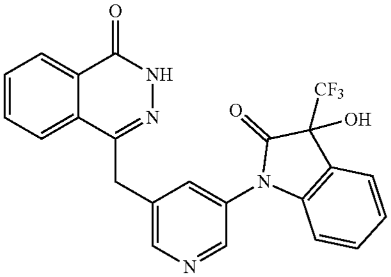 [SMILES: O=C1N(c2cncc(Cc3n[nH]c(=O)c4ccccc34)c2)c2ccccc2C1(O)C(F)(F)F] |
| 26 | 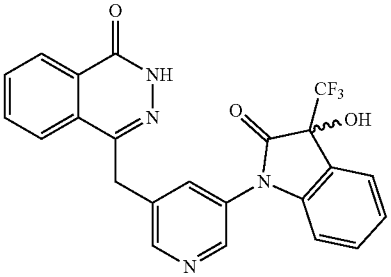 [SMILES: O=C1N(c2cncc(Cc3n[nH]c(=O)c4ccccc34)c2)c2ccccc2C1(O)C(F)(F)F] |
| 27 | 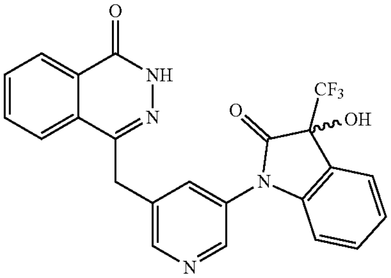 [SMILES: O=C1N(c2cncc(Cc3n[nH]c(=O)c4ccccc34)c2)c2ccccc2C1(O)C(F)(F)F] |
| 28 | 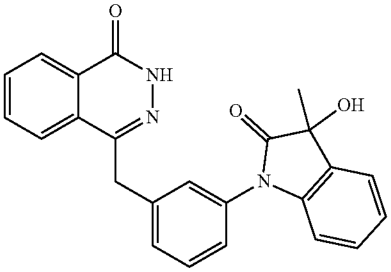 [SMILES: CC1(O)C(=O)N(c2cccc(Cc3n[nH]c(=O)c4ccccc34)c2)c2ccccc21] |

TABLE 1-continued
| Ex. No. | Structure |
|---|---|
| 29 | 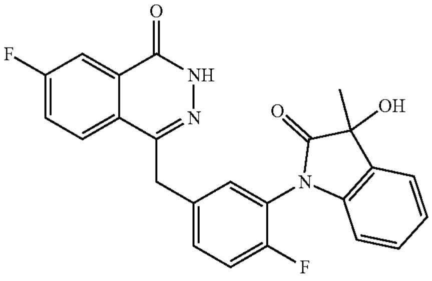 [SMILES: CC1(O)C(=O)N(c2cc(Cc3n[nH]c(=O)c4cc(F)ccc34)ccc2F)c2ccccc21] |
| 30 | 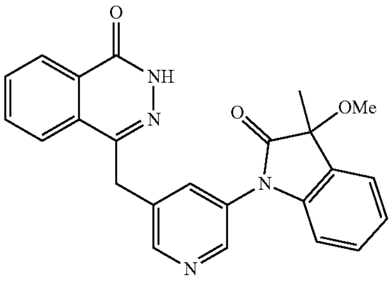 [SMILES: COC1(C)C(=O)N(c2cncc(Cc3n[nH]c(=O)c4ccccc34)c2)c2ccccc21] |
| 31 | 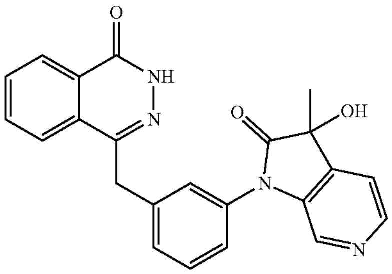 [SMILES: CC1(O)C(=O)N(c2cccc(Cc3n[nH]c(=O)c4ccccc34)c2)c2cnccc21] |
| 32 | 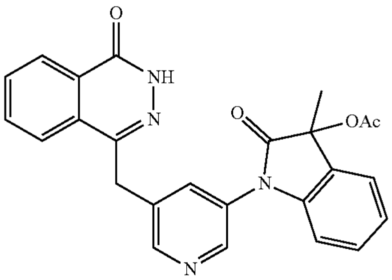 |
| 33 | 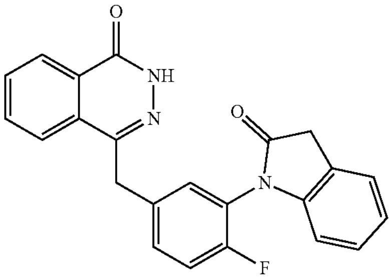 [SMILES: O=C1Cc2ccccc2N1c1cc(Cc2n[nH]c(=O)c3ccccc23)ccc1F] |
| 34 | 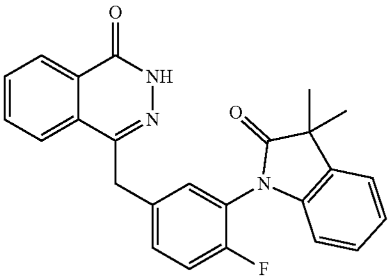 [SMILES: CC1(C)C(=O)N(c2cc(Cc3n[nH]c(=O)c4ccccc34)ccc2F)c2ccccc21] |
| 35 | 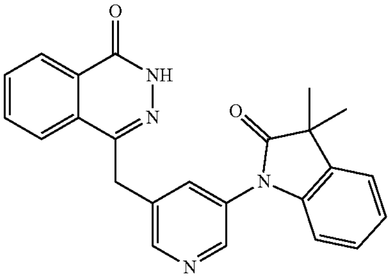 [SMILES: CC1(C)C(=O)N(c2cncc(Cc3n[nH]c(=O)c4ccccc34)c2)c2ccccc21] |
| 36 | 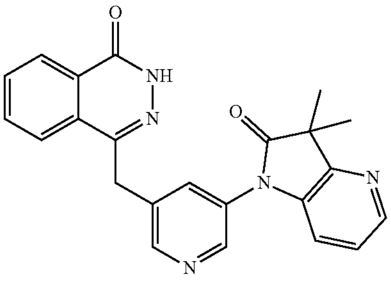 [SMILES: CC1(C)C(=O)N(c2cncc(Cc3n[nH]c(=O)c4ccccc34)c2)c2cccnc21] |
| 37 | 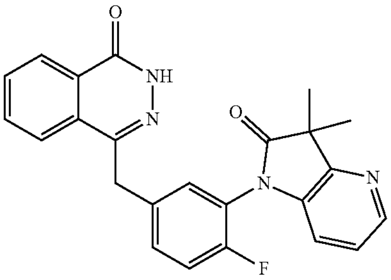 [SMILES: CC1(C)C(=O)N(c2cc(Cc3n[nH]c(=O)c4ccccc34)ccc2F)c2cccnc21] |
| 38 | 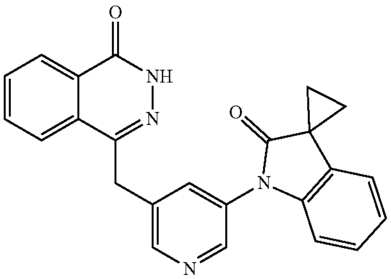 [SMILES: O=C1N(c2cncc(Cc3n[nH]c(=O)c4ccccc34)c2)c2ccccc2C12CC2] |
Yet another embodiment of the present invention is a method for inhibiting PARP in a patient (such as a patient in need thereof) by administering to the patient an effective amount of at least one compound of the present invention (for example, a compound of formula (I), or a pharmaceutically acceptable salt thereof, as defined above).

Yet another embodiment of the present invention is a method for treating an inflammatory, autoimmune or proliferative disease (e.g., via inhibition of PARP) by administering to a patient (such as a patient in need thereof) an effective amount of at least one compound of the present invention.

In one embodiment, the compounds of the present invention inhibit PARP (i.e., an effective amount of the compound is administered to inhibit PARP). In one embodiment, the compounds of the present invention inhibit PARP1 and/or PARP2 (i.e., an effective amount of the compound is administered to inhibit PARP1 and/or PARP2).

Yet another embodiment of the present invention is a method of treating an inflammatory, autoimmune or proliferative disease (e.g., via inhibition of PARP) by administering to a patient (such as a patient in need thereof) an effective amount of at least one compound of the present invention, in combination (simultaneously or sequentially) with at least one other anti-inflammatory, immunomodulator and/or anti-cancer agent.

The compounds of formula (I), and pharmaceutically acceptable esters and salts thereof, can be administered for the treatment, prevention and/or amelioration of diseases or disorders associated with PARP, in particular the amelioration of diseases or disorders mediated by PARP, including, but not limited to, inflammatory diseases or disorders, autoimmune diseases or disorders, and cancer and other proliferative diseases or disorders.

The compounds of the present invention are useful in the treatment of a variety of cancers, including, but not limited to:

- carcinoma, including that of the bladder, breast, colon, kidney, liver, lung, including small cell lung cancer, esophagus, gall bladder, ovary, pancreas, stomach, cervix, thyroid, prostate, and skin, including squamous cell carcinoma;
- hematopoietic tumors of lymphoid lineage, including leukemia, acute lymphocytic leukemia, acute lymphoblastic leukemia, B-cell lymphoma, T-cell lymphoma, Hodgkin's lymphoma, non-Hodgkins lymphoma, hairy cell lymphoma and Burkett's lymphoma;
- hematopoietic tumors of myeloid lineage, including acute and chronic myelogenous leukemias, myelodysplastic syndrome and promyelocytic leukemia;
- tumors of mesenchymal origin, including fibrosarcoma and rhabdomyosarcoma;
- tumors of the central and peripheral nervous system, including astrocytoma, neuroblastoma, glioma and schwannomas; and
- other tumors, including melanoma, seminoma, teratocarcinoma, osteosarcoma, xenoderoma pigmentosum, keratoctanthoma, thyroid follicular cancer and Kaposi's sarcoma.

The compounds of the present invention as modulators of apoptosis are useful in the treatment of cancer (including, but not limited to, those types mentioned herein above), viral infections (including, but not limited to, herpevirus, poxvirus, Epstein-Barr virus, Sindbis virus and adenovirus), prevention of AIDS development in HIV-infected individuals, autoimmune diseases (including, but not limited to, systemic lupus, erythematosus, autoimmune mediated glomerulonephritis, rheumatoid arthritis, psoriasis, inflammatory bowel disease, and autoimmune diabetes mellitus), neurodegenerative disorders (including, but not limited to, Alzheimer's disease, AIDS-related dementia, Parkinson's disease, amyotrophic lateral sclerosis, retinitis pigmentosa, spinal muscular atrophy and cerebellar degeneration), myelodysplastic syndromes, aplastic anemia, ischemic injury associated with myocardial infarctions, stroke and reperfusion injury, arrhythmia, atherosclerosis, toxin-induced or alcohol related liver diseases, hematological diseases (including, but not limited to, chronic anemia and aplastic anemia), degenerative diseases of the musculoskeletal system (including, but not limited to, osteoporosis and arthritis) aspirin-sensitive rhinosinusitis, cystic fibrosis, multiple sclerosis, kidney diseases and cancer pain.

The compounds of present invention can modulate the level of cellular RNA and DNA synthesis. The compounds described herein are therefore useful in the treatment of viral infections (including, but not limited to, HIV, human papilloma virus, herpesvirus, poxvirus, Epstein-Barr virus, Sindbis virus and adenovirus).

The compounds of the present invention are useful in the chemoprevention of cancer. Chemoprevention is defined as inhibiting the development of invasive cancer by either blocking the initiating mutagenic event or by blocking the progression of pre-malignant cells that have already suffered an insult or inhibiting tumor relapse. The compounds described herein are also useful in inhibiting tumor angiogenesis and metastasis. One embodiment of the present invention is a method of inhibiting tumor angiogenesis or metastasis in a patient (such as a patient in need thereof) by administering an effective amount of one or more compounds of the present invention.

Another embodiment of the present invention is a method of treating an immune system-related disease (e.g., an autoimmune disease), a disease or disorder involving inflammation (e.g., asthma, chronic obstructive pulmonary disease, rheumatoid arthritis, inflammatory bowel disease, glomerulonephritis, neuroinflammatory diseases, multiple sclerosis, uveitis and disorders of the immune system), cancer or other proliferative disease, a hepatic disease or disorder, or a renal disease or disorder. The method includes administering to a patient (such as a patient in need thereof) an effective amount of one or more compounds of the present invention.

Examples of immune disorders include, but are not limited to, psoriasis, rheumatoid arthritis, vasculitis, inflammatory bowel disease, dermatitis, osteoarthritis, asthma, inflammatory muscle disease, allergic disease (e.g., allergic rhinitis), vaginitis, interstitial cystitis, scleroderma, osteoporosis, eczema, allogeneic or xenogeneic transplantation (organ, bone marrow, stem cells and other cells and tissues) graft rejection, graft-versus-host disease, lupus erythematosus, inflammatory disease, type I diabetes, pulmonary fibrosis, dermatomyositis, Sjogren's syndrome, thyroiditis (e.g., Hashimoto's and autoimmune thyroiditis), myasthenia gravis, autoimmune hemolytic anemia, multiple sclerosis, cystic fibrosis, chronic relapsing hepatitis, primary biliary cirrhosis, allergic conjunctivitis and atopic dermatitis.

In one embodiment, the compounds described herein are used as immunosuppressants to prevent transplant graft rejections, allogeneic or xenogeneic transplantation rejection (organ, bone marrow, stem cells, other cells and tissues), and graft-versus-host disease. In other embodiments, transplant graft rejections result from tissue or organ transplants. In further embodiments, graft-versus-host disease results from bone marrow or stem cell transplantation. One embodiment is a method of preventing or decreasing the risk of transplant graft rejection, allogeneic or xenogeneic transplantation rejection (organ, bone marrow, stem cells, other cells and tissues), or graft-versus-host disease by administering to a patient (such as a patient in need thereof) an effective amount of one or more compounds of the present invention.

The compounds of the present invention are also useful in combination (administered together or sequentially) with known anti-cancer treatments, such as for example, but not limited to, radiation therapy or with cytostatic, cytotoxic or anticancer agents, such as, for example, but not limited to, DNA interactive agents, such as cisplatin or doxorubicin; topoisomerase II inhibitors, such as etoposide; topoisomerase I inhibitors such as CPT-11 or topotecan; tubulin interacting agents, such as paclitaxel, docetaxel or the epothilones (for example ixabepilone), either naturally occurring or synthetic; hormonal agents, such as tamoxifen; thymidilate synthase inhibitors, such as 5-fluorouracil; and anti-metabolites, such as methotrexate, other tyrosine kinase inhibitors such as Iressa and OSI-774; angiogenesis inhibitors; EGF inhibitors; VEGF inhibitors; CDK inhibitors; HDAC inhibiotrs, SRC inhibitors; c-Kit inhibitors; Her1/2 inhibitors and monoclonal antibodies directed against growth factor receptors such as erbitux (EGF) and herceptin (Her2) and other protein kinase modulators, or any combination of the foregoing.

The compounds of the present invention are also useful in combination (administered together or sequentially) with one or more steroidal, anti-inflammatory drugs, non-steroidal anti-inflammatory drugs (NSAIDs) or immune selective anti-inflammatory derivatives (ImSAIDs).

In another aspect, the invention further provides a pharmaceutical composition comprising one or more compounds of the present invention (such as a compound of formula (I) or a pharmaceutically acceptable salt thereof, and one or more pharmaceutically acceptable carriers. The pharmaceutical composition may further comprise one or more additional active ingredients identified herein, such as other anti-cancer agents.

In one embodiment, the pharmaceutical composition includes a therapeutically effective amount of one or more compounds of formula (I) or a pharmaceutically acceptable salt thereof.

Yet another embodiment is a method of treating cancer in a patient (such as a patient in need thereof) by administering a therapeutically effective amount of a compound of the present invention. For example, the compounds of the present invention are effective for treating hematopoietic tumors of lymphoid lineage, leukemia, acute lymphocytic leukemia, acute lymphoblastic leukemia, B-cell lymphoma, T-cell lymphoma, Hodgkin's lymphoma, non-Hodgkins lymphoma, hairy cell lymphoma and Burkett's lymphoma; hematopoietic tumors of myeloid lineage, acute myelogenous leukemias, chronic myelogenous leukemias, myelodysplastic syndrome and promyelocytic leukemia. The compounds of the present invention are also effective for treating carcinoma of the bladder, carcinoma of the breast, carcinoma of the colon, carcinoma of the kidney, carcinoma of the liver, carcinoma of the lung, small cell lung cancer, esophageal cancer, gall bladder cancer, ovarian cancer, pancreatic cancer, stomach cancer, cervical cancer, thyroid cancer, prostate cancer, skin cancer, squamous cell carcinoma, tumors of mesenchymal origin, fibrosarcoma, rhabdomyosarcoma, tumors of the central and peripheral nervous system, astrocytoma, neuroblastoma, glioma, schwannoma, melanoma, seminoma, teratocarcinoma, osteosarcoma, xenoderoma pigmentosum, keratoctanthoma, thyroid follicular cancer and Kaposi's sarcoma.

Yet another embodiment is a method of treating leukemia in a patient (such as a patient in need thereof) by administering a therapeutically effective amount of a compound of the present invention. For example, the compounds of the present invention are effective for treating carcinoma of the breast, ovarian cancer, carcinoma of the liver, carcinoma of the lung, small cell lung cancer, esophageal cancer, gall bladder cancer, ovarian cancer, pancreatic cancer or stomach cancer.

DETAILED DESCRIPTION OF THE INVENTION

As used herein the following definitions shall apply unless otherwise indicated. Further many of the groups defined herein can be optionally substituted. The listing of substituents in the definition is exemplary and is not to be construed to limit the substituents defined elsewhere in the specification.

The term "alkyl", unless otherwise specified, refers to a straight or branched hydrocarbon chain radical consisting solely of carbon and hydrogen atoms, containing no unsaturation, having from one to eight carbon atoms, and which is attached to the rest of the molecule by a single bond, e.g., methyl, ethyl, n-propyl, 1-methylethyl(isopropyl), n-butyl, n-pentyl, and 1,1-dimethylethyl (t-butyl). The term "$C_{1-6}$alkyl" refers to an alkyl group as defined above having up to 6 carbon atoms. The term "$C_{1-4}$alkyl" refers to an alkyl group as defined above having up to 4 carbon atoms. In appropriate circumstances, the term "alkyl" refers to a hydrocarbon chain radical as mentioned above which is bivalent.

The term "alkenyl", unless otherwise specified, refers to an aliphatic hydrocarbon group containing a carbon-carbon double bond and which may be a straight or branched or branched chain having about 2 to about 10 carbon atoms, e.g., ethenyl, 1-propenyl, 2-propenyl(allyl), iso-propenyl, 2-methyl-1-propenyl, 1-butenyl, and 2-butenyl. The term "($C_{2-6}$)alkenyl" refers to an alkenyl group as defined above having up to 6 carbon atoms.

The term "alkynyl," unless otherwise specified, refers to a straight or branched chain hydrocarbyl radical having at least one carbon-carbon triple bond, and having in the range of 2 to up to 12 carbon atoms (with radicals having in the range of 2 to up to 10 carbon atoms presently being preferred) e.g., ethynyl, propynyl, and butnyl. The term "($C_{2-6}$)alkynyl" refers to an alkynyl group as defined above having up to 6 carbon atoms.

The term "alkoxy," unless otherwise specified, denotes an alkyl, cycloalkyl, or cycloalkylalkyl group as defined above attached via an oxygen linkage to the rest of the molecule. The term "substituted alkoxy" refers to an alkoxy group where the alkyl constituent is substituted (i.e., —O—(substituted alkyl) wherein the term "substituted alkyl" is the same as defined above for "alkyl". For example "alkoxy" refers to the group-O-alkyl, including from 1 to 8 carbon atoms of a straight, branched, cyclic configuration and combinations thereof attached to the parent structure through oxygen. Examples include methoxy, ethoxy, propoxy, isopropoxy, cyclopropyloxy, and cyclohexyloxy.

The term "cycloalkyl," unless otherwise specified, denotes a non-aromatic mono or multicyclic ring system of about 3 to 12 carbon atoms such as cyclopropyl, cyclobutyl, cyclopentyl, and cyclohexyl. Examples of multicyclic cycloalkyl groups include perhydronaphthyl, adamantyl and norbornyl groups, bridged cyclic groups, and sprirobicyclic groups, e.g., sprio (4,4) non-2-yl. The term "($C_{3-8}$) cycloalkyl" refers to a cycloalkyl group as defined above having up to 8 carbon atoms.

The term "cycloalkylalkyl," unless otherwise specified, refers to a cyclic ring-containing radical containing in the range of about 3 up to 8 carbon atoms directly attached to an alkyl group which are then attached to the main structure at any carbon from the alkyl group that results in the creation of a stable structure such as cyclopropylmethyl, cyclobutylethyl, and cyclopentylethyl.

The term "cycloalkenyl," unless otherwise specified, refers to cyclic ring-containing radicals containing in the range of about 3 up to 8 carbon atoms with at least one carbon-carbon double bond such as cyclopropenyl, cyclobutenyl, and cyclopentenyl. The term "cycloalkenylalkyl" refers to a cycloalkenyl group directly attached to an alkyl group which are then attached to the main structure at any carbon from the alkyl group that results in the creation of a stable structure.

The term "aryl," unless otherwise specified, refers to aromatic radicals having in the range of 6 up to 20 carbon atoms such as phenyl, naphthyl, tetrahydronaphthyl, indanyl, and biphenyl.

The term "arylalkyl," unless otherwise specified, refers to an aryl group as defined above directly bonded to an alkyl group as defined above, e.g., $—CH_2C_6H_5$ and $—C_2H_5C_6H_5$.

The term "heterocyclic ring," unless otherwise specified, refers to a non-aromatic 3 to 15 member ring radical which consists of carbon atoms and at least one heteroatom selected from nitrogen, phosphorus, oxygen and sulfur. For purposes of this invention, the heterocyclic ring radical may be a mono-, bi-, tri- or tetracyclic ring system, which may include fused, bridged or spiro ring systems, and the nitrogen, phosphorus, carbon, oxygen or sulfur atoms in the heterocyclic ring radical may be optionally oxidized to various oxidation states. In addition, the nitrogen atom may be optionally quaternized. The heterocyclic ring radical may be attached to the main structure at any heteroatom or carbon atom that results in the creation of a stable structure.

The term "heterocyclyl," unless otherwise specified, refers to a heterocylic ring radical as defined above. The heterocylcyl ring radical may be attached to the main structure at any heteroatom or carbon atom that results in the creation of a stable structure.

The term "heterocyclylalkyl," unless otherwise specified, refers to a heterocylic ring radical as defined above directly bonded to an alkyl group. The heterocyclylalkyl radical may be attached to the main structure at carbon atom in the alkyl group that results in the creation of a stable structure. Examples of such heterocycloalkyl radicals include, but are not limited to, dioxolanyl, thienyl[1,3]dithianyl, decahydroisoquinolyl, imidazolinyl, imidazolidinyl, isothiazolidinyl, isoxazolidinyl, morpholinyl, octahydroindolyl, octahydroisoindolyl, 2-oxopiperazinyl, 2-oxopiperidinyl, 2-oxopyrrolidinyl, oxazolidinyl, piperidinyl, piperazinyl, 4-piperidonyl, pyrrolidinyl, pyrazolidinyl, quinuclidinyl, thiazolidinyl, tetrahydrofuryl, trithianyl, tetrahydropyranyl, thiomorpholinyl, thiamorpholinyl, 1-oxo-thiomorpholinyl, and 1,1-dioxo-thiomorpholinyl.

The term "heteroaryl," unless otherwise specified, refers to an optionally substituted 5 to 14 member aromatic ring having one or more heteroatoms selected from N, O, and S as ring atoms. The heteroaryl may be a mono-, bi- or tricyclic ring system. Examples of such "heterocyclic ring" or "heteroaryl" radicals include, but are not limited to, oxazolyl, thiazolyl, imidazolyl, pyrrolyl, furanyl, pyridinyl, pyrimidinyl, pyrazinyl, benzofuranyl, indolyl, benzothiazolyl, benzoxazolyl, carbazolyl, quinolyl, isoquinolyl, azetidinyl, acridinyl, benzodioxolyl, benzodioxanyl, benzofuranyl, carbazolyl, cinnolinyl, dioxolanyl, indolizinyl, naphthyridinyl, perhydroazepinyl, phenazinyl, phenothiazinyl, phenoxazinyl, phthalazinyl, pteridinyl, purinyl, quinazolinyl, quinoxalinyl, tetrazoyl, tetrahydroisoquinolyl, piperidinyl, piperazinyl, 2-oxopiperazinyl, 2-oxopiperidinyl, 2-oxopyrrolidinyl, 2-oxoazepinyl, azepinyl, 4-piperidonyl, pyrrolidinyl, pyridazinyl, oxazolinyl, oxazolidinyl, triazolyl, indanyl, isoxazolyl, isoxazolidinyl, morpholinyl, thiazolinyl, thiazolidinyl, isothiazolyl, quinuclidinyl, isothiazolidinyl, isoindolyl, indolinyl, isoindolinyl, octahydroindolyl, octahydroisoindolyl, decahydroisoquinolyl, benzimidazolyl, thiadiazolyl, benzopyranyl, tetrahydrofuryl, tetrahydropyranyl, thienyl, benzothienyl, thiamorpholinyl, thiamorpholinyl sulfoxide, thiamorpholinyl sulfone, dioxaphospholanyl, oxadiazolyl, chromanyl, and isochromanyl. The heteroaryl ring radical may be attached to the main structure at any heteroatom or carbon atom that results in the creation of a stable structure. The term "substituted heteroaryl" also includes ring systems substituted with one or more oxide (—O—) substituents, such as pyridinyl N-oxides.

The term "heteroarylalkyl," unless otherwise specified, refers to a heteroaryl ring radical as defined above directly bonded to an alkyl group. The heteroarylalkyl radical may be attached to the main structure at any carbon atom from alkyl group that results in the creation of a stable structure.

The term "cyclic ring" refers to a cyclic ring containing 3 to 10 carbon atoms.

The term "substituted" unless otherwise specified, refers to substitution with any one or any combination of the following substituents which may be the same or different and are independently selected from hydrogen, hydroxy, halogen, carboxyl, cyano, nitro, oxo (=O), thio (=S), substituted or unsubstituted alkyl, substituted or unsubstituted alkoxy, substituted or unsubstituted alkenyl, substituted or unsubstituted alkynyl, substituted or unsubstituted aryl, substituted or unsubstituted arylalkyl, substituted or unsubstituted cycloalkyl, substituted or unsubstituted cycloalkylalkyl, substituted or unsubstituted cycloalkenyl, substituted or unsubstituted cycloalkenylalkyl, substituted or unsubstituted heteroaryl, substituted or unsubstituted heteroarylalkyl, substituted or unsubstituted heterocyclic ring, substituted heterocyclylalkyl ring, substituted or unsubstituted guanidine, $COOR^t$, $—C(O)R^v$, $—C(S)R^v$, $—C(O)NR^tR^u$, $—C(O)ONR^tR^u$, $—NR^tR^u$, $—NR^tCONR^uR^v$, $—N(R^t)SOR^u$, $—N(R^t)SO_2R^u$, $—(=N—N(R^t)R^u)$, $—NR^tC(O)OR^u$, $—NR^tR^u$, $—NR^tC(O)R^u—$, $—NR^tC(S)R^u—NR^tC(S)NR^tR^u$, $—SONR^tR^u—$, $—SO_2NR^tR^u—$, $—OR^t$, $—OR^tC(O)NR^uR^v$, $—OR^tC(O)OR^u—$, $—OC(O)R^t$, $—OC(O)NR^tR^u$, $—R^tNR^uC(O)R^v$, $—R^tOR^u$, $—R^tC(O)OR^u$, $—R^tC(O)NR^uR^v$, $—R^tC(O)R^u$, $—R^tOC(O)R^u$, $—SR^t$, $—SOR^t$, $—SO_2R^t$, and $—ONO_2$, wherein $R^t$, $R^u$ and $R^v$ in each of the above groups can be hydrogen, substituted or unsubstituted alkyl, substituted or unsubstituted alkoxy, substituted or unsubstituted alkenyl, substituted or unsubstituted alkynyl, substituted or unsubstituted aryl, substituted or unsubstituted arylalkyl, substituted or unsubstituted cycloalkyl, substituted or unsubstituted cycloalkylalkyl, substituted or unsubstituted cycloalkenyl, substituted or unsubstituted amino, substituted or unsubstituted heteroaryl, substituted or unsubstituted heteroarylalkyl, substituted or unsubstituted heterocyclic ring, or substituted heterocyclylalkyl ring, or any two of $R^t$, $R^u$ and $R^v$ may be joined to form a substituted or unsubstituted saturated or unsaturated 3-10 membered ring, which may optionally include heteroatoms which may be the same or different and are selected from O, $NR^q$ (where $R^q$ can be hydrogen or $C_{1-6}$ alkyl) or S. Substitution or the combinations of substituents envisioned by this invention are preferably those that result in the formation of a stable or chemically feasible compound. The term stable as used herein refers to the compounds or the structure that are not substantially altered when subjected to conditions to allow for their production, detection and preferably their recovery, purification and incorporation into a pharmaceutical composition. The substituents in the aforementioned "substituted" groups cannot be further substituted. For example, when the substituent on "substituted alkyl" is "substituted aryl", the substituent on "substituted aryl" cannot be "substituted alkenyl".

The term "halo", "halide", or, alternatively, "halogen" means fluoro, chloro, bromo or iodo. The terms "haloalkyl," "haloalkenyl," "haloalkynyl" and "haloalkoxy" include alkyl, alkenyl, alkynyl and alkoxy structures that are substituted with one or more halo groups or with combinations thereof. For example, the terms "fluoroalkyl" and "fluoroalkoxy" include haloalkyl and haloalkoxy groups, respectively, in which the halo is fluorine.

The term "protecting group" or "PG" refers to a substituent that is employed to block or protect a particular functionality. Other functional groups on the compound may remain reactive. For example, an "amino-protecting group" is a substituent attached to an amino group that blocks or protects the amino functionality in the compound. Suitable amino-protecting groups include, but are not limited to, acetyl, trifluoroacetyl, tert-butoxycarbonyl (BOC), benzyloxycarbonyl(CBz) and 9-fluorenylmethylenoxycarbonyl (Fmoc). Similarly, a "hydroxy-protecting group" refers to a substituent of a hydroxy group that blocks or protects the hydroxy functionality. Suitable hydroxy-protecting groups include, but are not limited to, acetyl and silyl. A "carboxy-protecting group" refers to a substituent of the carboxy group that blocks or protects the carboxy functionality. Suitable carboxy-protecting groups include, but are not limited to, $-CH_2CH_2SO_2Ph$, cyanoethyl, 2-(trimethylsilyl) ethyl, 2-(trimethylsilyl) ethoxymethyl, 2-(p-toluenesulfonyl)ethyl, 2-(p-nitrophenylsulfenyl)ethyl, 2-(diphenylphosphino)-ethyl, and nitroethyl. For a general description of protecting groups and their use, see T. W. Greene, Protective Groups in Organic Synthesis, John Wiley & Sons, New York, 1991.

Certain of the compounds described herein may contain one or more asymmetric centres and can thus give rise to enantiomers, diastereomers, and other stereoisomeric forms that can be defined, in terms of absolute stereochemistry, as (R)- or (S)-. The present chemical entities, pharmaceutical compositions and methods are meant to include all such possible isomers, including racemic mixtures, optically pure forms and intermediate mixtures. Non-limiting examples of intermediate mixtures include, e.g., a mixture of isomers in a ratio of 10:90, 13:87, 17:83, 20:80, or 22:78. Optically active (R)- and(S)-isomers can be prepared using chiral synthons or chiral reagents, or resolved using conventional techniques. When the compounds described herein contain olefinic double bonds or other centres of geometric asymmetry, and unless specified otherwise, it is intended that the compounds include both E and Z geometric isomers.

The term "tautomers" as used herein refers to compounds, which are characterized by relatively easy interconversion of isomeric forms in equilibrium. These isomers are intended to be covered by this invention. "Tautomers" are structurally distinct isomers that interconvert by tautomerization. "Tautomerization" is a form of isomerization and includes prototropic or proton-shift tautomerization, which is considered a subset of acid-base chemistry. "Prototropic tautomerization" or "proton-shift tautomerization" involves the migration of a proton accompanied by changes in bond order, often the interchange of a single bond with an adjacent double bond. Where tautomerization is possible (e.g. in solution), a chemical equilibrium of tautomers can be reached. An example of tautomerization is keto-enol tautomerization. A specific example of keto-enol tautomerization is the interconversion of pentane-2,4-dione and 4-hydroxypent-3-en-2-one tautomers. Another example of tautomerization is phenol-keto tautomerization. A specific example of phenol-keto tautomerization is the interconversion of pyridin-4-ol and pyridin-4 (1H)-one tautomers.

A "leaving group or atom" is any group or atom that will, under the reaction conditions, cleave from the starting material, thus promoting reaction at a specified site. Suitable examples of such groups unless otherwise specified are halogen atoms and mesyloxy, p-nitrobenzensulphonyloxy and tosyloxy groups.

The term "prodrug" refers to a compound, which is an inactive precursor of a compound, converted into its active form in the body by normal metabolic processes. Prodrug design is discussed generally in Hardma, et al. (Eds.), Goodman and Gilman's The Pharmacological Basis of Therapeutics, 9th ed., pp. 11-16 (1996). A thorough discussion is provided in Higuchi, et al., Prodrugs as Novel Delivery Systems, Vol. 14, ASCD Symposium Series, and in Roche (ed.), Bioreversible Carriers in Drug Design, American Pharmaceutical Association and Pergamon Press (1987) .To illustrate, prodrugs can be converted into a pharmacologically active form through hydrolysis of, for example, an ester or amide linkage, thereby introducing or exposing a functional group on the resultant product. The prodrugs can be designed to react with an endogenous compound to form a water-soluble conjugate that further enhances the pharmacological properties of the compound, for example, increased circulatory half-life. Alternatively, prodrugs can be designed to undergo covalent modification on a functional group with, for example, glucuronic acid, sulfate, glutathione, amino acids, or acetate. The resulting conjugate can be inactivated and excreted in the urine, or rendered more potent than the parent compound. High molecular weight conjugates also can be excreted into the bile, subjected to enzymatic cleavage, and released back into circulation, thereby effectively increasing the biological half-life of the originally administered compound.

The term "ester" refers to a compound, which is formed by reaction between an acid and an alcohol with elimination of water. An ester can be represented by the general formula RCOOR'.

These prodrugs and esters are intended to be covered within the scope of this invention.

Additionally, the present invention also includes compounds which differ only in the presence of one or more isotopically enriched atoms for example replacement of hydrogen with deuterium or tritium, or the replacement of a carbon by 13C- or $^{14}C$-enriched carbon.

The compounds of the present invention may also contain unnatural proportions of atomic isotopes at one or more of atoms that constitute such compounds. For example, the compounds may be radiolabeled with radioactive isotopes, such as for example tritium (3H), iodine-125 ($^{125}I$) or carbon-14 ($^{14}C$). All isotopic variations of the compounds of the present invention, whether radioactive or not, are encompassed within the scope of the present invention.

Pharmaceutically acceptable salts forming part of this invention include, e.g., salts derived from inorganic bases such as Li, Na, K, Ca, Mg, Fe, Cu, Zn, and Mn; salts of organic bases such as N,N'-diacetylethylenediamine, glucamine, triethylamine, choline, hydroxide, dicyclohexylamine, metformin, benzylamine, trialkylamine, and thiamine; chiral bases such as alkylphenylamine, glycinol, and phenyl glycinol; salts of natural amino acids such as glycine, alanine, valine, leucine, isoleucine, norleucine, tyrosine, cystine, cysteine, methionine, proline, hydroxy proline, histidine, omithine, lysine, arginine, and serine; quaternary ammonium salts of the compounds of invention with alkyl halides, alkyl sulphates such as Mel and $(Me)_2SO_4$; non-natural amino acids such as D-isomers or substituted amino acids; guanidine; and substituted guanidine wherein the substituents are selected from nitro, amino, alkyl, alkenyl, alkynyl, ammonium or substituted ammonium salts and aluminum salts. Salts may include acid addition salts where appropriate which are sulphates, nitrates, phosphates, perchlorates, borates, hydrohalides (e.g., hydrochlorides), acetates, tartrates, maleates, citrates, fumarates, succinates, palmoates, methanesulphonates, benzoates, salicylates, benzenesulfonates, ascorbates, glycerophosphates, and ketoglutarates.

When ranges are used herein for physical properties, such as molecular weight, or chemical properties, such as chemical formulae, all combinations and sub-combinations of ranges and specific embodiments therein are intended to be included. The term "about" when referring to a number or a numerical range means that the number or numerical range referred to is an approximation within experimental variability (or within statistical experimental error), and thus the number or numerical range may vary from, for example, between 1% and 15% of the stated number or numerical range. The term "comprising" (and related terms such as "comprise" or "comprises" or "having" or "including") includes those embodiments, for example, an embodiment of any composition of matter, composition, method, or process, or the like, that "consist of' or "consist essentially of" the described features.

The following abbreviations and terms have the indicated meanings throughout: AIDS=Acquired Immuno Deficiency Syndrome; HIV=Human Immunodeficiency Virus; Abbreviations used herein have their conventional meaning within the chemical and biological arts.

The term "cell proliferation" refers to a phenomenon by which the cell number has changed as a result of division. This term also encompasses cell growth by which the cell morphology has changed (e.g., increased in size) consistent with a proliferative signal.

The term "co-administration," "administered in combination with," and their grammatical equivalents, as used herein, encompasses administration of two or more agents to an animal so that both agents and/or their metabolites are present in the animal at the same time. Co-administration includes simultaneous administration in separate compositions, administration at different times in separate compositions, or administration in a composition in which both agents are present.

The term "effective amount" or "therapeutically effective amount" refers to that amount of a compound described herein that is sufficient to show the intended application including but not limited to disease treatment, as defined below. The therapeutically effective amount may vary depending upon the intended application (in vitro or in vivo), or the subject and disease condition being treated, e.g., the weight and age of the subject, the severity of the disease condition, the manner of administration and the like, which can readily be determined by one of ordinary skill in the art. The term also applies to a dose that will induce a particular response in target cells, e.g. reduction of platelet adhesion and/or cell migration. The specific dose will vary depending on the compound chosen, the dosing regimen to be followed, whether it is administered in combination with other compounds, timing of administration, the tissue to which it is administered, and the physical delivery system in which it is carried. In one embodiment, the amount of compound administered ranges from about 0.1 mg to 5 g, from about 1 mg to 2.0 g, from about 100 mg to 1.5 g, from about 200 mg to 1.5 g, from about 400 mg to 1.5 g, and from about 400 mg to 1.0 g.

As used herein, the terms "treatment," "treating," or "ameliorating" are used interchangeably. These terms refer to an approach for obtaining beneficial or desired results including but not limited to therapeutic benefit and/or a prophylactic benefit. By therapeutic benefit is meant eradication or amelioration of the underlying disorder being treated. Also, a therapeutic benefit is achieved with the eradication or amelioration of one or more of the physiological symptoms associated with the underlying disorder such that an improvement is observed in the patient, notwithstanding that the patient may still be afflicted with the underlying disorder. For prophylactic benefit, the compositions may be administered to a patient at risk of developing a particular disease, or to a patient reporting one or more of the physiological symptoms of a disease, even though a diagnosis of this disease may not have been made.

A "therapeutic effect," as that term is used herein, encompasses a therapeutic benefit and/or a prophylactic benefit as described above. A prophylactic effect includes delaying or eliminating the appearance of a disease or condition, delaying or eliminating the onset of symptoms of a disease or condition, slowing, halting, or reversing the progression of a disease or condition, or any combination thereof.

The term "subject" or "patient" refers to an animal, such as a mammal, for example a human. The methods described herein can be useful in both human therapeutics and veterinary applications (e.g., dogs, cats, cows, sheep, pigs, horses, goats, chickens, turkeys, ducks, and geese).

In some embodiments, the patient is a mammal, and in some embodiments, the patient is a human.

"Radiation therapy" as used herein means exposing a patient, using routine methods and compositions known to the practitioner, to radiation emitters such as alpha-particle emitting radionuclides (e.g., actinium and thorium radionuclides), low linear energy transfer (LET) radiation emitters (i.e. beta emitters), conversion electron emitters (e.g. strontium-89 and samarium-153-EDTMP), or high-energy radiation, including without limitation x-rays, gamma rays, and neutrons.

The term "pharmaceutically acceptable excipient" as used herein includes, but is not limited to, any and all solvents, dispersion media, coatings, antibacterial and antifungal agents, isotonic and absorption delaying agents, one or more suitable diluents, fillers, salts, disintegrants, binders, lubricants, glidants, wetting agents, controlled release matrices, colorants/flavoring, carriers, buffers, stabilizers, solubilizers, and combinations thereof. Except insofar as any conventional media or agent is incompatible with the active ingredient, its use in the therapeutic compositions of the invention is contemplated. Supplementary active ingredients can also be incorporated into the compositions.

Any of the methods of the invention described herein may be applied to cell populations in vivo or ex vivo. "In vivo" means within a living individual, as within an animal or human or in a subject's body. In this context, the methods of the invention may be used therapeutically or prophylactically in an individual. "Ex vivo" or "In vitro" means outside of a living individual. Examples of ex vivo cell populations include in vitro cell cultures and biological samples including but not limited to fluid or tissue samples obtained from individuals. Such samples may be obtained by methods known in the art. Exemplary biological fluid samples include blood, cerebrospinal fluid, urine, and saliva. Exemplary tissue samples include tumors and biopsies thereof. In this context, the invention may be used for a variety of purposes, including therapeutic and experimental purposes. For example, the invention may be used ex vivo or in vitro to determine the optimal schedule and/or dosing of administration of a PARP inhibitor for a given indication, cell type, individual, and other parameters. Information gleaned from such use may be used for experimental or diagnostic purposes or in the clinic to set protocols for in vivo treatment. Other ex vivo uses for which the invention may be suited are described below or will become apparent to those skilled in the art.

Pharmaceutical Compositions

The present invention provides a pharmaceutical composition comprising one or more compounds of the present invention. The pharmaceutical composition may include one or more additional active ingredients as described herein. The pharmaceutical composition may be administered for any of the disorders described herein.

The subject pharmaceutical compositions are typically formulated to provide a therapeutically effective amount of a compound of the present invention as the active ingredient. Where desired, the pharmaceutical compositions contain a compound of the present invention as the active ingredient and one or more pharmaceutically acceptable carriers or excipients, such as inert solid diluents and fillers, diluents, including sterile aqueous solution and various organic solvents, permeation enhancers, solubilizers and adjuvants.

The pharmaceutical compositions can be administered alone or in combination with one or more other agents, which are also typically administered in the form of pharmaceutical compositions. Where desired, the subject compounds and other agent(s) may be mixed into a preparation or both components may be formulated into separate preparations to use them in combination separately or at the same time.

Methods include administration of a compound of the present invention by itself, or in combination as described herein, and in each case optionally including one or more suitable diluents, fillers, salts, disintegrants, binders, lubricants, glidants, wetting agents, controlled release matrices, colorants/flavoring, carriers, excipients, buffers, stabilizers, solubilizers, and combinations thereof.

Preparations of various pharmaceutical compositions are known in the art. See, e.g., Anderson, Philip O.; Knoben, James E.; Troutman, William G, eds., Handbook of Clinical Drug Data, Tenth Edition, McGraw-Hill, 2002; Pratt and Taylor, eds., Principles of Drug Action, Third Edition, Churchill Livingston, New York, 1990; Katzung, ed., Basic and Clinical Pharmacology, Ninth Edition, McGraw Hill, 2003; Goodman and Gilman, eds., The Pharmacological Basis of Therapeutics, Tenth Edition, McGraw Hill, 2001; Remingtons Pharmaceutical Sciences, 20th Ed., Lippincott Williams & Wilkins., 2000; Martindale, The Extra Pharmacopoeia, Thirty-Second Edition (The Pharmaceutical Press, London, 1999), all of which are incorporated by reference herein in their entirety.

The compounds or pharmaceutical composition of the present invention can be administered by any route that enables delivery of the compounds to the site of action, such as oral routes, intraduodenal routes, parenteral injection (including intravenous, intraarterial, subcutaneous, intramuscular, intravascular, intraperitoneal or infusion), topical administration (e.g. transdermal application), rectal administration, via local delivery by catheter or stent or through inhalation. The compounds can also be administered intraadiposally or intrathecally.

The compositions can be administered in solid, semi-solid, liquid or gaseous form, or may be in dried powder, such as lyophilized form. The pharmaceutical compositions can be packaged in forms convenient for delivery, including, for example, solid dosage forms such as capsules, sachets, cachets, gelatins, papers, tablets, capsules, suppositories, pellets, pills, troches, and lozenges. The type of packaging will generally depend on the desired route of administration. Implantable sustained release formulations are also contemplated, as are transdermal formulations.

Method of Treatment

The present invention also provides methods of using the compounds or pharmaceutical compositions of the present invention to treat disease conditions, including, but not limited to, diseases associated with overexpression of PARP and/or due to an excess of PARP.

The treatment methods provided herein comprise administering to the subject (such as a subject in need thereof) a therapeutically effective amount of a compound of the invention. In one embodiment, the present invention provides a method of treating an inflammation disorder, including autoimmune diseases in a mammal. The method comprises administering to the mammal a therapeutically effective amount of a compound of the present invention.

It will be appreciated that the treatment methods of the invention described herein are useful in the fields of human medicine and veterinary medicine. Thus, the individual to be treated may be a mammal, preferably human, or other animal. For veterinary purposes, individuals include, but are not limited to, farm animals including cows, sheep, pigs, horses, and goats; companion animals such as dogs and cats; exotic and/or zoo animals; laboratory animals including mice, rats, rabbits, guinea pigs, and hamsters; and poultry such as chickens, turkeys, ducks, and geese.

The invention also relates to a method of treating a hyperproliferative disorder in a mammal that comprises administering to said mammal a therapeutically effective amount of a compound of the present invention. In some embodiments, the method relates to the treatment of cancer, such as acute myeloid leukemia, thymus, brain, lung, squamous cell, skin, eye, retinoblastoma, intraocular melanoma, oral cavity and oropharyngeal, bladder, gastric, stomach, pancreatic, bladder, breast, cervical, head, neck, renal, kidney, liver, ovarian, prostate, colorectal, esophageal, testicular, gynecological, thyroid, CNS, PNS, AIDS-related (e.g. lymphoma and Kaposi's sarcoma) or viral-induced cancer. In some embodiments, said method relates to the treatment of a non-cancerous hyperproliferative disorder such as benign hyperplasia of the skin (e.g., psoriasis), restenosis, or prostate (e.g., benign prostatic hypertrophy (BPH)).

The invention also relates to a method of treating diseases related to vasculogenesis or angiogenesis in a mammal that comprises administering to said mammal a therapeutically effective amount of a compound of the present invention. In some embodiments, said method is for treating a disease selected from the group consisting of tumor angiogenesis, chronic inflammatory disease such as rheumatoid arthritis, atherosclerosis, inflammatory bowel disease, skin diseases such as psoriasis, eczema, and scleroderma, diabetes, diabetic retinopathy, retinopathy of prematurity, age-related macular degeneration, hemangioma, glioma, melanoma, Kaposi's sarcoma and ovarian, breast, lung, pancreatic, prostate, colon and epidermoid cancer.

Patients that can be treated with compounds of the present invention according to the methods of this invention include, for example, patients that have been diagnosed as having psoriasis; restenosis; atherosclerosis; BPH; breast cancer such as a ductal carcinoma in duct tissue in a mammary gland, medullary carcinomas, colloid carcinomas, tubular carcinomas, and inflammatory breast cancer; ovarian cancer, including epithelial ovarian tumors such as adenocarcinoma in the ovary and an adenocarcinoma that has migrated from the ovary into the abdominal cavity; uterine cancer; cervical cancer such as adenocarcinoma in the cervix epithelial including squamous cell carcinoma and adenocarcinomas; prostate cancer, such as a prostate cancer selected from the following: an adenocarcinoma or an adenocarinoma that has migrated to the bone; pancreatic cancer such as epitheliod carcinoma in the pancreatic duct tissue and an adenocarcinoma in a pancreatic duct; bladder cancer such as a transitional cell carcinoma in urinary bladder, urothelial carcinomas (transitional cell carcinomas), tumors in the urothelial cells that line the bladder, squamous cell carcinomas, adenocarcinomas, and small cell cancers; leukemia such as acute myeloid leukemia (AML), acute lymphocytic leukemia, chronic lymphocytic leukemia, chronic myeloid leukemia, hairy cell leukemia, myelodysplasia, myeloproliferative disorders, acute myelogenous leukemia (AML), chronic myelogenous leukemia (CML), mastocytosis, chronic lymphocytic leukemia (CLL), multiple myeloma (MM), and myelodysplastic syndrome (MDS); bone cancer; lung cancer such as non-small cell lung cancer (NSCLC), which is divided into squamous cell carcinomas, adenocarcinomas, and large cell undifferentiated carcinomas, and small cell lung cancer; skin cancer such as basal cell carcinoma, melanoma, squamous cell carcinoma and actinic keratosis, which is a skin condition that sometimes develops into squamous cell carcinoma; eye retinoblastoma; cutaneous or intraocular (eye) melanoma; primary liver cancer (cancer that begins in the liver); kidney cancer; thyroid cancer such as papillary, follicular, medullary and anaplastic; AIDS-related lymphoma such as diffuse large B-cell lymphoma, B-cell immunoblastic lymphoma and small non-cleaved cell lymphoma; Kaposi's Sarcoma; viral-induced cancers including hepatitis B virus (HBV), hepatitis C virus (HCV), and hepatocellular carcinoma; human lymphotropic virus-type 1 (HTLV-I) and adult T-cell leukemia/lymphoma; and human papilloma virus (HPV) and cervical cancer; central nervous system cancers (CNS) such as primary brain tumor, which includes gliomas (astrocytoma, anaplastic astrocytoma, or glioblastoma multiforme), Oligodendroglioma, Ependymoma, Meningioma, Lymphoma, Schwannoma, and Medulloblastoma; peripheral nervous system (PNS) cancers such as acoustic neuromas and malignant peripheral nerve sheath tumor (MPNST) including neurofibromas and schwannomas, malignant fibrous cytoma, malignant fibrous histiocytoma, malignant meningioma, malignant mesothelioma, and malignant mixed Müllerian tumor; oral cavity and oropharyngeal cancer such as, hypopharyngeal cancer, laryngeal cancer, nasopharyngeal cancer, and oropharyngeal cancer; stomach cancer such as lymphomas, gastric stromal tumors, and carcinoid tumors; testicular cancer such as germ cell tumors (GCTs), which include seminomas and nonseminomas, and gonadal stromal tumors, which include Leydig cell tumors and Sertoli cell tumors; thymus cancer such as to thymomas, thymic carcinomas, Hodgkin disease, non-Hodgkin lymphomas carcinoids or carcinoid tumors; rectal cancer; and colon cancer.

In another aspect of the present invention, methods are provided for treating an ophthalmic disease by administering one or more compounds or pharmaceutical compositions described herein to the eye of a subject.

The present invention further provides methods of inhibiting PARP by contacting a PARP with an amount of a compound of the present invention sufficient to inhibit the activity of the PARP enzyme. In some embodiments, the invention provides methods of inhibiting PARP enzyme activity by contacting a PARP enzyme with an amount of a compound of the invention sufficient to inhibit the activity of the PARP enzyme. In some embodiments, the invention provides methods of inhibiting PARP enzyme activity. Such inhibition can take place in solution, in a cell expressing one or more PARP enzyme, in a tissue comprising a cell expressing the PARP, or in an organism expressing PARP. In some embodiments, the invention provides methods of inhibiting PARP activity in an animal (including mammals such as humans) by contacting said animal with an amount of a compound of the invention sufficient to inhibit the activity of the PARP enzyme in said animal.

The following general methodology described herein provides the manner and process of making and using the compounds of the present invention and are illustrative rather than limiting. Further modification of provided methodology and additionally new methods may also be devised in order to achieve and serve the purpose of the invention. Accordingly, it should be understood that there may be other embodiments which fall within the spirit and scope of the invention as defined by the specification hereto.

General Methods of Preparation

The compounds of the present invention may be prepared by the following processes. Unless otherwise indicated, the variables (e.g. X, Y, Z, G, $R^a$, $R^b$, $R^c$, $R^d$, $R^e$, $R^f$, $R^1$, $R^2$, $R^3$ and $R^4$) when used in the below formulae are to be understood to represent those groups described above in relation to compounds of formula (I), (IA), and (IB). These methods can similarly be applied to other compounds of formulas as provided herein above with or without modification.

Scheme 1

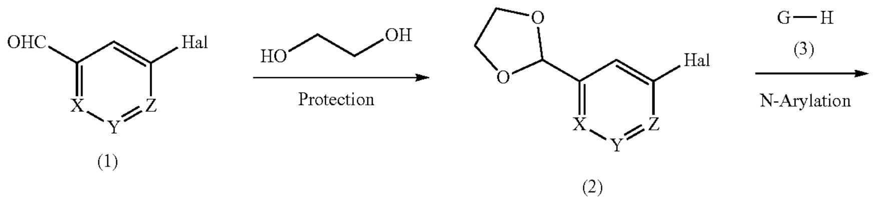

-continued

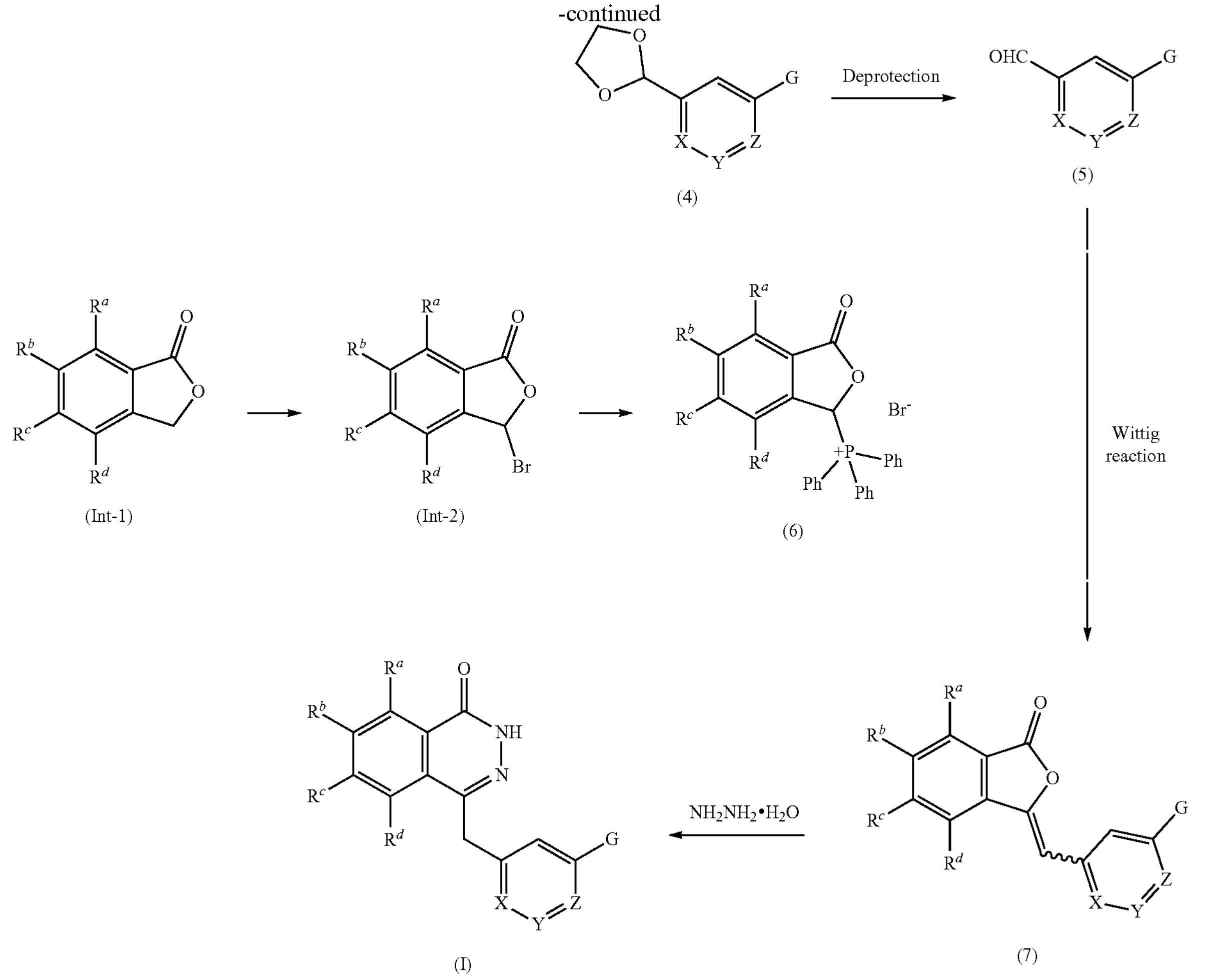

(4) (5) (Int-1) (Int-2) (6) (I) (7)

A compound of formula (1) which is an aldehyde can be protected using a protecting group (PG), such as by reaction with 1,2-ethanediol, to obtain acetal (2). A compound of formula (3) (G-H) can be N-arylated with acetal (2) using Buchwald type reaction conditions to obtain a compound of formula (4). The acetal of formula (4) can be deprotected to afford the aldehyde of formula (5) using suitable acids such as hydrochloric acid. The aldehyde of formula (5) can be reacted with a Wittig salt of formula (6) to give the olefin of formula (7). The olefin of formula (7) can be reacted with hydrazine hydrate to form the compound of formula (I). The compound of formula (6) can be prepared by brominating the compound (Int-1), such as with N-bromosuccinimide, to form compound (Int-2) and reacting it with triphenylphosphine. The compound formula (I) can be converted to a salt by methods known in the art. This scheme is illustrated below as Scheme 1A, Illustration 1, and Illustration 2.

Scheme 1A

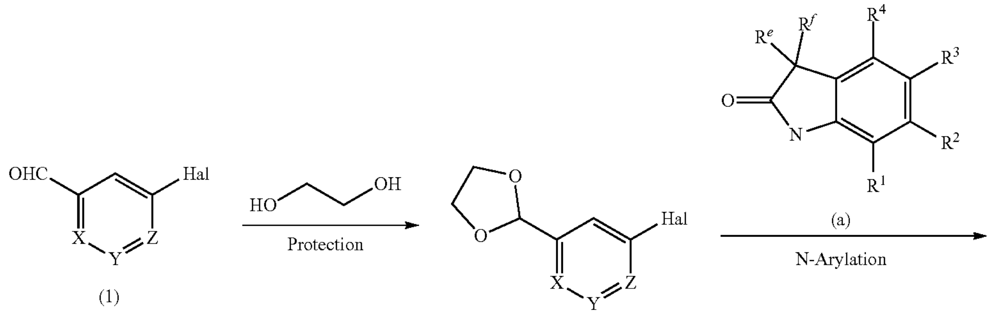

(1) (2) (a)

-continued

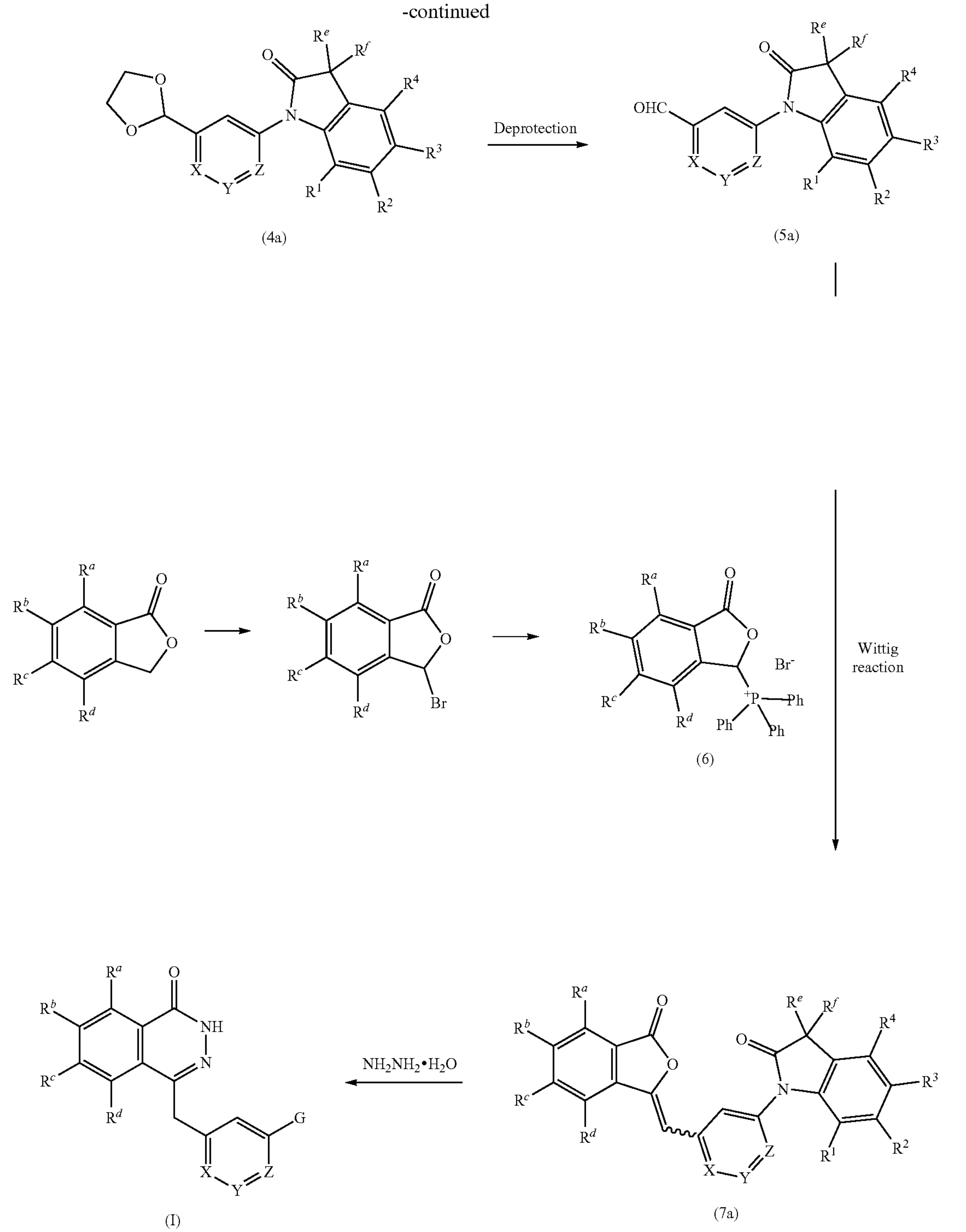

(4a) (5a) (6) (7a) (I)

In Scheme 1A, a compound of formula (1) (wherein X, Y, Z are independently selected from CH or N) which is an aldehyde can be protected, such as by reaction with 1,2-ethanediol, to obtain acetal (2). A compound of formula (a) (wherein $R^e$ is selected from hydrogen, methyl, ethyl or trifluoromethyl, $R^f$ is selected from hydroxy, acetyloxy or methoxy, and $R^1$—$R^4$ are defined as described herein) can be N-arylated with acetal (2) using Buchwald type reaction conditions to obtain a compound of formula (4a). The acetal of formula (4a) can be deprotected to afford the aldehyde of formula (5a) using suitable acids such as hydrochloric acid. The aldehyde of formula (5a) can be reacted with a Wittig salt of formula (6) (wherein $R^a$, $R^b$, Rc and $R^d$ are independently selected from hydrogen or halogen) to give the olefin of formula (7a). The olefin of formula (7a) can react with hydrazine hydrate to form the compound of formula (I).

Similarly, a compound of formula (b), (c), (d) or (e) can be used instead of a compound of formula (a) in Scheme 1A to prepare compounds of Formula (I). This scheme is illustrated below as Illustration 1.

Illustration 1
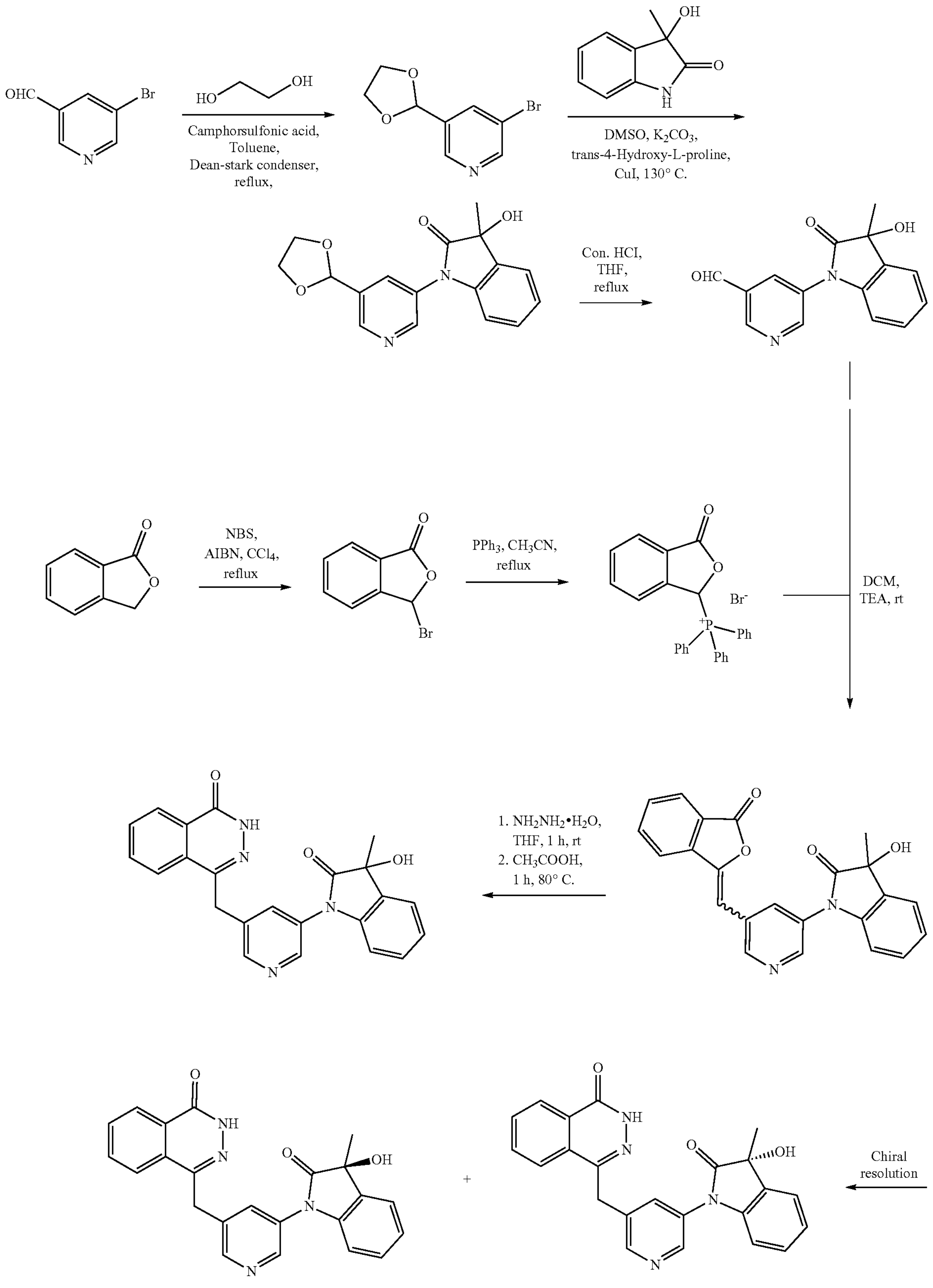

Illistration 2
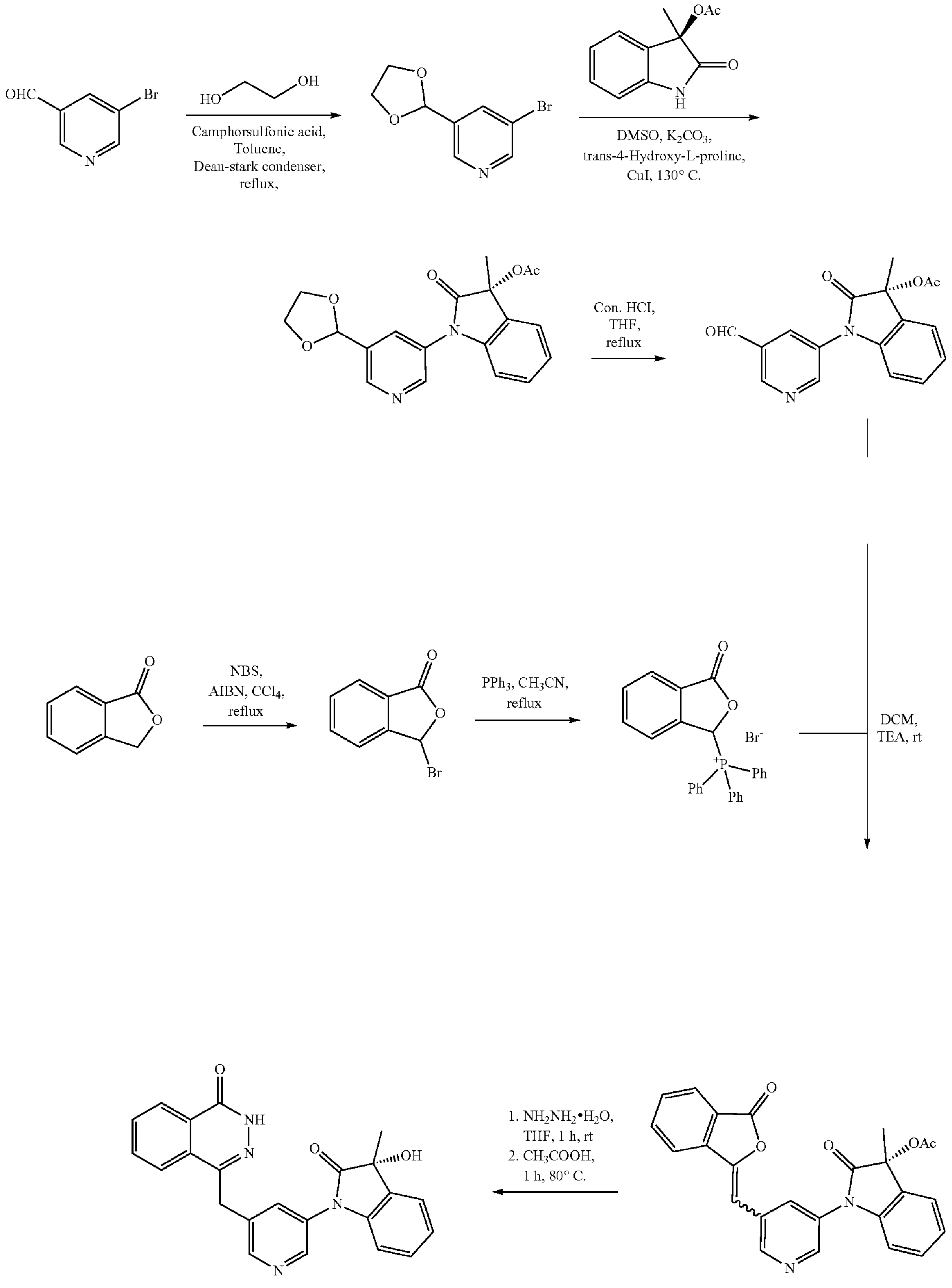

Similar methodologies with certain modifications as known to those skilled in the art can be used to synthesize compound of formula (I) wherein all the variable are to be understood to represent those groups described above using suitable intermediates and reagents.

Yet another method for preparing the compounds of formula (I) is provided below in Scheme 2.

Scheme 2

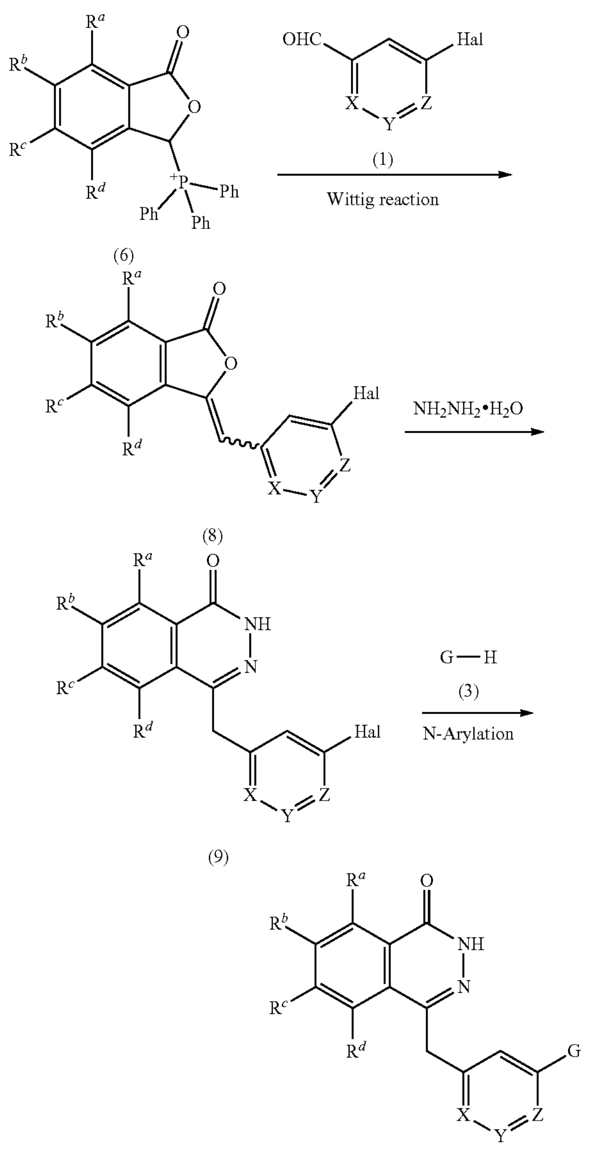

(6) (8) (9) (I)

A compound of formula (1) can be reacted with a Wittig salt of formula (6) to give an olefin of formula (8). The olefin of formula (8) can be reacted with hydrazine hydrate to form the compound of formula (9), which can be subjected to N-arylation with a compound of formula (3) using Buchwald type reaction conditions to obtain a compound of formula (I). The compound formula (I) can be converted to a salt by methods known in the art.

Experimental Data

General Procedure-1 for Buchwald coupling reaction: Aryl halide (1eq), Oxindoles (2-hydroxyindoles) and related derivates or NH containing heterocycles (1 eq), trans-4-Hydroxy-L-proline (0.4 eq) and potassium carbonate (1 eq) were dissolved in DMSO (6 Vols) and degassed with nitrogen for 15 mins. Copper (I) iodide (0.2 eq) was added to the above mixture and again degassed for 15 mins. After degassing, reaction mixture heated to 130° C. and stirred for 4 h at same temperature. After completion of the reaction, reaction mixture diluted with water and extracted with MeOH:DCM (1:9) to obtain crude. Crude was purified by column chromatography to obtain N-Arylated product.

General Procedure-2 for Wittig reaction: Aldehyde (1 eq.) and Wittig Salt (1 eq.) were dissolved in Dichloromethane (100 Vols). Triethyl amine (2 eq.) was added to this mixture. Reaction mixture was stirred for 1 hr at room temperature. After completion of the reaction, reaction mixture diluted with water and separated the organic layer. Evaporation of organic layer on rotavapor afforded the Olefin, which was used in the next step without further purification.

General Procedure-3 for Phthalazinone formation: Olefin (1 eq.) and Hydrazine hydrate (1.2 eq.) were dissolved in THF (15 Vols). This mixture was stirred at rt for 1 h. After 1 h acetic acid (0.5 eq) was added and reaction mixture refluxed at 80° C. Progress of the reaction was monitored by TLC. After completion of the reaction, reaction mixture diluted with water and extracted with MeOH and DCM (1:9) mixture. Organic layer dried on anhydrous $Na_2SO_4$ and distilled to obtain a crude. Crude was purified by combi-flash or column chromatography using suitable mixture of MeOH and DCM.

General Procedure-4 for chiral separation of Racemic intermediates and Examples: Chiral Intermediates and Examples which were synthetically obtained in racemic forms can be separated into the pure enantiomers by using following preparative chiral separation by suitable HPLC methods. By using the below methods Examples 2, 3, 7, 8, 11, 12, 14, 15, 19, 20, 22 and 23 can be resolved into pure enantiomers.

Preparative Method-1:
- Column: CHIRALCEL OJ-H, (250×30) mm, 5 micron
- Mobile Phase: Hexanes/EtOH/MeOH/DEA/80/10/10/0.1 v/v/v/v
- Flow rate: 40 mL/min
- Detection: UV 210 nm
- Temperature: 25° C.
- Feed Conc.: 10 mg/mL
- Inj vol: 5 mL (on column: 50 mg)
- Runtime: 30 min
- Cycle time: 12 min Preparative Method-2:
- Column: CHIRALCEL OX—H, (250×30) mm, 5 micron
- Mobile Phase: $CO_2$/Co-Solvent 65/35
- Co-Solvent: MeOH/ACN/DEA 50/50/0.3v/v/v
- Flow rate: 120 mL/min
- Detection: UV 260 nm
- Temperature: 25° C.
- Feed Conc.: 20 mg/mL
- Inj vol: 5 mL (on column: 100 mg)
- Run time: 20 min
- Cycle time: 15 min Preparative Method-3:
- Column: CHIRALCEL OX—H, (250×30) mm, 5 micron
- Mobile Phase: $CO_2$/Co-Solvent 65/35
- Co-Solvent: MeOH/ACN 50/50
- Flow rate: 120 mL/min
- Detection: UV 260 nm
- Temperature: 25° C.
- Feed Conc.: 20 mg/mL Inj vol: 5 mL (on column: 100 mg)
Run time: 20 min
Cycle time: 15 min Preparative Method-4:
Column: CHIRALPAK AS-H, (250×21) mm, 5 micron
Mobile Phase: MeOH/ACN 10/90
Co-Solvent: MeOH/ACN 50/50
Flow rate: 20 mL/min
Detection: UV 300 nm
Temperature: 25° C.
Feed Conc.: 40 mg/mL
Inj vol: 4 mL (on column: 160 mg)
Run time: 10 min
Cycle time: 7 min Preparative Method-5:
Column: CHIRALPAK IG, (250×30) mm, 5 micron
Mobile Phase: ACN/MeOH/DEA (70/30/0.1 v/v/v)
Flow rate: 40 mL/min
Detection: UV 245 nm
Temperature: 25° C.
Feed Conc.: 10 mg/mL
Inj vol: 5 mL (on column: 50 mg)
Run time: 15 min
Concentration: 30° C.

Analytical Method 1:
Column: CHIRALCEL OX-3R (150×4.6) mm, 3.0 μm
Mobile phase: 30 mM Ammonium acetate in [Water/ACN/MeOH (40/10/50, v/v/v)]
Flow rate: 1.0 mL/min
Detection: UV 210 nm
Temperature: 40° C.

Analytical Method 2:
Column: CHIRALCEL AS-H (250×4.6) mm, 3.0 μm
Mobile phase: ACN/MeOH (90/10 v/v)
Flow rate: 1.0 mL/min
Detection: UV 247 nm
Temperature: 25° C.

Analytical Method 3:
Column: CHIRALCEL IG (250×4.6) mm, 5.0 μm
Mobile phase: ACN/MeOH/DEA (70/30/0.1 v/v/v)
Flow rate: 1.0 mL/min
Detection: UV 254 nm
Temperature: 25° C.

Intermediate 1:2-(4-Fluoro-3-iodophenyl)-1,3-dioxolane

4-Fluoro-3-iodobenzaldehyde (5 g, 19.99 mmol) was suspended in toluene (22 ml). To this mixture camphorsulphonic acid (23 mg, 0.1 mmol) and ethylene glycol (1.61 ml, 29.99 mmol) were added and refluxed for 4 hrs under a dean-stark condenser. After completion of the reaction, reaction mixture diluted with ethyl acetate (200 ml) and washed with saturated aqueous sodium bicarbonate solution. Organic layer dried on anhydrous $Na_2SO_4$. Organic layer distilled out under vacuum to obtain the titled compound (5.88 g) as a brown liquid. $^1$H-NMR (δ ppm, $CDCl_3$, 400 MHz): 7.88 (d, J 4.2, 1H), 7.42 (t, J 6, 1H), 7.05 (t, J 8.1, 1H), 5.74 (s, 1H), 4.17-3.98 (m, 4H).

Intermediate 2:3-Bromoisobenzofuran-1 (3H)-one

Phthalide (100 g, 0.745 mol) suspended in Carbon tetrachloride (500 ml) and added N-Bromosuccinimide (146 g, 0.82 mol) to this mixture. Reaction mixture heated to 85° C. and Azobisisobutyronitrile AIBN(6.12 g, 37.2 mmol) was added to the reaction mixture lot-wise (10 lots). After 4 h reaction mixture cooled to room temperature. Reaction mixture quenched with water and separated organic layer. Aqueous layer extracted with DCM and combined organic layers dried on anhydrous $Na_2SO_4$. Organic layer evaporated on rotavapor to obtain crude solid. Crude solid was suspended in Petroleum ether (300 ml) and stirred for 15 mins to obtain a solid. Filtered the solid and washed the solid with Petroleum ether (100 ml). Solid dried under vacuum for 1 hr to obtain the titled compound as a brown solid (145 G). Yield: 91.39%, $^1$H-NMR (δ ppm, $CDCl_3$, 400 MHz): 7.94 (d, J 8, 1H), 7.79 (t, J 7.6, 1H), 7.64 (d, J 7.6, 2H), 7.40 (s, 1H).

Intermediate 3: (3-Oxo-1,3-dihydroisobenzofuran-1-yl)triphenylphosphonium bromide Intermediate 2 (50 g, 0.234 mols) suspended in acetonitrile (180 ml) and added triphenylphosphine (61.54 g, 0.234 mols). This mixture was heated to 90° C. and stirred for 2.5 h. Reaction mixture cooled to room to temperature to obtain a solid. Solid was filtered and washed with diethyl ether (125 ml). Solid dried under vacuum for 30 mins to obtain the titled compound as a white solid (94 g). Yield: 84%, $^1$H-NMR (δ ppm, DMSO-$d_6$, 400 MHz): 8.61 (s, 1H), 8.00-7.93 (m, 3H), 7.86-7.70 (m, 15H), 6.95 (d, J 7.6, 1H).

Intermediate 4:3-Bromo-5-(1,3-dioxolan-2-yl)pyridine

5-Bromonicotinaldehyde (35 g, 0.19 mol) was suspended in toluene (500 ml) and camphorsulphonic acid (350 mg, 0.15 mmol) and ethylene glycol (15.23 ml, 0.28 mol) were added. This mixture was refluxed for 4 h under a dean-stark condenser. After completion of the reaction, reaction mixture diluted with ethyl acetate (200 ml) and washed with saturated aqueous sodium bicarbonate solution. Organic layer dried on anhydrous $Na_2SO_4$. Organic layer distilled out under vacuum to obtain the titled compound (5.88 g) as a brown liquid. Yield: 100%, $^1$H-NMR (δ ppm, $CDCl_3$, 400 MHz): 7.88 (d, J 4.2, 1H), 7.42 (t, J 6, 1H), 7.05 (t, J 8.1, 1H), 5.74 (s, 1H), 4.17-3.98 (m, 4H).

Intermediate 5:3-Hydroxy-3-methylindolin-2-one

Isatin (3 g, 20.39 mmol) was dissolved in THF (50 ml) under nitrogen atmosphere and cooled to −10° C. 3M Methyl magnesium chloride in THF (20.39 ml. 61.1 mmol) was added to the above mixture drop-wise and stirred the reaction mixture at −10° C. for 2 h. After 2h, reaction mixture quenched with aq. Ammonium chloride solution and extracted with MeOH and DCM (1:9) (3*150 ml). Combined organic layers were washed with water (100 ml) and dried on anhydrous $Na_2SO_4$. Organic layer distilled to obtain a crude. Crude was suspended in Diethyl ether (50 ml) and stirred for 15 mins to obtain a solid. Solid was filtered and washed the solid with diethyl ether (10 ml). Solid dried under vacuum for 30 mins to obtain the titled compound (2.35 g) as a yellow solid. Yield: 71%, $^1$H-NMR (δ ppm, DMSO-$d_6$, 400 MHz): 10.18 (s, 1H), 7.26 (d, J 7.6, 1H), 7.17 (t, J 7.6, 1H), 6.94 (t, J 7.6, 1H), 6.78 (d, J 7.6, 1H), 5.82 (s, 1H), 1.33 (s, 3H). MS (m/z): 162.2 ($[M-H]^-$). By following one of the Preparative methods indicated in General procedure 4, racemic 3-Hydroxy-3-methylindolin-2-one resolved into the (+) and (−) enantiomers and used as on when needed.

(R)-(+)-3-Hydroxy-3-methylindolin-2-one $^1$H-NMR (δ ppm, DMSO-$d_6$, 400 MHz): 10.19 (s, 1H), 7.26 (d, J 7.6, 1H), 7.17 (t, J 7.6, 1H), 6.94 (t, J 7.6, 1H), 6.78 (d, J 7.6, 1H), 5.82 (s, 1H), 1.33 (s, 3H). $[\alpha]_D$25: +45.90° (MeOH; c 1.0)

(S)-(−)-3-hydroxy-3-methylindolin-2-one $^1$H-NMR (δ ppm, DMSO-$d_6$, 400 MHz): 10.19 (s, 1H), 7.26 (d, J 7.6, 1H), 7.17 (t, J 7.6, 1H), 6.94 (t, J 7.6, 1H), 6.78 (d, J 7.6, 1H), 5.83 (s, 1H), 1.33 (s, 3H). $[\alpha]_D$25: −45.94° (MeOH; c 1.0).

Intermediate 6:1-(5-(1,3-Dioxolan-2-yl)-2-fluorophenyl)-3-hydroxy-3-methylindolin-2-one Following the general procedure 1, the titled compound was synthesized from Intermediate 1 (1.63 g, 5.54 mmol) and Intermediate 5 (0.9 g, 5.54 mmol). Crude product obtained was purified by combi-flash using MeOH and DCM (2.1:97.9) as eluent. Combined pure fractions from combi-flash were distilled to obtain the titled compound as a brown gel (740 mg). Yield: 40.88%, $^1$H-NMR (δ ppm, DMSO-$d_6$, 400 MHz): 7.66-7.58 (m, 1.5 H), 7.56-7.41 (m, 2.5 H) 7.28-7.21 (m, 1H), 7.16-7.08 (m, 1H), 6.55 (t, J 8.2, 1H) 6.28 (s, 0.45 H), 6.16 (s, 0.55 H) 5.81 (s, 0.55 H), 5.78 (s, 0.45 H), 4.10-4.03 (m, 2H), 3.98-3.93 (m, 2H), 1.53 (s, 1.35 H), 1.49 (s, 1.65 H).

Intermediate 7:4-Fluoro-3-(3-hydroxy-3-methyl-2-oxoindolin-1-yl)benzaldehyde Intermediate 6 (700 mg, 2.13 mmol) was dissolved in THF (10 ml) and added 6N Hydrochloric acid (3 ml). This mixture was stirred at room temperature for 1 h. After 1 h, reaction mass cooled to 0° C. and pH of the reaction mixture adjusted to ~7 using saturated aqueous sodium bicarbonate solution. Aqueous reaction mixture extracted with MeOH and DCM (1:9) (2*100 ml). Combined organic layers dried on anhydrous $Na_2SO_4$ and evaporated to obtain titled compound as a brown gel (605 mg). Yield: 100%, $^1$H-NMR (δ ppm, DMSO-$d_6$, 400 MHz): 10.04 (s, 0.55 H), 10.01 (s, 0.45 H), 8.19-8.02 (m, 2H), 7.74 (t, J 9.5, 1H), 7.50-7.43 (m, 1H), 7.30-7.22 (m, 1H), 7.18-7.10 (m, 1H), 6.70-6.62 (m, 1H), 6.32 (s, 0.45 H), 6.21 (s, 0.55 H), 1.55 (s, 1.35 H), 1.50 (s, 1.65 H).

Intermediate 8:1-(2-Fluoro-5-((3-oxoisobenzofuran-1 (3H)-ylidene)methyl)phenyl)-3-hydroxy-3-methylindolin-2-one Following the general procedure 2, the titled compound was synthesized from Intermediate 7 (600 mg, 2.1 mmol) and Intermediate 3 (1.79 g, 3.8 mmol) as a pale-yellow gel (840 mg). Yield: 100%. Compound was taken to the next step without any characterization.

Intermediate 9:1-(5-(1,3-Dioxolan-2-yl)pyridin-3-yl)-3-hydroxy-3-methylindolin-2-one Following the general procedure 1, the titled compound was synthesized from Intermediate 4 (2 g, 8.68 mmol) and Intermediate 5 (1.4 g, 8.68 mmol). Crude product obtained was purified by combi-flash using MeOH and DCM (3.1:96.9) as eluent. Combined pure fractions from combi-flash were distilled to obtain the titled compound as a pale-yellow gel (865 mg). Yield: 31.9%, $^1$H-NMR (δ ppm, DMSO-$d_6$, 400 MHz): 8.71 (bs, 2H), 7.92 (s, 1H), 7.46 (d, J 7.3, 1H), 7.27 (t, J 7.6, 1H), 7.13 (t, J 7.4, 1H), 6.75 (d, J 7.8, 1H), 6.15 (s, 1H), 5.93 (s, 1H), 4.15-4.09 (m, 2H), 4.02-3.95 (m, 2H), 1.52 (s, 3H). MS (m/z): 312.8 ($[M+H]^+$).

Intermediate 10:5-(3-Hydroxy-3-methyl-2-oxoindolin-1-yl)nicotinaldehyde

Intermediate 9 (850 mg, 2.72 mmol) was dissolved in THF (10 ml) and added Concentrated Hydrochloric acid (2.5 ml). This mixture was refluxed at 70° C. for 1 h. After 1 h, reaction mixture cooled to 0° C. and pH of the reaction mixture adjusted to ~7 using saturated aqueous sodium bicarbonate solution. Aqueous reaction mixture extracted with MeOH and DCM (1:9) (2*100 ml). Combined organic layers dried on anhydrous $Na_2SO_4$ and evaporated to obtain the titled compound as a pale-yellow gel (729 mg). Yield: 100%, $^1$H-NMR (δ ppm, DMSO-$d_6$, 400 MHz): 10.18 (s, 1H), 9.13 (d, J 1.2, 1H), 8.96 (d, J 2.4, 1H), 8.34 (t, J 2, 1H), 7.48 (d, J 7.2, 1H), 7.28 (td, J 8, 1.2, 1H), 7.16 (t, J 7.2, 1H), 6.89 (d, J 8, 1H), 6.19 (s, 1H), 1.53 (s, 3H). MS (m/z): 268.8 ($[M+H]^+$).

Intermediate 11:3-Hydroxy-3-methyl-1-(5-((3-oxoisobenzofuran-1 (3H)-ylidene)methyl)pyridin-3-yl)indolin-2-one Following the general procedure 2, the titled compound was synthesized from Intermediate 10 (720 mg, 2.7 mmol) and Intermediate 3 (2.29 g, 4.8 mmol) as a yellow gel (1.03 g). Yield: 100%. MS (m/z): 384.8 ($[M+H]^+$).

Intermediate 12:2-Bromo-4-(1,3-dioxolan-2-yl)pyridine

2-Bromoisonicotinaldehyde (5 g, 26.9 mmol) was suspended in toluene (40 ml). To this mixture camphorsulphonic acid (20 mg, 0.09 mmol) and ethylene glycol (2.25 ml, 0.28 mol) were added and refluxed for 15 h under a dean-stark condenser. After completion of the reaction, reaction mixture diluted with ethyl acetate (200 ml) and washed with saturated aqueous sodium bicarbonate solution. Organic layer dried on anhydrous $Na_2SO_4$ and distilled to obtain the titled compound (6 g) as a brown liquid. Yield: 97% $^1$H-NMR (δ ppm, $CDCl_3$, 400 MHz): 8.39 (d, J 4.9, 1H), 7.60 (s, 1H), 7.35 (d, J 4.9, 1H), 5.80 (s, 1H), 4.06 (s, 4H).

Intermediate 13:1-(4-(1,3-Dioxolan-2-yl)pyridin-2-yl)-3-hydroxy-3-methylindolin-2-one Following the general procedure 1, the titled compound was synthesized from Intermediate 12 (4.3 g, 18.69 mmol) and Intermediate 5 (3 g, 18.69 mmol). Crude product obtained after work up was used in the next step without further purification (900 mg). Yield: 17%. Compound was taken to the next step without any characterization.

Intermediate 14:2-(3-Hydroxy-3-methyl-2-oxoindolin-1-yl)isonicotinaldehyde

Intermediate 13 (900 mg, 2.88 mmol) was dissolved in THF (10 ml) and added Concentrated Hydrochloric acid (0.9 ml). This mixture was refluxed at 80° C. for 1 h. After 1 h, reaction mass cooled to 0° C. and pH of the reaction mixture adjusted to ~7 using saturated aqueous sodium bicarbonate solution. Aqueous reaction mixture extracted with MeOH and DCM (1:9) (2*100 ml). Organic layer dried on anhydrous $Na_2SO_4$ and evaporated on rotavapor to obtain titled compound as a pale-yellow gel (700 mg). Yield: 100%. Compound was taken to the next step without any characterization.

Intermediate 15:3-Hydroxy-3-methyl-1-(4-((3-oxoisobenzofuran-1 (3H)-ylidene)methyl)pyridin-2-yl)indolin-2-one Following the general procedure 2, the titled compound was synthesized from Intermediate 14 (350 mg, 1.30 mmol) and Intermediate 3 (1.1 g, 2.35 mmol) as a yellow gel (500 mg). Yield: 100%. Compound was taken to the next step without any characterization. Intermediate 16:3-Ethyl-3-hydroxyindolin-2-one This compound was prepared by the following procedure. Magnesium turnings (2.48 g, 0.101 mol) and Iodine (2 mg) were taken in diethyl ether (50 ml) under nitrogen atmosphere. To this mixture Bromoethane (7.57 ml, 0.101 mol) was added dropwise for 20 mins and stirred the reaction mixture for 2 hrs at room temperature to obtain ethyl magnesium bromide.

Isatin (5 g, 0.033 mol) was dissolved in THF (50 ml) under nitrogen atmosphere and cooled to −15° C. Ethyl magnesium bromide in diethyl ether from above reaction was added to the reaction mixture drop-wise at −15° C. and stirred for 2 h at same temperature. After 2h, reaction mixture quenched with aq. Ammonium chloride solution (200 ml) and extracted with MeOH and DCM (1:9) (3*100 ml). Combined organic layers dried on anhydrous $Na_2SO_4$ and distilled to obtain a crude. Crude was purified by combi-flash using MeOH and DCM (3:97) as eluent. Pure fractions from combi-flash were distilled to obtain the titled compound as a brown solid (1.24 g). Yield: 21%, $^1H$-NMR (δ ppm, DMSO-$d_6$, 400 MHz): 10.19 (s, 1H), 7.22 (d, J 7.31, 1H), 7.18 (t, J 7.7, 1H), 6.95 (t, J 7.4, 1H), 6.78 (d, J 7.7, 1H), 5.79 (s, 1H), 1.75 (m, 2H), 0.59 (t, J 7.4, 3H). MS (m/z): 176.1 ([M−H]$^-$).

Intermediate 17:1-(5-(1,3-Dioxolan-2-yl)pyridin-3-yl)-3-ethyl-3-hydroxyindolin-2-one Following the general procedure 1, the titled compound was synthesized from Intermediate 4 (1.43 g, 6.2 mmol) and Intermediate 16 (1.1 g, 6.2 mmol). Crude product obtained was purified by combi-flash using MeOH and DCM (2.5:97.5) as eluent. Combined pure fractions from combi-flash were distilled to obtain the titled compound as a pale-yellow gel (800 mg). Yield: 39%, $^1H$-NMR (δ ppm, DMSO-$d_6$, 400 MHz): 8.71 (s, 1H), 8.67 (s, 1H), 7.88 (d, J 1.9, 1H), 7.42 9d, J 7.3, 1H), 7.28 (td, J 7.1, 1, 1H), 7.15 (t, J 7.4, 1H), 6.76 (d, J 7.8, 1H), 6.15 (s, 1H), 5.93 (s, 1H), 4.12-4.06 (m, 2H), 4.01-3.96 (m, 2H), 1.97-1.88 (m, 2H), 0.72 (t, J 7.4, 3H).

Intermediate 18:5-(3-Ethyl-3-hydroxy-2-oxoindolin-1-yl)nicotinaldehyde

Intermediate 17 (800 mg, 2.45 mmol) was dissolved in THF (20 ml) and added Concentrated Hydrochloric acid (2 ml). This mixture was refluxed at 80° C. for 2 h. After 2 h, reaction mass cooled to 0° C. and pH of the reaction mixture adjusted to ~7 using saturated aqueous sodium bicarbonate solution. Aqueous reaction mixture extracted with MeOH and DCM (1:9) (3*50 ml). Combined organic layers dried on anhydrous $Na_2SO_4$ and evaporated to obtain the titled compound as a brown liquid (700 mg). Yield: 100%. Compound was taken to the next step without any characterization.

Intermediate 19:3-Ethyl-3-hydroxy-1-(5-((3-oxoisobenzofuran-1 (3H)-ylidene)methyl)pyridin-3-yl)indolin-2-one Following the general procedure 2, the titled compound was synthesized from Intermediate 18 (700 mg, 2.48 mmol) and Intermediate 3 (2.12 g, 4.46 mmol) as a pale-yellow gel (987 mg). Yield: 100%. Compound was taken to the next step without any characterization. Intermediate 20: (2-Bromo-4-fluorophenyl)methanol This compound was prepared by the following procedure. 2-Bromo-4-fluorobenzaldehyde (12 g, 59.11 mmol) was suspended in MeOH (120 ml) and cooled to 0° C. Sodium borohydride (4.47 g, 118.2 mmol) was added lot-wise to the above mixture and stirred for 1 h at 0° C. After 1 h reaction mixture quenched with aqueous saturated ammonium chloride solution (150 ml). Distilled out the reaction mixture to remove MeOH and aqueous layer extracted with ethyl acetate (2*200 ml). Combined ethyl acetate layers were dried on anhydrous $Na_2SO_4$ and evaporated to obtain the titled compound as an Off-White solid (11.6 g). Yield 95.71%, $^1H$-NMR (δ ppm, $CDCl_3$, 400 MHz): 7.46 (dd, J 8.4, 6.1, 1H), 7.31 (dd, J 8.2,2.5, 1H), 7.05 (dd, J 8.3, 5.9, 1H), 4.72 (d, J 5.1, 2H), 1.96 (t, J 5.7, 1H).

Intermediate 21:6-Fluoroisobenzofuran-1 (3H)-one

This compound was prepared by the following procedure. Intermediate 20 (11.5 g, 56.1 mmol) was dissolved in DMF (50 ml) under nitrogen atmosphere. To this copper cyanide (10.04 g, 112.2 mmol) was added and heated the reaction mixture to 180° C. for 2.5 h. After 2.5 h, reaction mixture cooled to 100° C. and water was added to the reaction mixture. Continued the reaction at 100° C. for 18 h. After 18 h, reaction mixture cooled to room temperature and diluted with ethyl acetate (250 ml). Reaction mixture filtered on a plug of celite and celite bed washed with ethyl acetate (100 ml). Combined ethyl acetate filtrates were washed with water (200 ml), brine solution (200 ml) and saturated aqueous lithium chloride solution (200 ml). Organic layer dried on anhydrous $Na_2SO_4$ and evaporated to obtain a crude. Crude was purified by combi-flash using ethyl acetate and petroleum ether (16:84) as eluent. Combined pure fractions from column were evaporated to obtain the titled compound as a brown solid (3 g). Yield: 36%, $^1H$-NMR (δ ppm, $CDCl_3$, 400 MHz): 7.59 (dd, J 7.2, 2, 1H), 7.48 (dd, J 8.3, 4.3, 1H), 7.41 (td, J 8.5, 2.2, 1H), 5.31 (s, 2H).

Intermediate 22:3-Bromo-6-fluoroisobenzofuran-1 (3H)-one

Intermediate 21 (1.5 g, 9.86 mmol) suspended in Carbon tetrachloride (20 ml) and added N-Bromosuccinimide (1.93 g, 10.84 mmol). Reaction mixture heated to 85° C. and Azobisisobutyronitrile AIBN(80 mg, 0.49 mmol) was added to the reaction mixture lot-wise (2 lots). After 4 h reaction mixture cooled to room temperature. Reaction mixture quenched with water and separated organic layer. Aqueous layer extracted with DCM and combined organic layers dried on anhydrous $Na_2SO_4$. Organic layer evaporated to obtain the titled compound as a brown gel (2.27 g). Yield:

100%, $^1$H-NMR (δ ppm, $CDCl_3$, 400 MHz): 7.62 (dd, J 8.4, 4.2, 1H), 7.57 (dd, J 6.8, 2.2, 1H), 7.50 (td, J 8.5, 2.3, 1H), 7.38 (s, 1H).

Intermediate 23: (5-Fluoro-3-oxo-1,3-dihydroisobenzofuran-1-yl)triphenylphosphonium bromide Intermediate 22 (5 g, 21.6 mmol) suspended in acetonitrile (20 ml) and added triphenylphosphine (5.67 g, 21.6 mmol). This mixture was heated to 90° C. and stirred for 2.5 h at the same temperature. Reaction mixture cooled to room temperature to obtain a solid. Solid was filtered and washed with diethyl ether (20 ml). Solid dried under vacuum for 1 hr to obtain a crude (8.2 g). Crude compound was mixed with ethanol (25 ml) and refluxed for 1 h at 90° C. After one hour, stirred the heterogeneous mixture at room temperature for 15 h. Filtered the solid and solid washed with ethanol (5 ml). Solid dried under vacuum to obtain the titled compound (6 g) as an off-white solid. Yield: 56%, $^1$H-NMR (δ ppm, DMSO-$d_6$, 400 MHz): 8.57 (s, 1H), 8.02-7.94 (m, 3H), 7.84-7.67 (m, 14H), 7.00-6.94 (m, 1H).

Intermediate 24:3-Hydroxy-3-methyl-1-(5-((3-oxoisobenzofuran-1 (3H)-ylidene)methyl)pyridin-3-yl)indolin-2-one Following the general procedure 2, the titled compound was synthesized from Intermediate 10 (450 mg, 1.68 mmol) and Intermediate 23 (1.48 g, 3.01 mmol) as a pale-yellow gel (674 mg). Yield: 100%. Compound was taken to the next step without any characterization.

Intermediate 25:5-Fluoroisobenzofuran-1 (3H)-one

This compound was prepared by the following procedure. (2-Bromo-5-fluorophenyl)methanol (10 g, 48.8 mmol) was dissolved in DMF (50 ml) under nitrogen atmosphere. To this copper cyanide (8.74 g, 97.54 mmol) was added and heated the reaction mixture to 180° C. for 3 h. After 3 hr, reaction mixture cooled to 100° C. and water was added to the reaction mixture. Continued the reaction at 100° C. for 18 h. After 18 h, reaction mixture cooled to room temperature and diluted with ethyl acetate (250 ml). Reaction mixture filtered on a plug of celite and celite bed washed with ethyl acetate (100 ml). Combined ethyl acetate filtrates were washed with water (200 ml), brine solution (200 ml) and saturated aqueous lithium chloride solution (200 ml). Organic layer dried on anhydrous $Na_2SO_4$ and evaporated to obtain a crude. Crude was purified by combi-flash using ethyl acetate and petroleum ether (16:84) as eluent. Combined pure fractions from combi-flash were evaporated to obtain the titled compound as a brown solid (4.2 g). Yield: 57%, $^1$H-NMR (δ ppm, $CDCl_3$, 400 MHz): 7.93 (dd, J 8.5, 5, 1H), 7.24 (td, J 8.4, 1.8, 1H), 7.18 (dd, J 7.8, 1.4, 1H), 5.30 (s, 2H).

Intermediate 26:3-Bromo-5-fluoroisobenzofuran-1 (3H)-one

Intermediate 25 (3 g, 19.72 mmol) suspended in Carbon tetrachloride (40 ml) and added N-Bromosuccinimide (3.86 g, 21.69 mmol). Reaction mixture heated to 85° C. and Azobisisobutyronitrile AIBN(161 mg, 0.98 mmol) was added to the reaction mixture lot-wise (3 lots). After 4 h reaction mixture cooled to room temperature. Reaction mixture quenched with water and separated organic layer. Aqueous layer extracted with DCM and combined organic layers dried on anhydrous $Na_2SO_4$. Organic layer evaporated on rotavapor to obtain crude. Crude was purified by combi-flash using Ethyl acetate and petroleum ether (11:89) as eluent. Combined pure fractions from combi-flash were distilled to obtain the titled compound as a brown liquid (3.96 g). Yield: 87%, $^1$H-NMR (δ ppm, $CDCl_3$, 400 MHz): 7.94 (dd, J 8.3, 4.7, 1H), 7.38-7.29 (m, 3H).

Intermediate 27: (6-Fluoro-3-oxo-1,3-dihydroisobenzofuran-1-yl)triphenylphosphonium bromide Intermediate 26 (3.46 g, 14.98 mmols) was suspended in acetonitrile (10 ml) and triphenylphosphine (3.92 g, 14.98 mmols) was added. This mixture was heated to 90° C. and stirred for 2.5 h at the same temperature. Reaction mixture cooled to room to temperature to obtain a solid. Solid was filtered and washed with diethyl ether (50 ml). Solid dried under vacuum for 1 h to obtain a crude (6.2 g). Crude compound was suspended in ethanol (30 ml) and refluxed for 1 h at 90° C. After 1 h, the heterogeneous mixture stirred at room temperature for 18 h. Filtered the solid and solid was washed with ethanol (5 ml). Solid dried under vacuum to obtain the titled compound (2.7 g) as an off-white solid. Yield: 37%, $^1$H-NMR (δ ppm, DMSO-$d_6$, 400 MHz): 8.58 (s, 1H), 8.02-7.90 (m, 4H), 7.77-7.65 (m, 12H), 7.61 (t, J 8.8, 1H), 6.65 (d, J 7.9, 1H).

Intermediate 28:1-(5-((6-Fluoro-3-oxoisobenzofuran-1 (3H)-ylidene)methyl)pyridin-3-yl)-3-hydroxy-3-methylindolin-2-one Following the general procedure 2, the titled compound was synthesized from Intermediate 10 (450 mg, 1.68 mmol) and Intermediate 27 (1.48 g, 3.01 mmol) as a pale-yellow gel (674 mg). Yield: 100%. Compound was taken to the next step without any characterization.

Intermediate 29:5-Fluoro-3-hydroxy-3-methylindolin-2-one

5-Fluoroisatin (10 g, 60.56 mmol) was suspended in THF (150 ml) under nitrogen atmosphere and cooled to −10° C. 3M Methyl magnesium chloride in THF (60.56 ml. 181.69 mmol) was added to the above mixture drop-wise and stirred the reaction mixture at −10° C. for 3 h. After 3 h, reaction mixture quenched with aqueous ammonium chloride solution (250 ml) and extracted with ethyl acetate (2*300 ml). Combined organic layers were washed with water (300 ml) and dried on anhydrous $Na_2SO_4$. Organic layer distilled to obtain a crude (10 G). Crude was suspended in Diethyl ether (50 ml) and stirred for 15 mins to obtain a solid. Filtered the solid and solid was washed with diethyl ether (2*25 ml). Solid dried under vacuum for 30 mins to obtain the titled compound (8 g) as a brown solid. Yield: 72%, $^1$H-NMR (δ ppm, DMSO-$d_6$, 400 MHz): 10.22 (s, 1H), 7.15 (dd, J 8.1, 2.6, 1H), 7.04-6.98 (m, 1H), 6.78 (dd, J 8.4, 4.3, 1H), 5.95 (s, 1H), 1.34 (s, 3H).

Intermediate 30:1-(5-(1,3-Dioxolan-2-yl)pyridin-3-yl)-5-fluoro-3-hydroxy-3-methylindolin-2-one Following the general procedure 1, the titled compound was synthesized from Intermediate 4 (1.5 g, 6.51 mmol) and Intermediate 29 (1.18 g, 6.51 mmol). Crude product obtained was purified by combi-flash using MeOH and DCM (2.5:97.5) as eluent. Combined pure fractions from combi-flash were distilled to obtain the titled compound as a pale-yellow solid (650 mg). Yield: 30%, $^1$H-NMR (δ ppm, DMSO-$d_6$, 400 MHz): 8.76 (bs, 2H), 7.92 (s, 1H), 7.38 (dd, J 7.9, 2.5, 1H), 7.10 (td, J 9.2, 2.5, 1H), 6.77 (dd, J 8.6, 4.1, 1H), 6.27 (s, 1H), 5.93 (s, 1H), 4.12-4.05 (m, 2H), 4.01-3.95 (m, 2H), 1.53 (s, 3H).

Intermediate 31:5-(5-Fluoro-3-hydroxy-3-methyl-2-oxoindolin-1-yl)nicotinaldehyde Intermediate 30 (650 mg, 1.97 mmol) was dissolved in THF (20 ml) and added Concentrated Hydrochloric acid (2 ml). This mixture was refluxed at 80° C. for 2.5 h. After 2.5 h, reaction mass cooled to room temperature and pH of the reaction mixture adjusted to ~7 using saturated aqueous sodium bicarbonate solution. Aqueous reaction mixture extracted with MeOH and DCM (1:9) (3*50 ml). Combined organic layers dried on anhydrous $Na_2SO_4$ and evaporated to obtain the titled compound as a brown liquid (700 mg). Yield: 100%. Compound was taken to the next step without any characterization.

Intermediate 32:5-Fluoro-3-hydroxy-3-methyl-1-(5-((3-oxoisobenzofuran-1 (3H)-ylidene)methyl)pyridin-3-yl)indolin-2-one Following the general procedure 2, the titled compound was synthesized from Intermediate 31 (250 mg, 0.87 mmol) and Intermediate 3 (746 mg, 1.57 mmol) as a pale-yellow gel (351 mg). Yield: 100%. Compound was taken to the next step without any characterization. Intermediate 33:5-Fluoro-1-(5-((5-fluoro-3-oxoisobenzofuran-1 (3H)-ylidene)methyl) pyridin-3-yl)-3-hydroxy-3-methylindolin-2-one Following the general procedure 2, the titled compound was synthesized from Intermediate 31 (250 mg, 0.87 mmol) and Intermediate 23 (0.77 g, 1.57 mmol) as a pale-yellow gel (366 mg). Yield: 100%. Compound was taken to the next step without any characterization.

Intermediate 34:6-Fluoro-3-hydroxy-3-methylindolin-2-one

6-Fluoroisatin (5 g, 30.28 mmol) was suspended in THF (75 ml) under nitrogen atmosphere and cooled to −10° C. 3M Methyl magnesium chloride in THF (60.56 ml. 181.69 mmol) was added to the above mixture drop-wise and stirred the reaction mixture at −10° C. for 2 h. After 2 h, reaction mixture quenched with aq. Ammonium chloride solution (200 ml) and extracted with ethyl acetate (3*100 ml). Combined organic layers dried on anhydrous $Na_2SO_4$ and organic layer distilled to obtain a crude (6.2 G). Crude was suspended in Diethyl ether (100 ml) and stirred for 15 mins to obtain a solid. Filtered the solid and solid was washed with diethyl ether (50 ml). Solid dried under vacuum for 3 h to obtain the titled compound (4 g) as a brown solid. Yield: 73%, $^1$H-NMR (δ ppm, DMSO-$d_6$, 400 MHz): 10.34 (s, 1H), 7.28 (dd, J 8.1, 5.7, 1H), 6.73 (td, J 8.2, 2.4, 1H), 6.60 (dd, J 9.3, 2.3, 1H), 5.87 (s, 1H), 1.33 (s, 3H).

Intermediate 35:1-(5-(1,3-Dioxolan-2-yl)pyridin-3-yl)-6-fluoro-3-hydroxy-3-methylindolin-2-one Following the general procedure 1, the titled compound was synthesized from Intermediate 4 (1.5 g, 6.51 mmol) and Intermediate 34 (1.18 g, 6.51 mmol). Crude product obtained was purified by combi-flash using MeOH and DCM (2.5:97.5) as eluent. Combined pure fractions from combi-flash were distilled to obtain the titled compound as a pale-yellow solid (650 mg). Yield: 30%, $^1$H-NMR (δ ppm, DMSO-$d_6$, 400 MHz): 8.72 (s, 1H), 8.69 (s, 1H), 7.92 (s, 1H), 7.48 (dd, J 8.2, 5.6, 1H), 6.94 (td, J 8.4, 2.2, 1H), 6.63 (dd, J 9.4, 2.2, 1H), 6.18 (s, 1H), 5.94 (s, 1H), 4.11-4.05 (m, 2H), 4.01-3.95 (m, 2H), 1.52 (s, 3H).

Intermediate 36:5-(6-Fluoro-3-hydroxy-3-methyl-2-oxoindolin-1-yl)nicotinaldehyde Intermediate 35 (730 mg, 2.21 mmol) was dissolved in THF (20 ml) and added Concentrated Hydrochloric acid (3.5 ml). This mixture was refluxed at 80° C. for 3 h. After 3 h, reaction mixture cooled to 0° C. and pH of the reaction mixture adjusted to ~7 using saturated aqueous sodium bicarbonate solution. Aqueous reaction mixture extracted with MeOH and DCM (1:9) (2*200 ml). Combined organic layers dried on anhydrous $Na_2SO_4$ and evaporated to obtain the titled compound as a brown liquid (632 mg). Yield: 100%. Compound was taken to the next step without any characterization.

Intermediate 37:6-Fluoro-3-hydroxy-3-methyl-1-(5-((3-oxoisobenzofuran-1 (3H)-ylidene)methyl)pyridin-3-yl)indolin-2-one Following the general procedure 2, the titled compound was synthesized from Intermediate 36 (300 mg, 1.04 mmol) and Intermediate 3 (895 mg, 1.88 mmol) as a yellow solid (420 mg). Yield: 100%. Compound was taken to the next step without any characterization.

Intermediate 38:6-Fluoro-1-(5-((5-fluoro-3-oxoisobenzofuran-1 (3H)-ylidene)methyl)pyridin-3-yl)-3-hydroxy-3-methylindolin-2-one Following the general procedure 2, the titled compound was synthesized from Intermediate 36 (300 mg, 1.04 mmol) and Intermediate 23 (929 mg, 1.88 mmol) as a yellow gel (440 mg). Yield: 100%. Compound was taken to the next step without any characterization.

Intermediate 39:1-(4-((5-Fluoro-3-oxoisobenzofuran-1 (3H)-ylidene)methyl)pyridin-2-yl)-3-hydroxy-3-methylindolin-2-one Following the general procedure 2, the titled compound was synthesized from Intermediate 14 (350 mg, 1.30 mmol) and Intermediate 23 (1.15 g, 1.8 mmol) as a dark brown gel (800 mg). Yield: 100%. Compound was taken to the next step without any characterization.

Intermediate 40:1-(4-(1,3-Dioxolan-2-yl)pyridin-2-yl)-5-fluoro-3-hydroxy-3-methylindolin-2-one Following the general procedure 1, the titled compound was synthesized from Intermediate 12 (2 g, 8.7 mmol) and Intermediate 29 (1.57 g, 8.7 mmol). Crude product obtained was purified by combi-flash using MeOH and DCM (5:95) as eluent. Combined pure fractions from combi-flash were distilled to obtain the titled compound as a brown solid (900 mg). Yield: 31%, $^1$H-NMR (δ ppm, DMSO-$d_6$, 400 MHz): 8.61 (d, J 4.8, 1H), 7.81 (s, 1H), 7.64 (dd, J 8.8, 4.4, 1H), 7.42 (dd, J 5.2, 1.2, 1H), 7.35 (dd, J 8, 2.8, 1H), 7.14 (td, J 9.2, 2.8, 1H), 6.33 (s, 1H), 5.89 (s, 1H), 4.05-3.98 (m, 4H), 1.51 (s, 3H).

Intermediate 41:2-(5-Fluoro-3-hydroxy-3-methyl-2-oxoindolin-1-yl)isonicotinaldehyde Intermediate 40 (765 mg, 2.31 mmol) was dissolved in THF (8 ml) and added Concentrated Hydrochloric acid (3 ml). This mixture was refluxed at 80° C. for 3 h. After 3 h, reaction mass cooled to 0° C. and pH of the reaction mixture adjusted to ~7 using saturated aqueous sodium bicarbonate solution. Aqueous reaction mixture extracted with MeOH and DCM (1:9) (2*50 ml). Combined organic layers dried on anhydrous $Na_2SO_4$ and evaporated on rotavapor to obtain the titled compound as a brown liquid (662 mg). Yield: 100%. Compound was taken to the next step without any characterization.

Intermediate 42:5-Fluoro-1-(4-((5-fluoro-3-oxoisobenzofuran-1 (3H)-ylidene)methyl)pyridin-2-yl)-3-hydroxy-3-methylindolin-2-one Following the general procedure 2, the titled compound was synthesized from Intermediate 41 (662 mg, 2.31 mmol) and Intermediate 23 (2.05 g, 4.16 mmol) as a dark brown gel (930 mg). Yield: 100%. Compound was taken to the next step without any characterization.

Intermediate 43:3-hydroxy-3-(trifluoromethyl)indolin-2-one

This compound was prepared by the following the reported procedure (Chen Zang et. al Organic & Biomolecular Chemistry, 2013, 11, 5621-5633). Aniline (6 g, 64.4 mmol) and ethyl 3,3,3-trifluoro-2-oxopropanoate (13.1 g, 77.3) were taken in a microwave vial. 1,2-Dichlorobenzene (17.16 ml) was added to this vial and heated to 150° C. for 20 mins in a microwave oven. Reaction mass diluted with water (150 ml) and Brine (150 ml). Aqueous layer extracted with EtOAc to obtain crude. Crude was purified by column chromatography to obtain the titled compound as an off-white solid (4.9 g). Yield: 35%, $^1$H-NMR (δ ppm, DMSO-$d_6$, 400 MHz): 10.80 (s, 1H), 7.59 (s, 1H), 7.42-7.33 (m, 2H), 7.05 (t, J 7.6, 1H), 6.89 (d, J 8, 1H). MS (m/z): 216.21 ([M−H]$^+$).

Intermediate 44:1-(5-(1,3-Dioxolan-2-yl)pyridin-3-yl)-3-hydroxy-3-(trifluoromethyl)indolin-2-one Following the general procedure 1, the titled compound was synthesized from Intermediate 4 (2.64 g, 11.5 mmol) and Intermediate 43 (2.49 g, 11.5 mmol). Crude product obtained was purified by combi-flash using MeOH and DCM (2.4:97.6) as eluent. Combined pure fractions from combi-flash were distilled to obtain the titled compound as a brown solid (700 mg). Yield: 17%, $^1$H-NMR (δ ppm, DMSO-$d_6$, 400 MHz): 8.77 (s, 1H), 8.70 (d, J 1.6, 1H), 7.94 (s, 1H), 7.91 (s, 1H), 7.59 (d, J 7.2, 1H), 7.45 (t, J 7.6, 1H), 7.25 (t, J 7.6, 1H), 6.85 (d, J 8, 1H), 5.95 (s, 1H), 4.12-4.07 (m, 2H), 4.04-3.95 (m, 2H). MS (m/z): 367.34 ([M+H]$^+$).

Intermediate 45:5-(3-Hydroxy-2-oxo-3-(trifluoromethyl)indolin-1-yl)nicotinaldehyde Intermediate 44 (680 mg, 1.9 mmol) was dissolved in a mixture of water (17 ml) and acetone (17 ml). To this mixture Oxalic acid hydrate (2.34 g, 18.6 mmol) was added and stirred at 70° C. for 16 h. Distilled out acetone from the reaction mixture and basified with 10% aq. Sodium bicarbonate solution. Aqueous layer extracted with DCM and combined DCM layers were distilled to obtain crude. Crude was triturated with diethyl ether to obtain titled compound as a brown solid (490 mg). Yield: 82%, $^1$H-NMR (δ ppm, DMSO-$d_6$, 400 MHz): 10.19 (s, 1H), 9.18 (d, J 1.7, 1H), 8.96 (d, J 2.4, 1H), 8.36 (t, J 2, 1H), 7.60 (t, J 7.5, 1H), 7.47 (td, J 7.8, 1.1, 1H), 7.28 (t, J 7.5, 1H), 7.00 (d, J 7.9, 1H). MS (m/z): 323.0 ([M+H]$^+$).

Intermediate 46:3-Hydroxy-1-(5-((3-oxoisobenzofuran-1 (3H)-ylidene)methyl)pyridin-3-yl)-3-(trifluoromethyl)indolin-2-one Following the general procedure 2, the titled compound was synthesized from Intermediate 45 (490 mg, 1.5 mmol) and Intermediate 3 (800 mg, 1.7 mmol) as a yellow solid (660 mg). MS (m/z): 437.36 ([M−H]$^-$).

Intermediate 47:2-(3-Iodophenyl)-1,3-dioxolane

3-Iodobenzaldehyde (14.5 g, 62.5 mmol) was suspended in toluene (145 ml). To this mixture p-Toluenesulfonic acid monohydrate (594 mg, 3.12 mmol) and ethylene glycol (4.65 g, 75 mmol) were added and refluxed for 7 h under a dean-stark condenser. After 7 h, reaction mixture cooled to rt and diluted with toluene (29 ml) and washed with saturated aqueous sodium bicarbonate solution (75 ml). Organic layer washed with water (2*75 ml) and dried on anhydrous $Na_2SO_4$. Organic layer distilled out under vacuum to obtain the titled compound (15 g) as a yellow liquid. Yield: 87%, $^1$H-NMR (δ ppm, $CDCl_3$, 400 MHz): 7.86 (d, J 1.6, 1H), 7.73 (dd, J 7.6, 1.2, 1H), 7.45 (d, J 7.2, 1H), 7.14 (td, J 7.6, 1H), 5.78 (s, 1H), 4.17-4.10 (m, 2H), 4.08-4.01 (m, 2H). MS (m/z): 276.98 ([M+H]$^+$).

Intermediate 48:1-(3-(1,3-Dioxolan-2-yl)phenyl)-3-hydroxy-3-methylindolin-2-one

Following the general procedure 1, the titled compound was synthesized from Intermediate 47 (12 g, 52.39 mmol) and Intermediate 5 (8.55 g, 52.39). Crude product was purified by combi-flash using Ethyl acetate and Petroleum ether (1:1) as eluent. Combined pure fractions from combi-flash were distilled to obtain the titled compound as a black gel (7.8 g). Yield: 48%, $^1$H-NMR (δ ppm, DMSO-$d_6$, 400 MHz): 7.59 (t, J 7.2, 1H), 7.51 (d, J 7.6, 1H), 7.48-7.40 (m, 3H), 7.24 (t, J 7.2, 1H), 7.10 (t, J 7.2, 1H), 6.68 (d, J 7.6, 1H), 6.11 (s, 1H), 5.80 (s, 1H), 4.09-4.03 (m, 2H), 3.99-3.92 (m, 2H), 1.49 (s, 3H).

Intermediate 49:3-(3-Hydroxy-3-methyl-2-oxoindolin-1-yl)benzaldehyde

Intermediate 48 (7.7 g, 25 mmol) was dissolved in a mixture of water (60 ml) and acetone (60 ml). To this mixture Oxalic acid hydrate (8 g, 125 mmol) was added and stirred at 55° C. for 3 h. Distilled out acetone from the reaction mixture and basified with 10% aq. Sodium bicarbonate solution. Aqueous layer extracted with DCM (3*100 ml) and combined DCM layers were distilled to obtain titled compound as a brown solid (6 g). It has been used in the next step without further purification. Yield: 91%, $^1$H-NMR (δ ppm, DMSO-$d_6$, 400 MHz): 10.07 (s, 1H), 8.01-7.94 (m, 2H), 7.85-7.75 (m, 2H), 7.46 (d, J 6.8, 1H), 7.26 (t, J 7.2, 1H), 7.13 (t, J 7.2, 1H), 6.80 (d, J7.6, 1H), 6.16 (s, 1H), 1.52 (s, 3H).

Intermediate 50:3-Hydroxy-3-methyl-1-(3-((3-oxoisobenzofuran-1 (3H)-ylidene)methyl)phenyl)indolin-2-one Following the general procedure 2, the titled compound was synthesized from Intermediate 49 (5.5 g, 20.6 mmol) and Intermediate 3 (10.8 g, 22.6 mmol) as a black gel (7.9 g). Yield: 100%. Compound was taken to next step without any characterization.

Intermediate 51:1-(2-fluoro-5-((5-fluoro-3-oxoisobenzofuran-1 (3H)-ylidene)methyl)phenyl)-3-hydroxy-3-methylindolin-2-one Following the general procedure 2, the titled compound was synthesized from Intermediate 7 (2 g, 7 mmol) and Intermediate 23 (4 g, 8 mmol) as a black gel (3.1 g). Yield: 100%. Compound was taken to next step without any characterization.

Intermediate 52:4-((5-(3-Chloro-3-methyl-2-oxoindolin-1-yl)pyridin-3-yl)methyl)phthalazin-1(2H)-one 4-((5-(3-Hydroxy-3-methyl-2-oxoindolin-1-yl)pyridin-3-yl)methyl)phthalazin-1(2H)-one (Example 1) (8 g, 20.1 mmol) and thionyl chloride (33.9 g, 285 mmol) were mixed at 0° C. and refluxed at 90° C. for 1 h. Thionyl chloride distilled out from the reaction mixture to obtain a solid. Solid was suspended in water and basified with aq. Sodium bicarbonate. Filtered the solid and washed with mixture of EtOAc and diethyl ether (1:1) to obtain the titled compound (7.7 g) as a white solid. Yield: 92%, $^1$H-NMR (δ ppm, DMSO-$d_6$, 400 MHz): 12.58 (s, 1H), 8.68 (d, J 1.2, 1H), 8.59 (d, J 3.2, 1H), 8.26 (d, J 7.2, 1H), 8.06 (d, J 8.4, 1H), 7.97-7.91 (m, 2H), 7.85 (t, J 7.2, 1H), 7.66 (d, J 6.4, 1H), 7.32 (td, J 8.0, 1.2, 1H), 7.20 (t, J 7.2, 1H), 6.76 (d, J 7.6, 1H) 4.47 (s, 2H), 1.96 (s, 3H). MS (m/z): 417.29 ($[M+H]^+$).

Intermediate 53: Tert-butyl pyridin-3-ylcarbamate

3-Aminopyridine (45 g, 0.478 mol) was dissolved in 2-Propanol (150 ml) and water (29 ml) and cooled to 0° C. Boc anhydride (119 g, 0.545 mol) was dissolved in 2-Propanol (75 ml) and added to the above mixture at 0° C. This mixture was stirred at rt for 18 h. After 18 h, 2-propanol was distilled out from reaction mixture to obtain a residue. Water (100 ml) was added to residue and extracted with MTBE (2*200 ml). Combined organic layers washed with brine (100 ml) and dried on anhydrous $Na_2SO_4$. Organic layer distilled under vacuum to obtain a crude. Crude was purified by column chromatography using EtOAc and Petether (3:7) as eluent to afford the titled compound as a white solid (74 g). Yield: 80%, $^1$H-NMR (δ ppm, DMSO-$d_6$, 400 MHz): 7.77 (s, 1H), 7.36 (d, J 4, 1H), 7.17 (d, J 7.6, 1H), 6.55 (dd, J 7.6, 4, 1H), 0.74 (s, 9H). MS (m/z): 194.93 ($[M+H]^+$).

Intermediate 54: Ethyl 2-(3-((tert-butoxycarbonyl)amino)pyridin-4-yl)-2-oxoacetate Intermediate 53 (17 g, 87.5 mmol) was dissolved in THF (400 ml). To this mixture N,N,N,N-Tetramethylethylenediamine (25.33 g, 218 mmol) was added and cooled to −78° C. t-BuLi (14.02 g, 219 mmol) was added drop-wise for 45 mins to the above mixture. Reaction mixture warmed to −10 to −20° C. and stirred for 2 h. After 2 h, reaction mixture again cooled to −60° C. and added diethyl oxalate (38.4 g, 262.6 mmol). Reaction mixture warmed to 0° C. and stirred at 0° C. for 3 h. After 3 h, reaction mixture quenched with aq. $NH_4Cl$ at 0° C. Aqueous layer extracted with EtOAc (2*200 ml). Combined organic layers were washed with water (200 ml) and dried on ahydrous $Na_2SO_4$. Organic layer distilled under vacuum to obtain crude. Crude was purified by column chromatography on 60-120 mesh silica gel using EtOAc and Petether (2:8) as eluent to afford the titled compound as a brown oil (25 g). Yield: 25%, $^1$H-NMR (δ ppm, DMSO-$d_6$, 400 MHz): 10.34 (s, 1H), 8.51 (d, J 2.4, 1H), 8.41 (dd, J 4.8, 2.4, 1H), 7.46 (dd, J 4.8, 2.4, 1H), 4.24 (q, J 7.2, 2H), 1.41 (s, 9H), 1.26 (t, J 7.2, 3H).

Intermediate 55: 1H-Pyrrolo[2,3-c]pyridine-2,3-dione

Intermediate 54 (1.7 g, 5.77 mmol) was heated to 180° C. for 7 min under high vacuum. After 7 mins, reaction mixture cooled to rt. The reaction at the above scale was repeated 6 more times. The combined residue weres purified by combi-flash using ethyl acetate as eluent to obtain titled compound as a yellow solid (2.23 g). Yield: 37%, $^1$H-NMR (δ ppm, DMSO-$d_6$, 400 MHz): 11.20 (s, 1H), 8.44 (t, J 5.2, 1H), 8.33 (d, J 5.2, 1H), 7.41 (t, J 5.2, 1H). MS (m/z): 147.20 ($[M-H]^-$).

Intermediate 56:3-Hydroxy-3-methyl-1,3-dihydro-2H-pyrrolo[2,3-c]pyridin-2-one Intermediate 55 (2.1 g, 14 mmol) was dissolved in THF (5 ml) under nitrogen atmosphere and cooled to −5° C. 3M Methyl magnesium chloride in THF (14 ml. 43 mmol) was added to the above mixture drop-wise. The reaction mixture stirred at 0 to 5° C. for 2 h. After 2h, reaction mixture quenched with aq. Ammonium chloride solution (50 ml) and extracted with MeOH and DCM (1:9) (6*50 ml). Combined organic layers were dried on anhydrous $Na_2SO_4$. Organic layer distilled to obtain a crude. Crude was purified by combi-flash using MeOH and DCM (8:92) as eluent to obtain the titled compound (1.2 g) as a brown solid. Yield: 52%. $^1$H-NMR (δ ppm, DMSO-$d_6$, 400 MHz): 10.45 (s, 1H), 8.30 (d, J 4.8, 1H), 8.15 (d, J 4.8, 1H), 7.36 (d, J 4.8, 1H), 6.16 (s, 1H), 1.38 (s, 3H). MS (m/z): 165.05 ($[M+H]^+$).

Intermediate 56:1-(3-(1,3-dioxolan-2-yl)phenyl)-3-hydroxy-3-methyl-1,3-dihydro-2H-pyrrolo[2,3-c]pyridin-2-one Following the general procedure 1, the titled compound was synthesized from Intermediate 47 (680 mg, 2.5 mmol) and Intermediate 56 (400 mg, 2.5 mmol). Crude product was purified by combi-flash using MeOH and DCM (4:96) as eluent. Combined pure fractions from combi-flash were distilled to obtain the titled compound as a black gel (300 mg). Yield: 32%, $^1$H-NMR (δ ppm, DMSO-$d_6$, 400 MHz): 8.44 (bs, 1H), 8.06 (bs, 1H), 7.60 (t, J 7.9, 1H), 7.55-7.49 (m, 4H), 6.36 (s, 1H), 5.82 (s, 1H), 4.09-4.00 (m, 2H), 3.99-3.91 (m, 2H), 1.52 (s, 3H). MS (m/z): 313.29 ($[M+H]^+$).

Intermediate 57:3-(3-Hydroxy-3-methyl-2-oxo-2,3-dihydro-1H-pyrrolo[2,3-c]pyridin-1-yl)benzaldehyde Intermediate 56 (280 mg, 0.5 mmol) was dissolved in a mixture of water (4 ml) and acetone (4 ml). To this mixture Oxalic acid hydrate (570 mg, 4.5 mmol) was added and stirred at 55° C. for 4 h. Distilled out acetone from the reaction mixture and basified with 10% aq. Sodium bicarbonate solution. Aqueous layer extracted with DCM (3*100 ml) and combined DCM layers were distilled to obtain titled compound as a brown solid (160 g). It has been used in the next step without further purification. Yield: 67%. MS (m/z): 269.22 ([M+H]$^+$).

Intermediate 58:3-Hydroxy-3-methyl-1-(3-((3-oxoisobenzofuran-1 (3H)-ylidene)methyl)phenyl)-1,3-dihydro-2H-pyrrolo[2,3-c]pyridin-2-one Following the general procedure 2, the titled compound was synthesized from Intermediate 57 (150 mg, 0.56 mmol) and Intermediate 3 (290 mg, 0.62 mmol) as a black gel (210 mg). Yield: 100%. Compound was taken to next step without any characterization. MS (m/z): 383.61 ([M−H]$^-$).

Intermediate 59:1-(Naphthalen-1-ylmethyl)indoline-2,3-dione

Indoline-2,3-dione (37 g, 0.25 mol) was dissolved in DMF (740 ml) and cooled to 0° C. Sodium hydride was added to the above mixture in portions at 0° C. and stirred at same temperature for 10 mins. 1-(Chloromethyl) naphthalene was added to above reaction mixture at 0° C., stirred at 0° C. for 30 mins and at rt for 12 h. After 12 h, reaction mixture was quenched with satd. $NH_4Cl$ (1 lt) to obtain a solid. Solid was filtered and washed with water (500 ml). Solid was dissolved in MeOH and DCM (1:9) mixture (2 lt) and dried on anhydrous $Na_2SO_4$. This solution was distilled to obtain a crude. Crude was purified by column chromatography on 60-120 mesh silica gel using DCM as eluent. Combined pure fractions from column were distilled to obtain titled compound (43.8 g) as a brown solid. Yield: 61%, $^1$H-NMR (δ ppm, DMSO-$d_6$, 400 MHz): 8.20 (d, J 8.4, 1H), 7.99 (d, J 8.4, 1H), 7.88 (d, J 8.4, 1H), 7.68-7.50 (m, 5H), 7.42 (t, J 8, 1H), 7.12 (t, J 7.6, 1H), 6.90 (d, J 8, 1H), 5.39 (s, 2H).

Intermediate 60: (R)-3-Methyl-1-(naphthalen-1-ylmethyl)-2-oxoindolin-3-yl acetate (R)—N-(4-chlorobenzyl)-2-hydroxy-2-phenylacetamide (3.148 g, 12.03 mmol) was dissolved in DCM (1200 ml) and stirred under nitrogen atmosphere. To this mixture 2M dimethyl zinc (60.14 ml, 120.3 mmol) was added and stirred at rt for 30 mins. Intermediate 59 (17.28 g, 60.14 mmol) was dissolved in DCM (600 ml) and added to the above reaction mixture drop-wise for 1 h. Reaction mixture further stirred at rt for 1 h.

Reaction mixture was cooled to 0° C., and acetic anhydride (22.7 ml, 240 mmol) was added drop-wise to the reaction mixture. After addition of acetic anhydride, reaction mixture was warmed to rt and stirred for 1 h. At this stage, Pyridine (19.03 ml, 240 mmol) and DMAP (733 mg, 6 mmol) were added to reaction mixture and stirred at rt for 1 h. After 1 h, again Pyridine (9.52 ml, 120 mmol), DMAP (733 mg, 6 mmol) and acetic anhydride (11.37 ml, 120 mmol) were added and stirred the reaction at rt for 1 h. Reaction mixture quenched with aqueous ammonium chloride (75 g in 750 ml water) solution. Separated the organic and aqueous layers. Aqueous layer extracted with DCM (2*350 ml). Combined DCM layers were washed with water (700 ml) and brine (700 ml). Organic layer distilled to obtain crude solid (22 g). Crude solid (22 g) was suspended in a mixture of EtOAc (12 ml) and hexane (108 ml) and stirred for 2 h. Filtered the solid and washed with hexane (35 ml). Solid dried under vacuum to obtain the titled compound (17 g) as an off-white solid. Yield: 82%. Chiral HPLC Purity: 90.45%, Retention time: 22.92 min. $^1$H-NMR (δ ppm, DMSO-$d_6$, 400 MHz): 8.18 (d, J 8, 1H), 7.97 (d, J 8, 1H), 7.85 (d, J 8, 1H), 7.58 (quintet, J 7.2, 2H), 7.45 (d, J 6.8, 1H), 7.41 (d, J 8, 1H), 7.37 (d, J 7.2, 1H), 7.18 (t, J 8, 1H), 7.02 (t, J 7.6, 1H), 6.75 (d, J 8, 1H), 5.44 (d, J 16.8, 1H), 5.32 (d, J 16.8, 1H), 2.07 (s, 3H), 1.59 (s, 3H).

Intermediate 61: (R)-3-Methyl-2-oxoindolin-3-yl acetate

Intermediate 60 (1.25 g, 3.62 mmol) was suspended in Chlorobenzene (70 ml), N-Bromosuccunimide (772 mg, 4.34 mmol) and AIBN(118 mg, 0.723 mmol) were added. This mixture was refluxed at 130° C. for 3 h. After 3 h, Chlorobenzene was distilled from reaction mixture to obtain a crude. Crude was diluted with water and extracted with EtOAc. Organic layer dried on anhydrous $Na_2SO_4$ and distilled to obtain a crude. Crude was purified by combi-flash using EtOAc and Petether (2:8) as eluent to obtain the titled compound as a pale-brown solid (360 mg). Yield: 48%. Chiral HPLC Purity: 89.85%, Retention time: 5.18 min. $^1$H-NMR (δ ppm, DMSO-$d_6$, 400 MHz): 10.52 (s, 1H), 7.24 (d, J 7.2, 1H), 7.22 (td, J 7.6, 1.2, 1H), 6.95 (td, J 7.6, 1.2, 1H), 6.82 (d, J 8, 1H), 2.00 (s, 3H), 1.47 (s, 3H).

Intermediate 62: (R)-(+)-3-Hydroxy-3-methylindolin-2-one

Intermediate 61 (300 mg, 1.46 mmol) and LiOH (135 mg, 2.2 mmol) were suspended in MeOH (1.5 ml) and THF (1.5 ml). This mixture was stirred at rt for 3 h. After 3 h, reaction mixture diluted with water (10 ml) and extracted with EtOAc (2*10 ml). Combined organic layers were dried on anhydrous $Na_2SO_4$ and distilled to obtain titled compound as a pale-brown solid (150 mg). Yield: 48%. Chiral HPLC Purity: 82.81%, Retention time: 3.01 min. $^1$H-NMR (δ ppm, DMSO-$d_6$, 400 MHz): 10.19 (s, 1H), 7.26 (d, J 7.2, 1H), 7.17 (td, J 7.6, 1.2, 1H), 6.94 (td, J 7.6, 1.2, 1H), 6.78 (d, J 7.6, 1H), 5.82 (s, 1H), 1.33 (s, 3H).

Intermediate 63:1-(5-(1,3-dioxolan-2-yl)-2-fluorophenyl)indolin-2-one

Following the General procedure-1 titled compound was synthesized from Intermediate 1 (10 g, 34.00 mmol) and Oxindole (4.53 g, 34.00 mmol) as a brown liquid (700 mg). Yield: 6%. Compound was taken to the next step without any characterization.

Intermediate 64:4-Fluoro-3-(2-oxoindolin-1-yl)benzaldehyde

Intermediate 63 (350 mg, 1.17 mmol) was dissolved in THF (5 ml) and added 6N Hydrochloric acid (4 ml). This mixture was stirred at room temperature for 1 h. After 1 h, reaction mass cooled to 0° C. and pH adjusted to ~7 using saturated aqueous sodium bicarbonate solution (50 ml). Aqueous reaction mixture extracted with MeOH:DCM (1:9) and evaporated the organic layer on rotavapor to afford crude. Crude was purified by combi-flash using MeOH and DCM (1:9) as eluent. Combined pure fractions from combi-flash were distilled on rotavapor to obtain the titled compound as a brown gel (160 mg). Yield: 53.69%. Compound was taken to the next step without any characterization.

Intermediate 65:1-(2-Fluoro-5-((3-oxoisobenzofuran-1 (3H)-ylidene)methyl)phenyl) indolin-2-one Following the general procedure 2, the titled compound was synthesized from Intermediate 64 (150 mg, 0.58 mmol)

and Intermediate 3 (500 mg, 1.06) as a yellow gel (240 mg). Yield: 100%. Compound was taken to the next step without any characterization.

Intermediate 66: Tert-butyl 2-oxoindoline-1-carboxylate

Oxindole (16 g, 0.12 mol) dissolved in THF (382 ml) and cooled to 0° C. To this mixture Sodium carbonate (101.89 g, 0.96 mol) and Boc-anhydride (41.4 ml, 0.18 mol) were added at 0° C. Reaction mixture heated to 70° C. and stirred at the same temperature for 24 h. Reaction mixture cooled to room temperature and filtered the insoluble solid from the reaction mixture. Filtered Solid was stirred with Ethyl acetate (200 ml) and filtered. Combined filtrates were distilled to obtain a crude. Crude was purified by Combi-flash using Ethyl acetate and Petroleum ether (2:98) as eluent. Combined pure fractions from combi-flash were distilled to obtain the titled compound as a white solid (5.5 g). Yield: 19.6%, $^1$H-NMR (δ ppm, $CDCl_3$, 400 MHz): 7.78 (d, J 8.2, 1H), 7.30 (t, J 7.8, 1H), 7.24 (d, J 7.8, 1H), 7.13 (t, J 7.4, 1H), 3.65 (s, 2H), 1.64 (s, 9H).

Intermediate 67: Tert-butyl 3,3-dimethyl-2-oxoindoline-1-carboxylate

Intermediate 66 (5.5 g, 23.6 mmol) and methyl iodide (4.42 ml, 70.77 mmol) were dissolved in THF (45 ml) and cooled to 0° C. To this mixture Sodium hydride (60%) (2.06 g, 51.9 mmol) was added lot-wise at same temperature. Reaction mixture warmed to room temperature and stirred for 3 h. Reaction mixture cooled to 0° C. and quenched with water (100 ml). Aqueous reaction mixture extracted with Ethyl acetate and ethyl acetate layer distilled to obtain a crude. Crude was purified by Combi-flash using Ethyl acetate and Petroleum ether (15:85) as eluent. Combined pure fractions from combi-flash were distilled to obtain the titled compound as an off-white solid (2.4 g). Yield: 39%, $^1$H-NMR (δ ppm, $CDCl_3$, 400 MHz): 7.84 (d, J 8.1, 1H), 7.29 (d, J 7.2, 1H), 7.24-7.13 (m, 2H), 1.65 (s, 9H), 1.42 (s, 6H).

Intermediate 68:3,3-Dimethylindolin-2-one

This intermediate was prepared as per the report in the literature (Ref: Li, Honghe; et al Angewandte Chemie, International Edition (2019), 58 (20), 6732-6736) Intermediate 67 (2 g, 7.65 mmol) was dissolved in Dichloromethane (10 ml) and cooled to 0° C. Trifluoroacetic acid (5.9 ml, 76.5 mmol) was added to the above reaction mixture and stirred at 0° C. for 30 mins. Reaction mixture pH was adjusted to ~7 using saturated aqueous sodium bicarbonate solution. Aqueous layer extracted with MeOH:DCM (1:9) and evaporated organic layer to obtain a crude. Crude was suspended in Diethyl ether (20 ml) and stirred to obtain a solid. Solid was filtered and dried under vacuum to obtain the titled compound (1.25 g) as brown solid. Yield: 100%, $^1$H-NMR (δ ppm, DMSO-$d_6$, 400 MHz): 10.29 (s, 1H), 7.25 (d, J 7.2, 1H), 7.14 (t, J 7.6, 1H), 6.94 (t, J 7.5, 1H), 6.82 (d, J 7.6, 1H), 1.22 (s, 6H).

Intermediate 69:1-(5-(1,3-Dioxolan-2-yl)-2-fluorophenyl)-3,3-dimethylindolin-2-one Following the general procedure 1, the titled compound was synthesized from Intermediate 1 (1.64 g, 5.58 mmol) and Intermediate 68 (0.9 g, 5.58). Crude product was purified by combi-flash using Ethyl acetate and Petroleum ether (20:80) as eluent. Combined pure fractions from combi-flash were distilled to obtain the titled compound as a brown solid. Yield: 32%, $^1$H-NMR (δ ppm, DMSO-$d_6$, 400 MHz): 7.63-7.60 (m, 2H), 7.50 (t, J 9.5, 1H), 7.45 (d, J 7.1, 1H), 7.21 (t, J 7.7, 1H), 7.10 (t, J 7.2, 1H), 6.56 (d, J 7.7, 1H), 5.79 (s, 1H), 4.10-4.03 (m, 2H), 3.97-3.90 (m, 2H), 1.41 (s, 3H), 1.37 (s, 3H).

Intermediate 70:3-(3,3-dimethyl-2-oxoindolin-1-yl)-4-fluorobenzaldehyde

Intermediate 69 (600 mg, 1.84 mmol) was dissolved in THF (6 ml) and added 6N Hydrochloric acid (2 ml). This mixture was stirred at room temperature for 30 mins. After 30 mins, reaction mass cooled to 0° C. and pH adjusted to ~7 using saturated aqueous sodium bicarbonate solution (50 ml). Aqueous reaction mixture extracted with Dichloromethane and MeOH mixture (1:9). Organic layer dried on anhydrous $Na_2SO_4$ and evaporated to obtain a crude. Crude was stirred with Petroleum ether (3 ml) to obtain a solid and filtered the solid. Solid was dried under vacuum to obtain the titled compound as a brown solid (450 mg). Yield: 86%. $^1$H-NMR (δ ppm, DMSO-$d_6$, 400 MHz): 10.02 (s, 1H), 8.17 (d, J 7.2, 1H), 8.14-8.11 (m, 1H), 7.73 (t, J 9.4, 1H), 7.48 (d, J 7, 1H), 7.22 (t, J 6.8, 1H), 7.13 (t, J 7.4, 1H), 6.67 (d, J 7.8, 1H), 1.43 (s, 3H), 1.39 (s, 3H).

Intermediate 71:1-(2-Fluoro-5-((3-oxoisobenzofuran-1 (3H)-ylidene)methyl)phenyl)-3,3-dimethylindolin-2-one Following the general procedure 2, the titled compound was synthesized from Intermediate 70 (450 mg, 1.58 mmol) and Intermediate 3 (1.36 g, 2.86 mmol) as a yellow solid. Yield: 100%.

Intermediate 72:1-(5-(1,3-Dioxolan-2-yl)pyridin-3-yl)-3,3-dimethylindolin-2-one

Following the general procedure 1, the titled compound was synthesized from Intermediate 4 (1.28 g, 5.58 mmol) and Intermediate 68 (899 mg, 5.58). Crude product was purified by combi-flash using Ethyl acetate and Petroleum ether (20:80) as eluent. Combined pure fractions from combi-flash were distilled to obtain the titled compound as a brown solid (800 mg). Yield: 46%, $^1$H-NMR (δ ppm, DMSO-$d_6$, 400 MHz): 8.70 (d, J 6.5, 2H), 7.96 (s, 1H), 7.46 (d, J 7.7, 1H), 7.22 (t, J 7.7, 1H), 7.12 (t, J 7.4, 1H), 6.75 (d, J 7.7, 1H), 5.92 (s, 1H), 4.12-4.07 (m, 2H), 4.01-3.95 (m, 2H), 1.40 (s, 6H).

Intermediate 73:5-(3,3-Dimethyl-2-oxoindolin-1-yl) nicotinaldehyde

Intermediate 72 (800 mg, 2.6 mmol) was dissolved in THF (15 ml) and added Concentrated Hydrochloric acid (2.5 ml). This mixture was stirred at 80° C. for 2 h. After 2 h, reaction mass cooled to room temperature and added water (50 ml). pH of the reaction mixture adjusted to ~7 using saturated aqueous sodium bicarbonate solution. Aqueous reaction mixture extracted with Dichloromethane. Organic layer dried on anhydrous $Na_2SO_4$ and evaporated to obtain titled compound as a brown solid (600 mg). Yield: 87%. $^1$H-NMR (δ ppm, DMSO-$d_6$, 400 MHz): 10.17 (s, 1H), 9.12

(s, 1H), 8.99 (s, 1H), 8.40 (s, 1H), 7.48 (d, J 7.2, 1H), 7.24 (t, J 7.4, 1H), 7.14 (t, J 7.3, 1H), 6.89 (d, J 7.7, 1H), 1.42 (s, 6H).

Intermediate 74:3,3-Dimethyl-1-(5-((3-oxoisobenzofuran-1 (3H)-ylidene)methyl)pyridin-3-yl)indolin-2-one Following the general procedure 2, the titled compound was synthesized from Intermediate 73 (550 mg, 2.7 mmol) and Intermediate 3 (1.76 g, 3.71 mmol) as a yellow solid (620 mg). Yield: 100%. Compound was taken to the next step without any characterization.

Intermediate 75: Diethyl 2-(3-nitropyridin-2-yl)malonate

Sodium hydride (60%) (18.22 g, 0.46 mol) was suspended in DMSO (360 ml) under nitrogen atmosphere and cooled to 0° C. Diethyl malonate (69.18 ml, 0.46 mol) was added to the above mixture, warmed to room temperature and stirred for 30 mins. 2-Chloro-3-nitropyridine (31 g, 0.195 mol) was added to the above reaction mixture and heated to 100° C. for 15 mins. After 15 mins, Reaction mixture was cooled to 0° C. and quenched with aqueous ammonium chloride solution. Aqueous reaction mixture extracted with ethyl acetate (2*250 ml) and ethyl acetate layer washed with water (2*500 ml). Organic layer distilled under vacuum to obtain the titled compound as a brown gel (55.2 g). Yield: 100%, $^1$H-NMR (δ ppm, DMSO-$d_6$, 400 MHz): 8.88 (dd, J 4.6, 1.3, 1H), 8.61 (dd, J 8.4, 1.4, 1H), 7.75 (dd, J 8.3, 4.7, 1H), 5.59 (s, 1H), 4.20-4.14 (m, 4H), 1.17 (t, J 7.1, 6H).

Intermediate 76: Ethyl 2-(3-nitropyridin-2-yl)acetate

A mixture of Intermediate 75 (55 g, 0.282 mol), Lithium chloride (20.65 g, 0.487 mol), DMSO (550 ml) and water (3.5 ml, 0.194 mol) were heated to 100° C. for 16 h. Reaction mixture cooled to room temperature and quenched with brine solution (500 ml). Aqueous reaction mixture extracted with ethyl acetate (2*200 ml). Combined organic layers washed with water (5*200 ml) and dried on anhydrous $Na_2SO_4$. Organic layer distilled to obtain a crude. Crude was purified by combi-flash using Ethyl acetate and Petether (15:85) as eluent. Pure fractions from combi-flash were distilled to obtain the titled compound as a brown gel (35.9 g). Yield: 88%, $^1$H-NMR (δ ppm, DMSO-$d_6$, 400 MHz): 8.84 (d, J 3.5, 1H), 8.54 (d, J 8.3, 1H), 7.68 (dd, J 8.2, 4.8, 1H), 4.23 (s, 2H), 4.08 (q, J 7.1, 2H), 1.15 (t, J 7.1, 3H).

Intermediate 77: Ethyl 2-methyl-2-(3-nitropyridin-2-yl) propanoate

Intermediate 76 (3.8 g, 18 mmol) was dissolved in DMF (30 ml) under nitrogen atmosphere. To this solution Methyl iodide (3.3 ml, 54 mmol) and 18-Crown-6 (0.48 g, 1.8 mmol) were added and cooled to 0° C. To this reaction mixture sodium hydride (60%) (1.59 g, 39.8 mmol) was added lot-wise and stirred at 0° C. for 1 h. Reaction mixture quenched with water at 0° C. and extracted with ethyl acetate (2*100 ml). Combined organic layers were washed with water (5*100 ml) and evaporated on rotavapor to obtain crude. Crude was purified by combi-flash using Ethyl acetate and Petether (8:92) as eluent. Pure fractions from combi-flash were combined and distilled to obtain the titled compound as a brown gel (3 g). Yield: 70%, $^1$H-NMR (δ ppm, $CDCl_3$, 400 MHz): 8.79 (d, J 4.5, 1H), 8.24 (d, J 8.1, 1H), 7.40 (dd, J 8.1, 4.6, 1H), 4.12 (q, J 7.1, 2H), 1.71 (s, 6H), 1.20 (t, J 7.1, 3H).

Intermediate 78:3,3-Dimethyl-1,3-dihydro-2H-pyrrolo[3,2-b]pyridin-2-one

Intermediate 77 (3 g, 12 mmol) was suspended in ethanol (25 ml) and Ammonium formate (3.17 g, 50.37 mmol) and 10% Pd/C (300 mg) were added. This mixture was stirred at 100° C. for 2 h. Reaction mixture filtered on a cealite bed and cealite bed washed with MeOH and DCM (1:9) (250 ml). Combined filtrates were distilled on rotavapor to obtain a residue. Residue was dissolved in a mixture of MeOH and DCM (1:9) (250 ml) and washed with water (2*100 ml). Organic layer dried on anhydrous $Na_2SO_4$ and distilled to obtain the title compound as a brown solid (1.45 g). Yield: 71%, $^1$H-NMR (δ ppm, DMSO-$d_6$, 400 MHz): 10.51 (s, 1H), 8.07 (d, J 4.4, 1H), 7.20-7.11 (m, 2H), 1.23 (s, 6H).

Intermediate 79:1-(5-(1,3-Dioxolan-2-yl)pyridin-3-yl)-3,3-dimethyl-1,3-dihydro-2H-pyrrolo[3,2-b]pyridin-2-one Following the general procedure 1, the titled compound was synthesized from Intermediate 4 (1.5 g, 6.5 mmol) and Intermediate 78 (1.06 g, 6.5 mmol). Crude product obtained was purified by combi-flash using MeOH and DCM (3:97) as eluent. Combined pure fractions from combi-flash were distilled to obtain the titled compound as a pale-yellow gel (1.2 g). Yield: 59%, $^1$H-NMR (δ ppm, DMSO-$d_6$, 400 MHz): 8.75 (s, 1H), 8.70 (s, 1H), 8.24 (d, J 4.8, 1H), 8.01 (s, 1H), 7.27-7.21 (m, 1H), 7.18 (d, J 8, 1H), 5.92 9s, 1H), 4.11-4.05 (m, 2H), 4.01-3.96 (m, 2H), 1.41 (s, 6H).

Intermediate 80:5-(3,3-Dimethyl-2-oxo-2,3-dihydro-1H-pyrrolo[3,2-b]pyridin-1-yl)nicotinaldehyde Intermediate 79 (620 mg, 2 mmol) was dissolved in THF (5 ml) and added Concentrated Hydrochloric acid (1.5 ml). This mixture was stirred at 80° C. for 3 h. After 3 h, reaction mass cooled to 0° C. and pH of the reaction mixture adjusted to ~7 using saturated aqueous sodium bicarbonate solution. Aqueous reaction mixture extracted with MeOH and DCM (1:9) (2*100 ml). Combined organic layers were dried on anhydrous $Na_2SO_4$ and evaporated to obtain titled compound as a pale-yellow gel (532 mg). Yield: 100%. $^1$H-NMR (δ ppm, DMSO-$d_6$, 400 MHz): 10.18 (s, 1H), 9.13 (s, 1H), 9.02 (s, 1H), 8.43 (s, 1H), 8.26 (d, J 4.2, 1H), 7.32 (d, J 8, 1H), 7.29-7.22 (m, 1H), 1.43 (s, 6H).

Intermediate 81:3,3-Dimethyl-1-(5-((3-oxoisobenzofuran-1 (3H)-ylidene)methyl)pyridin-3-yl)-1,3-dihydro-2H-pyrrolo[3,2-b]pyridin-2-one Following the general procedure 2, the titled compound was synthesized from Intermediate 80 (532 mg, 2 mmol) and Intermediate 3 (1.70 g, 4 mmol) as a yellow solid (762 mg). Yield: 100%. Compound was taken to the next step without any characterization.

Intermediate 82:1-(5-(1,3-Dioxolan-2-yl)-2-fluorophenyl)-3,3-dimethyl-1,3-dihydro-2H-pyrrolo[3,2-b]pyridin-2-one Following the general procedure 1, the titled compound was synthesized from Intermediate 1 (730 mg, 2.48 mmol)

and Intermediate 78 (402 mg, 2.48 mmol). Crude product obtained was purified by combi-flash using MeOH and DCM (2.5:97.5) as eluent. Combined pure fractions from combi-flash were distilled to obtain the titled compound as a brown gel (460 mg). Yield: 57%, $^1$H-NMR (δ ppm, DMSO-$d_6$, 400 MHz): 8.23 (d, J 5, 1H), 7.67 (dd, J 7.2, 2, 1H), 7.65-7.60 (m, 1H), 7.51 (t, J 9.9, 1H), 7.23 (dd, J 8,5, 1H), 6.99 (d, J 8, 1H), 5.79 (s, 1H), 4.10-4.03 (m, 2H), 3.97-3.91 (m, 2H), 1.43 (s, 3H), 1.38 (s, 3H).

Intermediate 83:3-(3,3-Dimethyl-2-oxo-2,3-dihydro-1H-pyrrolo[3,2-b]pyridin-1-yl)-4-fluorobenzaldehyde Intermediate 82 (440 mg, 1.34 mmol) was dissolved in THF (10 ml) and added Concentrated Hydrochloric acid (2 ml). This mixture was stirred at room temperature for 30 mins. After 30 mins, reaction mass cooled to 0° C. and pH of the reaction mixture adjusted to ~ 7 using saturated aqueous sodium bicarbonate solution. Aqueous reaction mixture extracted with MeOH and DCM (1:9). Organic layer dried on anhydrous $Na_2SO_4$ and evaporated to obtain titled compound as a pale-yellow gel (380 mg). Yield: 100%, $^1$H-NMR (δ ppm, DMSO-$d_6$, 400 MHz): 10.02 (s, 1H), 8.25 (dd, J 5, 1.2, 1H), 8.23 (dd, J 6.8, 4.8, 1H), 8.16-8.10 (m, 1H), 7.74 (t, J 9.6, 1H), 7.25 (dd, J 8, 5, 1H), 7.13 (d, J 8, 1H), 1.45 (s, 3H), 1.40 (s, 3H).

Intermediate 84:1-(2-Fluoro-5-((3-oxoisobenzofuran-1 (3H)-ylidene)methyl)phenyl)-3,3-dimethyl-1,3-dihydro-2H-pyrrolo[3,2-b]pyridin-2-one Following the general procedure 2, the titled compound was synthesized from Intermediate 83 (380 mg, 1.33 mmol) and Intermediate 3 (1.70 g, 4 mmol) as a yellow gel (404 mg). Yield: 100%. Compound was taken to the next step without any characterization.

Intermediate 85: Tert-butyl 2'-oxospiro[cyclopropane-1,3'-indoline]-1'-carboxylate Intermediate 66 (2.5 g, 10.72 mmol) was dissolved in DMF (25 ml) under nitrogen atmosphere. To this solution 1,2-Dibromoethane (2.77 ml, 32.16 mmol) and 18-Crown-6 (0.28 g, 1.072 mmol) were added and cooled to 0° C. To this mixture sodium hydride (60%) (943 mg, 23.6 mmol) was added lot-wise at 0° C. Reaction mixture stirred at room temperature for 3 h and at 70° C. for 3 h. Reaction mixture quenched with water at 0° C. and extracted with MeOH and DCM (1:9) (3*200 ml). Combined organic layers washed with water (3*250 ml) and evaporated to obtain crude. Crude was purified by combi-flash using Ethyl acetate and Petether (4:96) as eluent. Pure fractions from combi-flash were combined and distilled to obtain the titled compound as a white solid (1.1 g). Yield: 40%, $^1$H-NMR (δ ppm, $CDCl_3$, 400 MHz): 7.90 (d, J 8.2, 1H), 7.30-7.22 (m, 1H), 7.12 (t, J 7.5, 1H), 6.81, (d, J 7.4, 1H), 1.82 (q, J 4.2, 2H), 1.65 (s, 9H), 1.54 (q, J 3.9, 2H).

Intermediate 86: Spiro [cyclopropane-1,3'-indolin]-2'-one

Intermediate 85 (1.1 g, 4.24 mmol) was dissolved in Dichloromethane (40 ml) and cooled to 0° C. Trifluoroacetic acid (3.27 ml, 42.4 mmol) was added to the mixture and stirred at 0° C. for 30 mins. Reaction mixture pH was adjusted to ~7 using saturated aqueous sodium bicarbonate solution. Aqueous layer extracted with MeOH:DCM (1:9) (4*100 ml) and evaporated organic layer to obtain the titled compound as a brown solid (650 mg). Yield: 96%.

$^1$H-NMR (δ ppm, DMSO-$d_6$, 400 MHz): 10.52 (s, 1H), 7.13 (td, J 7.6, 1.7, 1H), 6.97-6.85 (m, 3H), 1.56-1.50 (m, 2H), 1.46-1.41 (m, 2H).

Intermediate 87: 1'-(5-(1,3-Dioxolan-2-yl)pyridin-3-yl)spiro[cyclopropane-1,3'-indolin]-2'-one Following the general procedure 1, the titled compound was synthesized from Intermediate 4 (940 mg, 4.08 mmol) and Intermediate 86 (649 mg, 4.08 mmol). Crude product obtained was purified by combi-flash using Ethyl acetate and Petroleum ether (35:65) as eluent. Combined pure fractions from combi-flash were distilled to obtain the titled compound as a brown gel (501 mg). Yield: 40%, $^1$H-NMR (δ ppm, DMSO-$d_6$, 400 MHz): 8.74 (d, J 2.3, 1H), 8.70 (d, J 1.7, 1H), 7.97 (d, J 2.1, 1H), 7.25-7.19 (m, 1H), 7.15-7.06 (m, 2H), 6.84 (d, J 7.8, 1H), 5.92 (s, 1H), 4.11-4.03 (m, 2H), 4.01-3.93 (m, 2H), 1.78-1.72 (m, 2H), 1.67-1.62 (m, 2H).

Intermediate 88:5-(2'-Oxospiro[cyclopropane-1,3'-indolin]-1'-yl)nicotinaldehyde

Intermediate 87 (480 mg, 1.56 mmol) was dissolved in THF (15 ml) and added Concentrated Hydrochloric acid (2 ml). This mixture was refluxed at 80° C. for 3.5 h. After 3.5 h, reaction mass cooled to 0° C. and pH of the reaction mixture adjusted to ~7 using saturated aqueous sodium bicarbonate solution. Aqueous reaction mixture extracted with MeOH and DCM (1:9) (2*150 ml). Organic layer dried on anhydrous $Na_2SO_4$ and evaporated to obtain the titled compound as a yellow gel (411 mg). Yield: 100%. Compound was taken to the next step without any characterization.

Intermediate 89: 1'-(5-((3-Oxoisobenzofuran-1 (3H)-ylidene)methyl)pyridin-3-yl)spiro[cyclopropane-1,3'-indolin]-2'-one Following the general procedure2, the titled compound was synthesized from Intermediate 88 (411 mg, 1.56 mmol) and Intermediate 3 (1.33 g, 2.8 mmol) as a yellow gel (411 mg). Yield: 100%. Compound was taken to the next step without any characterization.

Example 1

4-((5-(3-Hydroxy-3-methyl-2-oxoindolin-1-yl)pyridin-3-yl)methyl)phthalazin-1(2H)-one Following the general procedure 3, the titled compound was synthesized from Intermediate 11 (1 g, 2.6 mmol), hydrazine hydrate (156 mg, 3.12 mmol) and acetic acid (78 mg, 1.3 mmol). Purification: Combi-Flash. Eluent: MeOH and DCM: 5.3:94.7. Appearance: Off-White solid. Yield: 236 mg. % Yield: 23%. M.P.: 110-113° C. $^1$H-NMR (δ ppm, DMSO-$d_6$, 400 MHz): 12.59 (s, 1H), 8.65 (s, 1H), 8.52 (s, 1H), 8.26 (d, J 7.8, 1H), 8.06 (d, J 8.1, 1H), 7.93 (t, J 8, 1H), 7.85 (t, J 8, 1H), 7.79 (s, 1H), 7.43 (d, J 7.2, 1H), 7.21 (t, J 7.6, 1H), 7.11 (t, J 7.2, 1H), 6.69 (d, J 7.7, 1H), 6.12 (s, 1H), 4.46 (s, 2H), 1.48 (s, 3H) MS (m/z): 399.29 ($[M+H]^+$).

Example 2

(R)-(+)-4-((5-(3-Hydroxy-3-methyl-2-oxoindolin-1-yl)pyridin-3-yl)methyl)phthalazin-1(2H)-one Method-1

Using the preparative methods reported in the General Procedure 4, the titled compound was resolved as a pure enantiomer from the racemic mixture of 4-((5-(3-Hydroxy-3-methyl-2-oxoindolin-1-yl)pyridin-3-yl)methyl)phthalazin-1(2H)-one (Example 1). Chiral HPLC Purity: 99.16, Retention time: 11.48 min. M.P.: 97-100° C. $^1$H-NMR (δ ppm, DMSO-$d_6$, 400 MHz): 12.58 (s, 1H), 8.65 (d, J 1.7, 1H), 8.52 (d, J 2.2, 1H), 8.26 (d, J 7.4, 1H), 8.06 (d, J 8.0, 1H), 7.93 (t, J 7.8, 1H), 7.85 (t, J 7.8, 1H), 7.79 (t, J 2.0, 1H), 7.43 (d, J 6.9, 1H), 7.22 (t, J 7.8, 1H), 7.11 (t, J 7.6, 1H), 6.69 (d, J 7.6, 1H), 6.12 (s, 1H), 4.47 (s, 2H), 1.48 (s, 3H). MS (m/z): 399.39 ([M+H]$^+$). $[\alpha]_D25$: +30.36°[MeOH: CHLOROFORM (1:9); c 1.0]

Method-2:

5-Bromonicotinaldehyde was converted to acetal by treating with Ethylene glycol. Above acetal was reacted under buchwald condition with (R)-(+)-3-methyl-2-oxoindolin-3-yl acetate to give (R)-(+)-1-(5-(1,3-dioxolan-2-yl)pyridin-3-yl)-3-methyl-2-oxoindolin-3-yl acetate. (R)-(+)-1-(5-(1,3-dioxolan-2-yl)pyridin-3-yl)-3-methyl-2-oxoindolin-3-yl was deprotected under acidic condition to give (R)-(+)-1-(5-formylpyridin-3-yl)-3-methyl-2-oxoindolin-3-yl acetate. (R)-(+)-1-(5-formylpyridin-3-yl)-3-methyl-2-oxoindolin-3-yl acetate thus obtained was reacted with (3-oxo-1,3-dihydroisobenzofuran-1-yl)triphenylphosphonium bromide under Wittig reaction condition to give (R)-(+)-3-methyl-2-oxo-1-(5-((3-oxoisobenzofuran-1 (3H)-ylidene)methyl)pyridin-3-yl)indolin-3-yl acetate. (R)-(+)-3-methyl-2-oxo-1-(5-((3-oxoisobenzofuran-1 (3H)-ylidene)methyl)pyridin-3-yl)indolin-3-yl acetate was reacted with hydrazine hydrate to give (R)-(+)-4-((5-(3-Hydroxy-3-methyl-2-oxoindolin-1-yl)pyridin-3-yl)methyl)phthalazin-1(2H)-one.

Method-3: The title compound was also synthesised following the procedure as in given in Example-1 and using chiral intermediate-5 (R)-(+)-3-Hydroxy-3-methylindolin-2-one.

Example 3

(S)-(−)-4-((5-(3-Hydroxy-3-methyl-2-oxoindolin-1-yl)pyridin-3-yl)methyl)phthalazin-1(2H)-one Using the preparative methods reported in the General Procedure 4, the titled compound was resolved as a pure enantiomer from the racemic mixture of 4-((5-(3-Hydroxy-3-methyl-2-oxoindolin-1-yl)pyridin-3-yl)methyl)phthalazin-1(2H)-one (Example 1). Chiral HPLC Purity: 99.82, Retention time: 13.61 min. M.P.: 94-97° C. $^1$H-NMR (δ ppm, DMSO-$d_6$, 400 MHz): 12.59 (s, 1H), 8.65 (d, J 1.7, 1H), 8.52 (d, J 2.2, 1H), 8.26 (d, J 7.8, 1H), 8.06 (d, J 7.9, 1H), 7.93 (t, J 7.6, 1H), 7.85 (t, J 8.0, 1H), 7.79 (t, J 2, 1H), 7.43 (d, J 7.2, 1H), 7.21 (t, J 7.8, 1H), 7.11 (t, J 7.8, 1H), 6.69 (d, J 7.8, 1H), 6.12 (s, 1H), 4.46 (s, 2H), 1.48 (s, 3H). MS (m/z): 399.41 ([M+H]$^+$). $[\alpha]_D25$: −26.44°[MeOH: CHLOROFORM (1:9); c 1.0]

Example 4

4-(4-Fluoro-3-(3-hydroxy-3-methyl-2-oxoindolin-1-yl)benzyl)phthalazin-1(2H)-one Following the general procedure 3, the titled compound was synthesized from Intermediate 8 (800 mg, 1.99 mmol), hydrazine hydrate (119 mg, 2.4 mmol) and acetic acid (59 mg, 1 mmol). Purification: Combi-Flash. Eluent: MeOH and DCM: 3:97. Appearance: Off-White solid. Yield: 240 mg. % Yield: 29%. M.P.: 131-134° C. $^1$H-NMR (δ ppm, DMSO-$d_6$, 400 MHz): 12.60 (s, 1H), 8.25 (d, J 7.7, 1H), 7.99 (d, J 7.9, 1H), 7.90 (t, J 7.3, 1H), 7.81 (t, 7.3, 1H), 7.54-7.49 (m, 1H), 7.47-7.35 (m, 3H), 7.24-7.17 (m, 1H), 7.09 (t, J 7.3, 1H), 6.46 (d, J 7.7, 1H), 6.25 (s, 0.4H), 6.13 (s, 0.6H), 4.39 (s, 1.2 H), 4.36 (s, 0.8 H), 1.50 (s, 1.8 H), 1.45 (s, 1.2 H). MS (m/z): 416.1 ([M+H]$^+$).

Example 5

4-((5-(3-Ethyl-3-hydroxy-2-oxoindolin-1-yl)pyridin-3-yl)methyl)phthalazin-1(2H)-one Following the general procedure 3, the titled compound was synthesized from Intermediate 19 (900 mg, 2.26 mmol), hydrazine hydrate (135 mg, 2.71 mmol) and acetic acid (67 mg, 1.13 mmol). Purification: Combi-Flash. Eluent: MeOH and DCM: 5:95. Appearance: Off-White solid. Yield: 200 mg. % Yield: 21%. M.P.: 117-120° C. $^1$H-NMR (δ ppm, DMSO-$d_6$, 400 MHz): 12.58 (s, 1H), 8.65 (d, J 1.4, H), 8.50 (d, J 2.1, 1H), 8.26 (d, J 7.7, 1H), 8.07 (d, J 8, 1H), 7.94 (t, J 7, 1H), 7.85 (t, J 7.2, 1H), 7.79 (s, 1H), 7.40 (d, J 7.2, 1H), 7.23 (t, J 7.1, 1H), 7.12 (t, J 7.5, 1H), 6.70 (d, J 7.8, 1H), 6.12 (s, 1H), 4.47 (s, 2H), 1.94-1.83 (m, 2H), 0.68 (t, J 7.4, 3H). MS (m/z): 413.43 ([M+H]$^+$).

Example 6

7-Fluoro-4-((5-(3-hydroxy-3-methyl-2-oxoindolin-1-yl)pyridin-3-yl)methyl)phthalazin-1(2H)-one Following the general procedure 3, the titled compound was synthesized from Intermediate 24 (650 mg, 1.61 mmol), hydrazine hydrate (97 mg, 1.94 mmol) and acetic acid (48 mg, 0.81 mmol). Purification: Combi-Flash. Eluent: MeOH and DCM: 4:96. Appearance: Off-White solid. Yield: 110 mg. % Yield: 16%. M.P.: 133-136° C. $^1$H-NMR (δ ppm, DMSO-$d_6$, 400 MHz): 12.69 (s, 1H), 8.65 (d, J 1.5, 1H), 8.53 (d, J 2.1, 1H), 8.19 (dd, J 8.9, 5.0, 1H), 7.94 (dd, J 8.8, 2.7, 1H), 7.84 (td, J 8.8, 2.7, 1H), 7.81 (t, J 2.7, 1H), 7.44 (d, J 7, 1H), 7.23 (t, J 7.7, 1H), 7.11 (t, J 7.4, 1H), 6.71 (d, J 7.8, 1H), 6.13 (s, 1H), 4.47 (s, 2H), 1.48 (s, 3H). MS (m/z): 417.47 ([M−H]$^-$).

Example 7

(+)-7-Fluoro-4-((5-(3-hydroxy-3-methyl-2-oxoindolin-1-yl)pyridin-3-yl)methyl)phthalazin-1(2H)-one Using the preparative methods reported in the General Procedure 4, the titled compound was resolved as a pure enantiomer from the racemic mixture of 7-Fluoro-4-((5-(3-hydroxy-3-methyl-2-oxoindolin-1-yl)pyridin-3-yl)methyl)phthalazin-1(2H)-one (Example 6). Chiral HPLC Purity: 99.54, Retention time: 5.86 min. M.P.: 148-151° C. $^1$H-NMR (δ ppm, DMSO-$d_6$, 400 MHz): 12.69 (s, 1H), 8.65 (d, J 1.6, 1H), 8.53 (d, J 2.0, 1H), 8.19 (dd, J 9.2, 5.2, 1H), 7.94 (dd, J 8.8, 2.7, 1H), 7.84 (td, J 8.8, 2.7, 1H), 7.80 (t, J 2.7, 1H), 7.44 (d, J 7, 1H), 7.23 (t, J 7.6, 1H), 7.12 (t, J 7.6, 1H), 6.71 (d, J 7.6, 1H), 6.13 (s, 1H), 4.47 (s, 2H), 1.48 (s, 3H). MS (m/z): 417.32 ([M+H]$^+$). $[\alpha]_D25$: +23.51°[MeOH: CHLOROFORM (1:9); c 0.5]

Example 8

(−)-7-Fluoro-4-((5-(3-hydroxy-3-methyl-2-oxoindolin-1-yl)pyridin-3-yl)methyl)phthalazin-1(2H)-one Using the preparative methods reported in the General Procedure 4, the titled compound was resolved as a pure enantiomer from the racemic mixture of 7-Fluoro-4-((5-(3-hydroxy-3-methyl-2-oxoindolin-1-yl)pyridin-3-yl)methyl) phthalazin-1(2H)-one (Example 6). Chiral HPLC Purity: 99.64%, Retention time: 6.75 min. M.P.: 138-141° C. $^1$H-NMR (δ ppm, DMSO-$d_6$, 400 MHz): 12.69 (s, 1H), 8.65 (d, J 1.5, 1H), 8.53 (d, J 2.1, 1H), 8.19 (dd, J 8.9,5, 1H), 7.94 (dd, J 8.8, 2.7, 1H), 7.84 (t, J 8.8, 2.7, 1H), 7.80 (t, J 2.7, 1H), 7.44 (d, J 7.6, 1H), 7.23 (t, J 7.6, 1H), 7.12 (t, J 7.6, 1H), 6.71 (d, J 7.6, 1H), 6.13 (s, 1H), 4.47 (s, 2H), 1.48 (s, 3H). MS (m/z): 417.28 ([M+H]$^+$). $[\alpha]_D$25: −27.74°[MeOH: CHLOROFORM (1:9); c 0.5]

Example 9

6-Fluoro-4-((5-(3-hydroxy-3-methyl-2-oxoindolin-1-yl)pyridin-3-yl)methyl)phthalazin-1(2H)-one Following the general procedure 3, the titled compound was synthesized from Intermediate 28 (650 mg, 1.61 mmol), hydrazine hydrate (97 mg, 1.94 mmol) and acetic acid (48 mg, 0.80 mmol). Purification: Combi-Flash. Eluent: MeOH and DCM: 4.1:95.9. Appearance: Pale-Yellow solid. Yield: 210 mg. % Yield: 31%. M.P.: 132-135° C. $^1$H-NMR (8 ppm, DMSO-$d_6$, 400 MHz): 12.66 (s, 1H), 8.65 (d, J 1.6, 1H), 8.53 (d, J 2.2, 1H), 8.33 (dd, J 8.8, 5.7, 1H), 7.93 (dd, J 9.8, 2.2, 1H), 7.83 (s, 1H), 7.72 (t, J 8.8, 1H), 7.44 (d, J 7, 1H), 7.23 (t, J 7.7, 1H), 7.12 (t, J 7.1, 1H), 6.73 (d, J 7.8, 1H), 6.14 (s, 1H), 4.44 (s, 2H), 1.49 (s, 3H). MS (m/z): 417.43 ([M+H]$^+$).

Example 10

7-Fluoro-4-((5-(5-fluoro-3-hydroxy-3-methyl-2-oxoindolin-1-yl)pyridin-3-yl)methyl)phthalazin-1(2H)-one Following the general procedure 3, the titled compound was synthesized from Intermediate 33 (350 mg, 0.83 mmol), hydrazine hydrate (49 mg, 1 mmol) and acetic acid (24 mg, 0.42 mmol). Purification: Combi-Flash. Eluent: MeOH and DCM: 4.2:95.8. Appearance: Off-White solid. Yield: 140 mg. % Yield: 38%. M.P.: 157-160° C. $^1$H-NMR (δ ppm, DMSO-$d_6$, 400 MHz): 12.68 (s, 1H), 8.64 (d, J 2, 1H), 8.52 (d, J 2, 1H), 8.19 (dd, J 8.8, 5, 1H), 7.94 (dd, J 8.8, 2.6, 1H), 7.84 (td, J 8.8, 2.6, 1H), 7.81 (t, J 2, 1H), 7.35 (dd, J 7.8, 2.4, 1H), 7.07 (td, J 8.8, 2.5, 1H), 6.75 (dd, J 8.8, 4.0, 1H), 6.25 (s, 1H), 4.46 (s, 2H), 1.50 (s, 3H). MS (m/z): 435.32 ([M+H]$^+$).

Example 11

(+)-7-Fluoro-4-((5-(5-fluoro-3-hydroxy-3-methyl-2-oxoindolin-1-yl)pyridin-3-yl)methyl)phthalazin-1(2H)-one Using the preparative methods reported in the General Procedure 4, the titled compound was resolved as a pure enantiomer from the racemic mixture of 7-Fluoro-4-((5-(5-fluoro-3-hydroxy-3-methyl-2-oxoindolin-1-yl)pyridin-3-yl) methyl)phthalazin-1(2H)-one (Example 10). Chiral HPLC Purity: 99.90%, Retention time: 5.88 min. M.P.: 148-151° C. $^1$H-NMR (8 ppm, DMSO-$d_6$, 400 MHz): 12.69 (s, 1H), 8.64 (d, J 2, 1H), 8.52 (d, J 2, 1H), 8.19 (dd, J 8.8, 5, 1H), 7.94 (dd, J 8.4, 2.4, 1H), 7.84 (td, J 8.8, 2.4, 1H), 7.81 (t, J 2, 1H), 7.35 (dd, J 8, 2.8, 1H), 7.08 (td, J 8.8, 2.4, 1H), 6.75 (dd, J 8.4, 4.0, 1H), 6.26 (s, 1H), 4.46 (s, 2H), 1.50 (s, 3H). MS (m/z): 435.39 ([M+H]$^+$). $[\alpha]_D$25: +17.79°[MeOH: CHLOROFORM (1:9); c 0.5]

Example 12

(−)-7-Fluoro-4-((5-(5-fluoro-3-hydroxy-3-methyl-2-oxoindolin-1-yl)pyridin-3-yl)methyl)phthalazin-1(2H)-one Using the preparative methods reported in the General Procedure 4, the titled compound was resolved as a pure enantiomer from the racemic mixture of 7-Fluoro-4-((5-(5-fluoro-3-hydroxy-3-methyl-2-oxoindolin-1-yl)pyridin-3-yl) methyl)phthalazin-1(2H)-one (Example 10). Chiral HPLC Purity: 99.28%, Retention time: 6.92 min. M.P.: 154-157° C. $^1$H-NMR (8 ppm, DMSO-$d_6$, 400 MHz): 12.69 (s, 1H), 8.64 (d, J 2, 1H), 8.52 (d, 1H), 8.19 (dd, J 8.8, 5, 1H), 7.94 (dd, J 8.4, 2.4, 1H), 7.84 (td, J 8.4, 2.4, 1H), 7.81 (t, J 2, 1H), 7.36 (dd, J 7.6, 2.4, 1H), 7.08 (td, J 9.2, 2.8, 1H), 6.75 (dd, J 8.4, 4.0, 1H), 6.26 (s, 1H), 4.46 (s, 2H), 1.50 (s, 3H). MS (m/z): 435.33 ([M+H]$^+$). $[\alpha]_D$25: −25.52°[MeOH: CHLOROFORM (1:9); c 0.5]

Example 13

4-((5-(5-Fluoro-3-hydroxy-3-methyl-2-oxoindolin-1-yl)pyridin-3-yl)methyl)phthalazin-1(2H)-one Following the general procedure 3, the titled compound was synthesized from Intermediate 32 (351 mg, 0.87 mmol), hydrazine hydrate (52 mg, 1.05 mmol) and acetic acid (26 mg, 0.44 mmol). Purification: Combi-Flash. Eluent: MeOH and DCM: 5.1:94.9. Appearance: Off-Brown solid. Yield: 90 mg. % Yield: 25%. M.P.: 116-120° C. $^1$H-NMR (δ ppm, DMSO-$d_6$, 400 MHz): 12.58 (s, 1H), 8.65 (d, J 2, 1H), 8.52 (d, J 2, 1H), 8.26 (d, J 7.4 1H), 8.06 (d, J 7.9, 1H), 7.93 (t, J 8.4, 1H), 7.85 (t, J 7.4, 1H), 7.80 (t, J 2, 1H), 7.35 (dd, J 7.9, 2.6, 1H), 7.06 (td, J 8.8, 2.7, 1H), 6.72 (dd, J 8.6, 4.1, 1H), 6.24 (s, 1H), 4.46 (s, 2H), 1.49 (s, 3H). MS (m/z): 417.35 ([M+H]$^+$).

Example 14

(+)-4-((5-(5-Fluoro-3-hydroxy-3-methyl-2-oxoindolin-1-yl)pyridin-3-yl)methyl)phthalazin-1(2H)-one Using the preparative methods reported in the General Procedure 4, the titled compound was resolved as a pure enantiomer from the racemic mixture of 4-((5-(5-Fluoro-3-hydroxy-3-methyl-2-oxoindolin-1-yl)pyridin-3-yl)methyl) phthalazin-1(2H)-one (Example 13). Chiral HPLC Purity: 99.65%, Retention time: 6.05 mins. M.P.: 198-201° C. $^1$H-NMR (δ ppm, DMSO-$d_6$, 400 MHz): 12.59 (s, 1H), 8.65 (d, J 2.5, 1H), 8.52 (d, J 1.2, 1H), 8.26 (d, J 8, 1H), 8.06 (d, J 8, 1H), 7.94 (t, J 7.6, 1H), 7.85 (t, J 7.4, 1H), 7.80 (t, J 2, 1H), 7.35 (dd, J 8, 2.4, 1H), 7.06 (td, J 8.8, 2.8, 1H), 6.72 (dd, J 8.8, 4, 1H), 6.25 (s, 1H), 4.46 (s, 2H), 1.49 (s, 3H). MS (m/z): 417.33 ([M+H]$^+$). $[\alpha]_D$25: +23.63°[MeOH: CHLOROFORM (1:9); c 0.5]

Example 15

(−)-4-((5-(5-Fluoro-3-hydroxy-3-methyl-2-oxoindolin-1-yl)pyridin-3-yl)methyl)phthalazin-1(2H)-one Using the preparative methods reported in the General Procedure 4, the titled compound was resolved as a pure enantiomer from the racemic mixture of 4-((5-(5-Fluoro-3-hydroxy-3-methyl-2-oxoindolin-1-yl)pyridin-3-yl)methyl) phthalazin-1(2H)-one (Example 13). Chiral HPLC Purity: 98.81%, Retention time: 7.61 min M.P.: 197-200° C. $^1$H-NMR (δ ppm, DMSO-$d_6$, 400 MHz): 12.59 (s, 1H), 8.65 (d, J 2.5, 1H), 8.52 (d, J 2, 1H), 8.26 (d, J 8, 1H), 8.06 (d, J 8, 1H), 7.94 (t, J 7.6, 1H), 7.85 (t, J 7.4, 1H), 7.80 (t, J 2, 1H), 7.35 (dd, J 8, 2.6, 1H), 7.06 (td, J 8.8, 2.8, 1H), 6.72 (dd, J 8.8, 4.2, 1H), 6.25 (s, 1H), 4.46 (s, 2H), 1.49 (s, 3H). MS (m/z): 417.34 ([M+H]$^+$). [α]]25: −28.17°[MeOH: CHLOROFORM (1:9); c 0.5]

Example 16

7-Fluoro-4-((5-(6-fluoro-3-hydroxy-3-methyl-2-oxoindolin-1-yl)pyridin-3-yl)methyl)phthalazin-1 (2H)-one Following the general procedure 3, the titled compound was synthesized from Intermediate 37 (400 mg, 1 mmol), hydrazine hydrate (59 mg, 1.19 mmol) and acetic acid (29 mg, 0.5 mmol). Purification: Combi-Flash. Eluent: MeOH and DCM: 4.7:95.3. Appearance: Off-White solid. Yield: 150 mg. % Yield: 36%. M.P.: 125-128° C. $^1$H-NMR (δ ppm, DMSO-$d_6$, 400 MHz): 12.57 (s, 1H), 8.66 (s, 1H), 8.52 (s, 1H), 8.26 (d, J 7.3, 1H), 8.06 (d, J 8, 1H), 7.92 (t, J 7, 1H), 7.84 (t, J 7.2, 1H), 7.80 (s, 1H), 7.46 (dd, J 8.1, 5.6, 1H), 6.93-6.88 (m, 1H), 6.54 (dd, J 9.4, 2.1, 1H), 6.15 (s, 1H), 4.47 (s, 2H), 1.48 (s, 3H). MS (m/z): 417.33 ([M+H]$^+$).

Example 17

7-Fluoro-4-((5-(6-fluoro-3-hydroxy-3-methyl-2-oxoindolin-1-yl)pyridin-3-yl)methyl)phthalazin-1 (2H)-one Following the general procedure 3, the titled compound was synthesized from Intermediate 38 (400 mg, 0.95 mmol), hydrazine hydrate (72 mg, 1.56 mmol) and acetic acid (39 mg, 0.47 mmol). Purification: Combi-Flash. Eluent: MeOH and DCM: 3.8:96.2. Appearance: Pale-Yellow solid. Yield: 90 mg. % Yield: 22%. M.P.: 219-221° C. $^1$H-NMR (8 ppm, DMSO-$d_6$, 400 MHz): 12.68 (s, 1H), 8.66 (d, J 7.1, 1H), 8.52 9d, J 2.2, 1H), 8.17 (dd, J 9, 5.04, 1H), 7.93 (dd, J 8.8, 2.7, 1H), 7.87-7.76 (m, 2H), 7.45 (dd, J 8.2, 5.7, 1H), 6.91 (t, J 10.1, 1H), 6.15 (s, 1H), 4.47 (s, 2H), 1.48 (s, 3H). MS (m/z): 435.32 ([M+H]$^+$).

Example 18

4-((2-(3-hydroxy-3-methyl-2-oxoindolin-1-yl)pyridin-4-yl)methyl)phthalazin-1(2H)-one Following the general procedure 3, the titled compound was synthesized from Intermediate 15 (500 mg, 1.3 mmol), hydrazine hydrate (78 mg, 1.56 mmol) and acetic acid (39 mg, 0.65 mmol). Purification: Column chromatography on 100-200 mesh silica gel. Eluent: MeOH and DCM: 1.5:98.5. Appearance: Off-White solid. Yield: 35 mg. % Yield: 6.7%. M.P.: 203-205° C. $^1$H-NMR (δ ppm, DMSO-$d_6$, 400 MHz): 12.63 (s, 1H), 8.51 (d, J 5.2, 1H), 8.28 (d, J 6.8, 1H), 7.99 (d, J 8, 1H), 7.91 (td, J 7.2, 1.2, 1H), 7.84 (t, J 7.2, 1H), 7.69 (s, 1H), 7.49 (d, J 8, 1H) 7.44 (d, J 6.8, 1H), 7.39 (d, J 5.2, 1H), 7.26 (td, J 7.6, 1.2, 1H), 7.14 (t, J 7.6, 1H), 6.15 (s, 1H), 4.46 (s, 2H), 1.48 (s, 3H). MS (m/z): 399.11 ([M+H]$^+$).

Example 19

(−)-4-((2-(3-Hydroxy-3-methyl-2-oxoindolin-1-yl) pyridin-4-yl)methyl)phthalazin-1(2H)-one Using the preparative methods reported in the General Procedure 4, the titled compound was resolved as a pure enantiomer from the racemic mixture of 4-((2-(3-hydroxy-3-methyl-2-oxoindolin-1-yl)pyridin-4-yl)methyl)phthalazin-1(2H)-one (Example 18). Chiral HPLC Purity: 99.54%, Retention time: 9.19 min. M.P.: 207-210° C. $^1$H-NMR (δ ppm, DMSO-$d_6$, 400 MHz): 12.63 (s, 1H), 8.49 (d, J 5.2, 1H), 8.26 (d, J 7.6, 1H), 7.98 (d, J 8, 1H), 7.90 (td, J 7.2, 1.2, 1H), 7.83 (t, J 7.2, 1H), 7.69 (s, 1H), 7.48 (d, J 8, 1H) 7.42 (d, J 7.2, 1H), 7.37 (d, J 5.0, 1H), 7.26 (td, J 7.6, 1.6, 1H), 7.12 (t, J 7.6, 1H), 6.15 (s, 1H), 4.45 (s, 2H), 1.48 (s, 3H). MS (m/z): 399.29 ([M+H]$^+$). $[\alpha]_D$25: −33.01° [MeOH: CHLOROFORM (1:9); c 0.5]

Example 20

(+)-4-((2-(3-Hydroxy-3-methyl-2-oxoindolin-1-yl)pyridin-4-yl)methyl)phthalazin-1(2H)-one Using the preparative methods reported in the General Procedure 4, the titled compound was resolved as a pure enantiomer from the racemic mixture of 4-((2-(3-hydroxy-3-methyl-2-oxoindolin-1-yl)pyridin-4-yl)methyl)phthalazin-1(2H)-one (Example 18). Chiral HPLC Purity: 99.11, Retention time: 11.22 min. M.P.: 205-208° C. $^1$H-NMR (δ ppm, DMSO-$d_6$, 400 MHz): 12.63 (s, 1H), 8.49 (d, J 5.2, 1H), 8.26 (d, J 7.6, 1H), 7.98 (d, J 8, 1H), 7.90 (td, J 7.2, 1.2, 1H), 7.83 (t, J 7.2, 1H), 7.68 (s, 1H), 7.48 (d, J 8, 1H) 7.44 (d, J 6.8, 1H), 7.37 (d, J 5.0, 1H), 7.26 (td, J 7.6, 1.2, 1H), 7.12 (t, J 7.6, 1H), 6.15 (s, 1H), 4.45 (s, 2H), 1.47 (s, 3H). MS (m/z): 399.29 ([M+H]$^+$). [α]]25: +29.62°[MeOH: CHLOROFORM (1:9); c 0.5]

Example 21

7-Fluoro-4-((2-(3-hydroxy-3-methyl-2-oxoindolin-1-yl)pyridin-4-yl)methyl)phthalazin-1(2H)-one Following the general procedure 3, the titled compound was synthesized from Intermediate 39 (640 mg, 1.3 mmol), hydrazine hydrate (32 mg, 0.65 mmol) and acetic acid (16 mg, 0.27 mmol). Purification: Column chromatography on 60-120 mesh silica gel: 3.8:96.2. Appearance: Off-White solid. Yield: 23 mg. % Yield: 5.2%. M.P.: 187-189° C. $^1$H-NMR (8 ppm, DMSO-$d_6$, 400 MHz): 12.74 (s, 1H), 8.50 (d, J 5.2, 1H), 8.10 (dd, J 9.0, 5, 1H), 7.94 (dd, J 8.8, 2.4 1H), 7.80 (td, J 8.8, 2.8, 1H), 7.67 (s, 1H), 7.48 (d, J 8, 1H), 7.42 (d, J 7.6, 1H), 7.36 (d, J 5.2, 1H), 7.26 (td, J 8, 1, 1H), 7.13 (t, J 7.2, 1H), 6.16 (s, 1H), 4.46 (s, 2H), 1.48 (s, 3H). MS (m/z): 417.16 ([M+H]$^+$).

Example 22

(−)-7-Fluoro-4-((2-(3-hydroxy-3-methyl-2-oxoindolin-1-yl)pyridin-4-yl)methyl)phthalazin-1(2H)-one Using the preparative methods reported in the General Procedure 4, the titled compound was resolved as a pure enantiomer from the racemic mixture of 7-Fluoro-4-((2-(3-hydroxy-3-methyl-2-oxoindolin-1-yl)pyridin-4-yl)methyl) phthalazin-1(2H)-one (Example 21). Chiral HPLC Purity: 99.95%, Retention time: 8.23 mins. M.P.: 165-168° C. $^1$H-NMR (δ ppm, DMSO-$d_6$, 400 MHz): 12.74 (s, 1H), 8.50

(d, J 5.2, 1H), 8.10 (dd, J 9.0, 5.2, 1H), 7.94 (dd, J 8.8, 2.4 1H), 7.80 (td, J 8.8, 2.8, 1H), 7.67 (s, 1H), 7.48 (d, J 8, 1H), 7.42 (d, J 7.6, 1H), 7.36 (d, J 5.2, 1H), 7.26 (td, J 8, 1, 1H), 7.13 (t, J 7.2, 1H), 6.16 (s, 1H), 4.46 (s, 2H), 1.47 (s, 3H). MS (m/z): 417.28 ([M+H]$^+$). $[\alpha]_D$25: −29.17°[MeOH: CHLOROFORM (1:9); c 0.5]

Example 23

(+)-7-Fluoro-4-((2-(3-hydroxy-3-methyl-2-oxoindolin-1-yl)pyridin-4-yl)methyl)phthalazin-1(2H)-one Using the preparative methods reported in the General Procedure 4, the titled compound was resolved as a pure enantiomer from the racemic mixture of 7-Fluoro-4-((2-(3-hydroxy-3-methyl-2-oxoindolin-1-yl)pyridin-4-yl)methyl) phthalazin-1(2H)-one (Example 21). Chiral HPLC Purity: 99.23, Retention time: 10.79 min. M.P.: 167-170° C. $^1$H-NMR (δ ppm, DMSO-$d_6$, 400 MHz): 12.74 (s, 1H), 8.50 (d, J 5.2, 1H), 8.10 (dd, J 8.8, 4.8, 1H), 7.95 (dd, J 8.8, 2.4, 1H), 7.80 (td, J 8.8, 2.8, 1H), 7.67 (s, 1H), 7.48 (d, J 8, 1H), 7.42 (d, J 7.2, 1H), 7.36 (d, J 5.2, 1H), 7.26 (d, J 7.6, 1H), 7.13 (t, J 7.2, 1H), 6.15 (s, 1H), 4.46 (s, 2H), 1.47 (s, 3H). MS (m/z): 417.30 ([M+H]$^+$). [α]]25: +24.29°[MeOH: CHLOROFORM (1:9); c 0.5]

Example 24

7-Fluoro-4-((2-(5-fluoro-3-hydroxy-3-methyl-2-oxoindolin-1-yl)pyridin-4-yl)methyl)phthalazin-1(2H)-one Following the general procedure 3, the titled compound was synthesized from Intermediate 42 (508 mg, 1.2 mmol), hydrazine hydrate (72 mg, 1.45 mmol) and acetic acid (36 mg, 0.6 mmol). Purification: Column chromatography on 100-200 mesh silica gel: 2:98. Appearance: Off-White solid. Yield: 80 mg. % Yield: 15.2%. M.P.: 225-228° C. $^1$H-NMR (8 ppm, DMSO-$d_6$, 400 MHz): 12.73 (s, 1H), 8.49 (d, J 4.8, 1H), 8.10 (dd, J 8.8, 4.8, 1H), 7.95 (dd, J 8.8, 2.8, 1H), 7.81 (td, J 8.4, 2.8, 1H), 7.72 (s, 1H), 7.61 (dd, J 9.2, 4.8, 1H), 7.37 (dd, J 4.8, 1.5, 1H), 7.33 (dd, J 8.0 2.8 1H), 7.12 (td, J 9.2, 2.8, 1H), 6.28 (s, 1H), 4.46 (s, 2H), 1.49 (s, 3H). MS (m/z): 435.14 ([M+H]$^+$).

Example 25

4-((5-(3-Hydroxy-2-oxo-3-(trifluoromethyl)indolin-1-yl)pyridin-3-yl)methyl)phthalazin-1(2H)-one Following the general procedure 3, the titled compound was synthesized from Intermediate 45 (670 mg, 1.5 mmol), hydrazine hydrate (100 mg, 2 mmol) and acetic acid (41 mg, 0.69 mmol). Purification: Combi-Flash. Eluent: MeOH and DCM: 2:98. Appearance: Off-White solid. Yield: 360 mg. % Yield: 52%. M.P.: 258-260° C. $^1$H-NMR (δ ppm, DMSO-$d_6$, 400 MHz): 12.57 (s, 1H), 8.70 (d, J 2, 1H), 8.52 (d, J 2, 1H), 8.26 (d, J 7.6, 1H), 8.08 (d, J 8, 1H), 7.94 (t, J 8.4, 1H), 7.93 (s, 1H), 7.89-7.82 (m, 2H), 7.57 (d, J 7.6, 1H), 7.42 (t, J 7.6, 1H), 7.23 (t, J 7.6, 1H), 6.81 (d, J 8, 1H), 4.49 (s, 2H). MS (m/z): 453.1 ([M+H]$^+$).

Example 26

(+)-4-((5-(3-Hydroxy-2-oxo-3-(trifluoromethyl)indolin-1-yl)pyridin-3-yl)methyl)phthalazin-1(2H)-one Using the preparative methods reported in the General Procedure 4, the titled compound was resolved as a pure enantiomer from the racemic mixture of 4-((5-(3-Hydroxy-2-oxo-3-(trifluoromethyl)indolin-1-yl)pyridin-3-yl)methyl) phthalazin-1(2H)-one (Example 25). Chiral HPLC Purity: 99.5, Retention time: 4.2 min. M.P.: 170-174° C. $^1$H-NMR (δ ppm, DMSO-$d_6$, 400 MHz): 12.60 (s, 1H), 8.71 (d, J 1.6, 1H), 8.54 (d, J 2.4, 1H), 8.29 (dd, J 8.0, 1.2, 1H), 8.10 (d, J 8.0, 1H), 7.98 (dt, J 7.2, 1.2, 1H), 7.94 (s, 1H), 7.89-7.83 (m, 2H), 7.59 (d, J 7.6, 1H), 7.46 (dt, J 7.6, 1.2, 1H), 7.27 (dt, J 8.0, 0.8, 1H), 6.83 (d, J 8.0, 1H), 4.50 (s, 2H). MS (m/z): 453.33 ([M+H]$^+$). $[\alpha]_D$25: +46.33°[CHLOROFORM; c 0.15].

Example 27

(−)-4-((5-(3-Hydroxy-2-oxo-3-(trifluoromethyl)indolin-1-yl)pyridin-3-yl)methyl)phthalazin-1(2H)-one Using the preparative methods reported in the General Procedure 4, the titled compound was resolved as a pure enantiomer from the racemic mixture of 4-((5-(3-Hydroxy-2-oxo-3-(trifluoromethyl)indolin-1-yl)pyridin-3-yl)methyl) phthalazin-1(2H)-one (Example 25). Chiral HPLC Purity: 99.9, Retention time: 7.3 min. M.P.: 210-214° C. $^1$H-NMR (δ ppm, DMSO-$d_6$, 400 MHz): 12.60 (s, 1H), 8.71 (d, J 2.0, 1H), 8.54 (d, J 2.4, 1H), 8.29 (dd, J 8.0, 0.8, 1H), 8.11 (d, J 8.0, 1H), 7.98 (dt, J 7.6, 1.6, 1H), 7.94 (s, 1H), 7.89-7.83 (m, 2H), 7.59 (d, J 7.2, 1H), 7.46 (dt, J 8.0, 1.2, 1H), 7.27 (dt, J 7.6, 0.8, 1H), 6.83 (d, J 8.4, 1H), 4.50 (s, 2H). MS (m/z): 453.33 ([M+H]$^+$). $[\alpha]_D$25:−41.50°[CHLOROFORM; c 0.15].

Example 28

4-(3-(3-Hydroxy-3-methyl-2-oxoindolin-1-yl)benzyl)phthalazin-1(2H)-one

Intermediate 49 (7.5 g, 19.6 mmol), hydrazine hydrate (1.26 g, 25.2 mmol) and 2-Propanol (150 ml) were mixed and refluxed at 100° C. for 3 h. After 3 h, reaction mixture cooled to rt and stirred at rt for 1 h. Water (100 ml) was added to reaction mixture. Aqueous layer extracted with MeOH and DCM (1:9) (3*150 ml). Combined organic layers were dried on anhydrous $Na_2SO_4$ and distilled to obtain a solid. Purification: Combi-Flash. Eluent: MeOH and DCM: 4:96. Appearance: Off-White solid. Yield: 4.7 g. % Yield: 60%. M.P.: 240-243° C. $^1$H-NMR (δ ppm, DMSO-$d_6$, 400 MHz): 12.61 (s, 1H), 8.26 (d, J 8, 1H), 8.00 (d, J 8, 1H), 7.90 (t, J 7.6, 1H), 7.83 (t, J 7.6, 1H), 7.49 (t, J 7.6, 1H), 7.41 (t, J 6.2, 2H), 7.35 (s, 1H), 7.26 (d, J 7.6, 1H), 7.18 (t, J 8, 1H), 7.08 (t, J 7.6, 1H), 6.60 (d, J 7.6, 1H), 6.09 (s, 1H), 4.40 (, 2H), 1.47 (s, 3H). MS (m/z): 398.27 ([M+H]$^+$).

Example 29

7-Fluoro-4-(4-fluoro-3-(3-hydroxy-3-methyl-2-oxoindolin-1-yl)benzyl)phthalazin-1(2H)-one Intermediate 51 (3 g, 7 mmol), hydrazine hydrate (500 mg, 9 mmol) and 2-Propanol (60 ml) were mixed and refluxed at 100° C. for 3 h. After 3 h, reaction mixture cooled to rt and stirred at rt for 1 h. Water (50 ml) was added to reaction mixture. Aqueous layer extracted with MeOH and DCM (1:9) (2*25 ml). Combined organic layers were dried on anhydrous $Na_2SO_4$ and distilled to obtain a solid. Purification: Combi-Flash. Eluent: MeOH and DCM: 3:97. Appearance: Pale-Brown solid. Yield: 1.3 g. % Yield: 40%. M.P.: 207-210° C. $^1$H-NMR (8 ppm, DMSO-$d_6$, 400 MHz):

12.72 (s, 1H), 8.16-8.09 (m, 1H), 7.94 (d, J 7.6, 1H), 7.81 (t, J 8, 1H), 7.51 (d, J 5.2, 1H), 7.44 (d, J 6.8, 2H), 7.39 (d, J 6.4, 1H), 7.22 (t, J 7.6, 1H), 7.11 (t, J 7.2, 1H), 6.50 (d, J 5.6, 1H), 6.27 (s, 0.4 H), 6.15 (s, 0.6 H), 4.41 (s, 1.2 H), 4.38 (s, 0.8 H), 1.51 (s, 1.2 H), 1.47 (s, 1.8 H). MS (m/z): 434.26 ($[M+H]^+$).

Example 30

4-((5-(3-methoxy-3-methyl-2-oxoindolin-1-yl)pyridin-3-yl)methyl)phthalazin-1(2H)-one Intermediate 52 (1.25 g, 3 mmol) was suspended in MeOH (5 ml) and cooled to 0° C. To this mixture sodium methoxide (972 mg, 4.5 mmol) was added. Reaction mixture warmed to rt and stirred at rt for 2 h. After 2 h, reaction mixture quenched with water (250 ml) and extracted the aqueous layer with DCM and MeOH (9:1) (2*50 ml) mixture. Combined organic layers were washed with water (50 ml) and 5% aqueous citric acid solution (50 ml). Organic layer dried on anhydrous $Na_2SO_4$ and distilled under vacuum to obtain crude. Crude was purified by column chromatography using EtOAc as eluent to obtain the titled compound as a white solid. Yield: 65 mg. % Yield: 5.3%. M.P.: 207-210° C. $^1$H-NMR (δ ppm, DMSO-$d_6$, 400 MHz): 12.59 (s, 1H), 8.65 (s, 1H), 8.57 (d, J 2, 1H), 8.28 (d, J 8, 1H), 8.08 (d, J 7.6, 1H), 7.95 (t, J 7.6, 1H), 7.90 (s, 1H), 7.86 (t, J 7.6, 1H), 7.45 (d, J 7.6, 1H), 7.31 (t, J 7.6, 1H), 7.19 (t, J 7.6, 1H), 6.75 (d, J 7.6, 1H) 4.47 (s, 2H), 2.97 (s, 3H), 1.54 (s, 3H). MS (m/z): 413.34 ($[M+H]^+$).

Example 31

4-(3-(3-Hydroxy-3-methyl-2-oxo-2,3-dihydro-1H-pyrrolo[2,3-c]pyridin-1-yl)benzyl)phthalazin-1(2H)-one Intermediate 58 (210 mg, 0.55 mmol), hydrazine hydrate (35 mg, 0.7 mmol) and 2-Propanol (5.2 ml) were mixed and refluxed at 100° C. for 3 h. After 3 h, reaction mixture cooled to rt and stirred at rt for 1 h. Water (50 ml) was added to reaction mixture. Aqueous layer extracted with MeOH and DCM (1:9) (2*50 ml). Combined organic layers were dried on anhydrous $Na_2SO_4$ and distilled to obtain a solid. Purification: Combi-Flash. Eluent: MeOH and DCM: 5:95. Appearance: Pale-Yellow solid. Yield: 30 mg. % Yield: 14%. M.P.: 133-136° C. $^1$H-NMR (δ ppm, DMSO-$d_6$, 400 MHz): 12.60 (s, 1H), 8.39 (d, J 4.4, 1H), 8.27 (dd, J 8, 1.2, 1H), 8.02 (d, J 8, 1H), 7.99 (s, 1H), 7.90 (td, J 8, 1.2, 1H), 7.83 (td, J 8, 1.2, 1H), 7.53-7.48 (m, 2H), 7.47-7.40 (m, 2H), 7.32 (d, J 8, 1H), 6.34 (s, 1H), 4.41 (s, 2H), 1.50 (s, 3H). MS (m/z): 399.40 ($[M+H]^+$).

Example 32

3-Methyl-2-oxo-1-(5-((4-oxo-3,4-dihydrophthalazin-1-yl)methyl)pyridin-3-yl)indolin-3-yl acetate Intermediate 52 (5 g, 12 mmol) was dissolved in DMF (60 ml), 18-Crown-6 (3.17 g, 12 mmol) and Cesium acetate (9.21 g, 48 mmol) were added. This mixture was stirred at 80° C. for 1.5 h. After completion of the reaction, reaction mixture diluted with water and extracted with DCM (3*100 ml). Combined organic layers were distilled to obtain a crude. Purification: Column chromatography on 60-120 mesh silica gel. Eluent: MeOH and DCM: 4:96. Appearance: Off-White solid. Yield: 1.2 g. % Yield: 22.7%. M.P.: 237-239° C. $^1$H-NMR (8 ppm, DMSO-$d_6$, 400 MHz): 12.58 (s, 1H), 8.67 (s, 1H), 8.49 (d, J 2, 1H), 8.27 (d, J 8, 1H), 8.07 (d, J 8, 1H), 7.94 (t, J 7.2, 1H), 7.85 (t, J 8, 1H), 7.79 (s, 1H), 7.43 (d, J 7.6, 1H), 7.26 (t, J 7.6, 1H), 7.12 (t, J 7.6, 1H), 6.69 (d, J 7.6, 1H), 4.48 (s, 2H), 2.03 (s, 3H), 1.63 (s, 3H). MS (m/z): 441.3 ($[M+H]^+$).

Example 33

4-(4-Fluoro-3-(2-oxoindolin-1-yl)benzyl)phthalazin-1(2H)-one

Following the general procedure 3, the titled compound was synthesized from Intermediate 65 (200 mg, 0.54 mmol), hydrazine hydrate (32 mg, 0.65 mmol) and acetic acid (16 mg, 0.27 mmol). Purification: Combi-Flash. Eluent: MeOH and DCM: 2.7:97.3. Appearance: Off-White solid. Yield: 12 mg. % Yield: 5.8%. M.P.: 232-235° C. $^1$H-NMR (8 ppm, DMSO-$d_6$, 400 MHz): 12.59 (s, 1H), 8.25 (d, J 7.8, 1H), 7.99 (d, J 7.8, 1H), 7.94-7.88 (m, 1H), 7.87-7.80 (m, 1H), 7.50-7.37 (m, 3H), 7.32 (d, J 7.2, 1H), 7.14 (t, J 7.6, 1H), 7.06 (t, J 7.2, 1H), 6.44 (d, J 7.6, 1H), 4.37 (s, 2H), 3.76 (d, J 5, 2H). MS (m/z): 386.0 ($[M+H]^+$).

Example 34

4-(3-(3,3-Dimethyl-2-oxoindolin-1-yl)-4-fluorobenzyl)phthalazine-1(2H)-one

Following the general procedure 3, the titled compound was synthesized from Intermediate 71 (600 mg, 1.5 mmol), hydrazine hydrate (90 mg, 1.8 mmol) and acetic acid (45 mg, 0.75 mmol). Purification: Combi-Flash. Eluent: MeOH and DCM: 2:98. Appearance: Off-White solid. Yield: 340 mg. % Yield: 54%. M.P.: 129-132° C. $^1$H-NMR (δ ppm, DMSO-$d_6$, 400 MHz): 12.59 (s, 1H), 8.25 (d, J 7.7, 1H), 8.00 (d, J 7.8, 1H), 7.90 (t, J 7, 1H), 7.87-7.80 (m, 1H), 7.52 (d, J 6.2, 1H), 7.48-7.35 (m, 3H), 7.15 (t, J 7.5, 1H), 7.09 (t, J 7.2, 1H), 6.48 (d, J 7.7, 1H), 4.37 (s, 2H), 1.38 (s, 3H), 1.35 (s, 3H). MS (m/z): 414.45 ([M+H]

Example 35

4-((5-(3,3-Dimethyl-2-oxoindolin-1-yl)pyridin-3-yl)methyl)phthalazin-1(2H)-one

Following the general procedure 3, the titled compound was synthesized from Intermediate 74 (600 mg, 1.57 mmol), hydrazine hydrate (94 mg, 1.88 mmol) and acetic acid (47 mg, 0.78 mmol). Purification: Combi-Flash. Eluent: MeOH and DCM: 3:97. Appearance: Off-White solid. Yield: 260 mg. % Yield: 41%. M.P.: 221-224° C. $^1$H-NMR (δ ppm, DMSO-$d_6$, 400 MHz): 12.58 (s, 1H), 8.63 (s, 1H), 8.54 (s, 1H), 8.26 (d, J 7.8, 1H), 8.06 (d, J 7.8, 1H), 7.93 (t, J 7.8, 1H), 7.88-7.80 (m, 2H), 7.43 (d, J 7.2, 1H), 7.18 (t, J 7.6, 1H), 7.10 (t, J 7.3, 1H), 6.70 (d, J 7.7, 1H), 4.45 (s, 2H), 1.37 (s, 6H). MS (m/z): 397.47 ($[M+H]^+$).

Example 36

4-((5-(3,3-Dimethyl-2-oxo-2,3-dihydro-1H-pyrrolo[3,2-b]pyridin-1-yl)pyridin-3-yl)methyl)phthalazin-1(2H)-one Following the general procedure 3, the titled compound was synthesized from Intermediate 81 (762 mg, 1.99 mmol), hydrazine hydrate (119 mg, 2.38 mmol) and acetic acid (59 mg, 0.99 mmol). Purification: Combi-Flash. Eluent: MeOH and DCM: 5.2:94.8. Appearance: Off-White solid. Yield: 300 mg. % Yield: 38%. M.P.: 242-245° C. $^1$H-NMR (8 ppm, DMSO-$d_6$, 400 MHz): 12.58 (s, 1H), 8.64 (s, 1H), 8.58 (s, 1H), 8.26 (d, J 7.8, 1H), 8.22 (d, J 4.6, 1H), 8.05 (d, J 8, 1H), 7.93 (t, J 7.6, 1H), 7.89 (s, 1H), 7.84 (t, J 7.4, 1H), 7.24-7.18 (m, 1H), 7.12 (d, J 7.8, 1H), 4.45 (s, 2H), 1.38 (s, 6H). MS (m/z): 398.1 ($[M+H]^+$).

Example 37

4-(3-(3,3-Dimethyl-2-oxo-2,3-dihydro-1H-pyrrolo[3,2-b]pyridin-1-yl)-4-fluorobenzyl)phthalazin-1(2H)-one Following the general procedure 3, the titled compound was synthesized from Intermediate 84 (390 mg, 0.97 mmol), hydrazine hydrate (49 mg, 1.17 mmol) and acetic acid (29 mg, 0.49 mmol). Purification: Combi-Flash. Eluent: MeOH and DCM: 3.2:96.8. Appearance: Off-White solid. Yield: 168 mg. % Yield: 42%. M.P.: 114-117° C. $^1$H-NMR (8 ppm, DMSO-$d_6$, 400 MHz): 12.59 (S, 1H), 8.25 (d, J 7.8, 1H), 8.23-8.21 (m, 1H), 7.99 (d, J 8, 1H), 7.90 (t, J 7, 1H), 7.85-7.81 (m, 1H), 7.60-7.53 (m, 1H), 7.50-7.45 (m, 1H), 7.44-7.38 (m, 1H), 7.20 (dd, J 8, 5.04, 1H), 6.91 (d, J 7.9, 1H), 4.37 (s, 2H), 1.40 (s, 3H), 1.36 (s, 3H) MS (m/z): 415.2 ($[M+H]^+$).

Example 38

1'-(5-((4-Oxo-3,4-dihydrophthalazin-1-yl)methyl)pyridin-3-yl)spiro[cyclopropane-1,3'-indolin]-2'-one Following the general procedure 3, the titled compound was synthesized from Intermediate 89 (591 mg, 1.55 mmol), hydrazine hydrate (93 mg, 1.86 mmol) and acetic acid (46 mg, 0.78 mmol). Purification: Combi-Flash. Eluent: MeOH and DCM: 3.1:96.9. Appearance: Pale-Yellow solid. Yield: 160 mg. % Yield: 26%. M.P.: 219-222° C. $^1$H-NMR (8 ppm, DMSO-$d_6$, 400 MHz): 12.57 (s, 1H), 8.63 (d, J 1.7, 1H), 8.57 (d, J 2.3, 1H), 8.26 (d, J 7.8, 1H), 8.07 (d, J 8, 1H), 7.93 (t, J 7, 1H), 7.90-7.81 (m, 2H), 7.20-7.16 (m, 1H), 7.12-7.04 (m, 2H), 6.79 (d, J 7.8, 1H), 4.46 (s, 2H), 1.76-1.70 (m, 2H), 1.65-1.60 (m, 2H). MS (m/z): 395.35 ($[M+H]^+$).

BIOLOGICAL ASSAYS

The pharmacological properties of the compounds of the invention may be confirmed by a number of pharmacological assays. Suitable pharmacological assays which may be been carried out to assess the compounds described herein are given below.

Example-1

Cell Proliferation Assay to Determine $GI_{50}$ for Compounds of Formula (I) in HCT-116 and UWB 1.289 Cell Lines (MTT Assay)

Assay Protocol

On Day "0" the test cells were plated in 100 μL/well in complete media in a 96-well plate in triplicate and the plates were incubated at 37° C. and 5% $CO_2$. On Day 1, 10 μL of MTT (5 mg/ml) was added to the column designated for Day "0". The column was mixed well and incubated at 37° C. and 5% $CO_2$ for 3.5 hours. Cells were pelleted down at 4000 rpm for 10 minutes. Media was aspirated out and 150 μL of DMSO was added to the cells and mixed by pipetting to dissolve the crystals. The plate was read at A560 nm and A640 nm. DMSO dilutions of the inhibitors were diluted to 3× of the required concentration in growth medium. Cells in each well were treated with 50 μL of complete media containing inhibitor. DMSO concentration in the well was 0.1%. Plates were incubated at 37° C. and 5% $CO_2$ as required for 144 hours. 15 μL of MTT (5 mg/mL) was added to the wells. Plates were incubated at 37° C. and 5% $CO_2$ for 3.5 hours. After incubation, cells are pelleted down at 4000 rpm for 10 min. Media was aspirated and 150 μL of DMSO per well were added to dissolve the formazan crystals. Plate was read at A560 nm and A640 nm. Results: $GI_{50}$ values were determined for the compounds of the invention. $GI_{50}$ values are given below in Table-2:

Example 2

PARP Enzyme Assay for Determination of $IC_{50}$ of Compounds of Formula (1)

Assay Protocol:

Step 1-Coating:

1) Coat 25 μL of histone solution onto a 384-well plate as described below:
   - Dilute 5x histone mixture 1:5 with PBS.
   - Add 25 μL of diluted histone solution to each well and incubate at 4° C. overnight.
   - Wash the plate three times using 100 μL PBST buffer (1×PBS containing 0.05% Tween20) per well.
   - Tap plate onto clean paper towel to remove liquid.
   - Block the wells by adding 100 μL of Blocking buffer 3 to every well. Incubate at room temperature for 1 h 15 minutes.
   - Wash plate three times with 100 μL PBST buffer as described above.
   - Tap plate onto clean paper towel to remove liquid.

Step 2: Ribosylation Reaction:

1) Preparation of 1×PARP Buffer:
   - Prepare 1× PARP buffer by adding 1 part of 10× PARP buffer to 9 parts distilled water (v/v). To prepare 500 μL of 1×PARP buffer, add 50 μL 10×PARP Assay buffer to 450 μL of $H_2O$ and mix well.
2) Preparation of the Ribosylation master mixture:
   - N wells x (1.25 μL 10× PARP buffer+1.25 μL 10×PARP Assay mixture+2.5 μL Activated DNA+7.5 μL distilled water). Add 12.5 μL to every well.
3) Preparation of the inhibitor solution:
   - 10 mM stock solution of the inhibitor was prepared in DMSO. From 10 mM stock solution, 250× concentrations of the inhibitor were made in DMSO.
   - 250×DMSO concentrations of the inhibitor were further diluted to 10× concentrations in 1× kinase buffer.
   - 2.5 μL (10× concentrations) of kinase buffer containing inhibitor was added to each well.
   - For the "Positive Control" and "Blank", add 2.5 μL of kinase buffer containing DMSO (4%) was added.
   - The final DMSO concentration in the well was 0.4%.
4) Preparation of the enzyme solution:
   - Thaw PARP1 enzyme on ice. Upon first thaw, briefly spin tube containing enzyme to recover full content of the tube. Calculate the amount of PARP1 required for the assay and dilute enzyme to 2.0 ng/uL with 1× PARP buffer.

Initiate reaction by adding 10 μL of diluted PARP1 enzyme to the wells designated "Positive Control" and "Test Inhibitor".

To the wells designated as "Blank", add 10 μL of 1×PARP buffer.

Centrifuge the plate at 1000 rpm for 30 seconds and incubate at room temperature for 60 min.

Discard the reaction mixture after 1 hour, and wash plate three times with 100 μL PBST buffer and tap plate onto clean paper towel as described above.

Step 3: Detection:

1) Preparation of Streptavidin-HRP:

Dilute Streptavidin-HRP 1:50 in Blocking buffer.

Add 25 μL of diluted Streptavidin-HRP to each well. Incubate for 30 min. at room temperature.

Wash three times with 100 μL PBST buffer and tap plate onto clean paper towel as above as described above.

2) Preparation of ECL substrate:

Just before use, mix on ice equal amounts of ELISA ECL Substrate A and ELISA ECL Substrate B and add 50 μL per well.

Immediately read the plate in microtiter-plate in Chemiluminescence setting. The "Blank" value is subtracted from all other values.

Results: % inhibitions values and $IC_{50}$ values are given below in Table-2:

Example-3

UWB 1.289 cells were plated at a predetermined density in a 6-well plate in its respective media and plates were incubated at 37° C. and 5% $CO_2$ overnight. After overnight incubation, the plates were treated with desired concentrations of the compound or DMSO and the plates were incubated at 37° C. and 5% $CO_2$ as required for 24 hours.

After completion of 24 hours incubation, total cell lysates were prepared from the treated samples.

Lysates were analysed by western-blot analysis and probed with Human PAR specific monoclonal antibody or human specific beta-actin monoclonal antibody (loading control).

Western-blot images were developed after exposing them to chemiluminescent substrate and images were captured on imaging system.

Target specific bands and loading specific bands were measured using densitometric analysis. Densitometric values of target specific bands were normalized to loading control values. % inhibition of PAR was calculated relative to DMSO treated samples.

Results: % inhibitions values are given below in Table-2:

TABLE 2

| | % inhibition | | $IC_{50}$ (nM) | | PAR % inhibition in UWB 1.289 | | |
|---|---|---|---|---|---|---|---|
| Ex. No. | 10 nM | 100 nM | IC50 (nM)-PARP1 | IC50 (nM)-PARP2 | HCT−116 | UWB 1.289 | @ 10 nM |
| 1 | A | A | + | + | E1 | A1 | B |
| 2 | – | – | + | + | B1 | A1 | A |
| 3 | – | – | + | + | E1 | E1 | D |
| 4 | A | A | – | – | – | – | – |
| 5 | A | A | – | – | – | – | – |
| 6 | A | A | + | + | E1 | B1 | – |
| 7 | – | – | + | + | A1 | A1 | A |
| 8 | – | – | + | + | C1 | E1 | C |
| 9 | A | A | – | – | – | – | – |
| 10 | A | A | + | – | C1 | B1 | – |
| 11 | A | A | + | + | A1 | A1 | A |
| 12 | A | A | + | + | E1 | E1 | D |
| 13 | A | A | + | + | B1 | A1 | |
| 14 | B | A | + | + | B1 | A1 | A |
| 15 | A | A | + | + | E1 | E1 | D |
| 16 | A | A | – | – | – | – | – |
| 17 | A | A | – | – | – | – | – |
| 18 | A | A | + | + | C1 | B1 | |
| 19 | A | A | + | + | D1 | B1 | |
| 20 | A | A | + | + | B1 | A1 | B |
| 21 | – | – | + | ++ | E1 | D 1 | C |
| 22 | – | – | + | + | D | B1 | C |
| 23 | – | – | + | + | E1 | E1 | D |
| 24 | – | – | + | + | C1 | B1 | C |
| 25 | A | A | + | + | E1 | B1 | C |
| 26 | A | A | | | | | |
| 27 | C | C | | | | | |
| 28 | A | A | – | – | – | – | – |
| 29 | A | A | – | | – | – | – |
| 30 | C | A | – | – | – | – | – |
| 31 | C | A | – | – | – | – | – |
| 32 | A | A | – | – | – | – | – |
| 33 | A | A | – | – | – | – | – |
| 34 | A | A | – | – | – | – | – |
| 35 | A | A | – | – | – | – | – |
| 36 | C | A | – | – | – | – | – |
| 37 | C | A | – | – | – | – | – |
| 38 | A | A | – | – | – | – | – |

% inhibition:
A represents >75% to 100%;
B represents >50% to ≤75%;
C represents >25% to ≤50% and
D represents ≤25% and
IC50:
+ represents ≤10 nM and
++ represents ≥10 nM: and
GI50:
A1 represents ≤2500 nM:
B1 represents >2500 nM to ≤5000 nM;
C1 represents >5000 nM to ≤7500 nM:
D1 represents >7500 nM to ≤10000 nM and
E1 represents >10000 nM Although the invention herein has been described with reference to particular embodiments, it is to be understood that these embodiments are merely illustrative of the principles and applications of the present invention. It is therefore to be understood that numerous modifications may be made to the illustrative embodiments and that other arrangements may be devised without departing from the spirit and scope of the present invention as described above. It is intended that the appended claims define the scope of the invention and that methods and structures within the scope of these claims and their equivalents be covered thereby.

All publications and patent and/or patent applications cited in this application are herein incorporated by reference to the same extent as if each individual publication or patent application was specifically and individually indicated to be incorporated herein by reference.

What is claimed is:

1. A compound of formula (I):

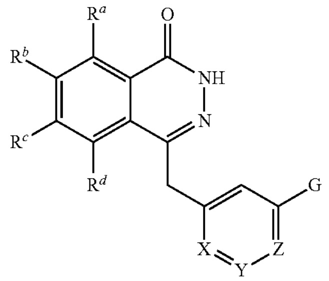

(I)

or a tautomer thereof, prodrug thereof, N-oxide thereof, stereoisomer thereof, pharmaceutically acceptable ester thereof or pharmaceutically acceptable salt thereof, wherein $R^a$ is hydrogen;

$R^b$ and $R^c$ are independently selected from hydrogen and fluorine;

$R^d$ is hydrogen;

X is $CR^x$;

Y is $CR^y$ or N;

Z is $CR^z$ or N;

$R^x$ and $R^y$ are hydrogen;

$R^z$ hydrogen or fluorine;

G is selected from (a)

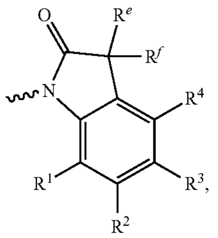

(b)

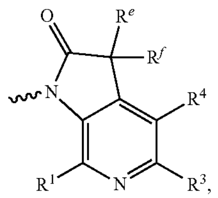

or (c)

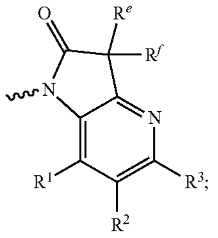

$R^e$ and $R^f$ are independently selected from hydrogen, substituted or unsubstituted alkyl, substituted or unsubstituted alkoxy, or —$OR^g$, or both $R^e$ and $R^f$ may be joined to form a $C_3$ cycloalkyl ring;

$R^g$ is selected from hydrogen, unsubstituted $C_1$ alkyl, or —(CO)$R^h$;

$R^h$ is unsubstituted alkyl; and $R^1$ is hydrogen;

$R^2$ and $R^3$ are independently selected from hydrogen, and fluorine; and $R^4$ is hydrogen.

2. The compound of claim 1, wherein $R^a$ is hydrogen;

$R^b$ and $R^c$ are independently selected from hydrogen and fluorine;

$R^d$ is hydrogen;

X is $CR^x$;

Y is $CR^y$ or N;

Z is CRZ or N;

$R^x$ and $R^y$ are hydrogen;

$R^z$ is hydrogen or fluorine;

G is selected from (a1)

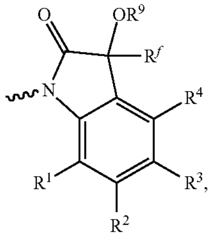

(b1)

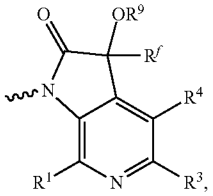

(c1)

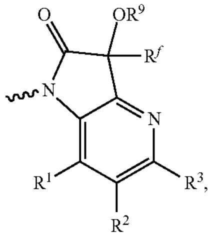

(a2)

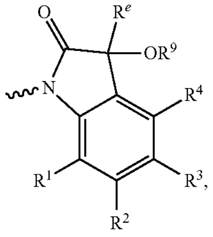

(b2)

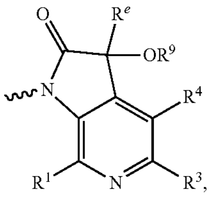

or

-continued (c2)

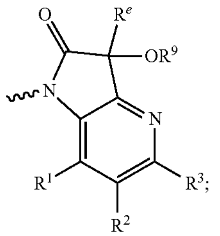

$R^e$ and $R^f$ are independently selected from hydrogen, substituted or unsubstituted alkyl, substituted or unsubstituted alkoxy, —$OR^g$, or both $R^e$ and $R^f$ may be joined to form an $C_3$ cycloalkyl ring;

$R^g$ is selected from hydrogen, unsubstituted $C_1$ alkyl, or —(CO)$R^h$;

$R^h$ is unsubstituted alkyl; and $R^1$ is hydrogen;

$R^2$ and $R^3$ are independently selected from hydrogen, and fluorine; and $R^4$ is hydrogen.

3. The compound of claim 1, wherein the compound is of the formula (IA) or (IB):

(IA)

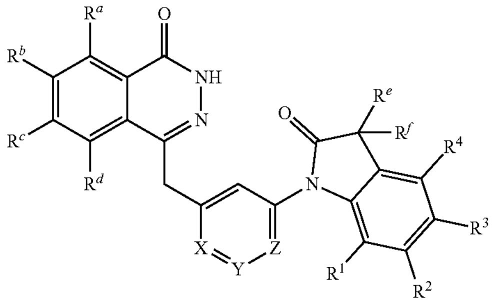

(IB)

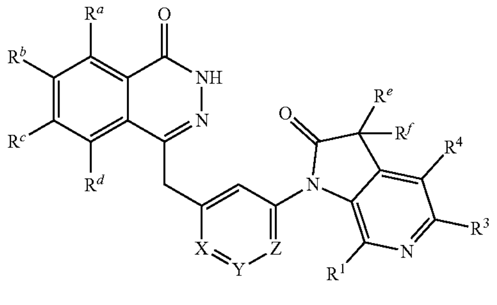

or a tautomer thereof, prodrug thereof, N-oxide thereof, stereoisomer thereof, pharmaceutically acceptable ester thereof or pharmaceutically acceptable salt thereof.

4. The compound of claim 1, wherein (i) $R^a$, $R^c$ and $R^d$ is hydrogen and $R^b$ is fluorine; or (ii) $R^a$, $R^b$ and $R^d$ is hydrogen and $R^c$ is fluorine.

5. The compound of claim 1, wherein X, Y and Z are independently selected from CH or N.

6. The compound of claim 5, wherein (i) X and Z is CH and Y is N; or (ii) X and Y is CH and Z is N.

7. The compound of claim 1, wherein X and Y is CH and Z is CRZ.

8. The compound of claim 1, wherein $R^z$ is fluorine.

9. The compound of claim 1, wherein $R^e$ and $R^f$ are independently selected from hydrogen, hydroxy, substituted or unsubstituted $C_{1-3}$ alkyl, substituted or unsubstituted $C_{1-3}$ alkoxy, and acetyloxy.

10. The compound of claim 9, wherein $R^e$ is hydroxy, substituted or unsubstituted $C_{1-3}$ alkoxy, or acetyloxy.

11. The compound of claim 10, wherein $R^e$ is hydroxy.

12. The compound of claim 9, wherein $R^f$ is substituted or unsubstituted $C_{1-3}$ alkyl.

13. The compound of claim 12, wherein $R^f$ is methyl, ethyl or $CF_3$.

14. The compound of claim 9, wherein $R^e$ is hydroxy and $R^f$ is substituted or unsubstituted $C_{1-3}$ alkyl.

15. The compound of claim 1, wherein (i) both $R^e$ and $R^f$ are hydrogen;

(ii) both $R^e$ and $R^f$ are independently selected from substituted or unsubstituted $C_{1-3}$ alkyl; or (iii) both $R^e$ and $R^f$ are joined to form a $[C_{3-6}]C_3$ cycloalkyl.

16. The compound of claim 15, wherein both $R^e$ and $R^f$ are hydrogen.

17. The compound of claim 15, wherein both $R^e$ and $R^f$ are methyl.

18. The compound of claim 1, wherein (i) $R^1$, $R^2$, $R^3$ and $R^4$ are hydrogen;

(ii) $R^1$, $R^3$ and $R^4$ are hydrogen and $R^2$ is halogen fluorine; or (iii) $R^1$, $R^2$ and $R^4$ are hydrogen and $R^3$ is halogen fluorine.

19. The compound of claim 1, wherein (i) $R^1$, $R^3$ and $R^4$ is hydrogen and $R^2$ is fluorine; or (ii) $R^1$, $R^2$ and $R^4$ is hydrogen and $R^3$ is fluorine.

20. The compound of claim 1, wherein G is selected from

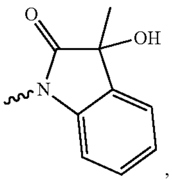 , 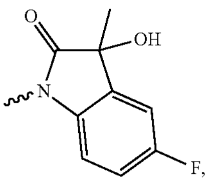 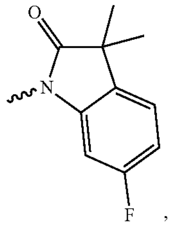 ,

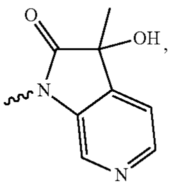 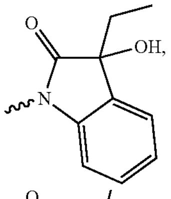 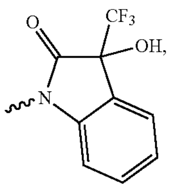

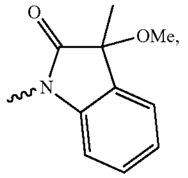 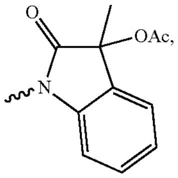 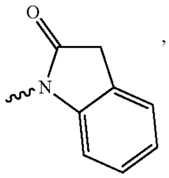 ,

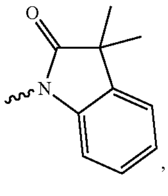 , 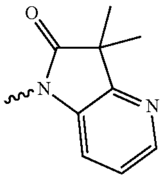 or

-continued

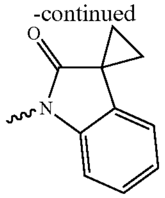

.

21. The compound of claim 20, wherein G is selected from

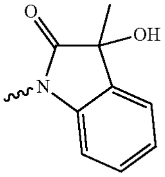,
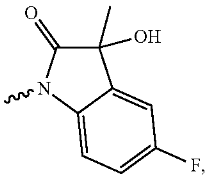,
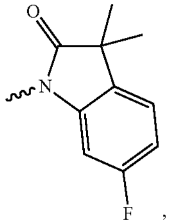,
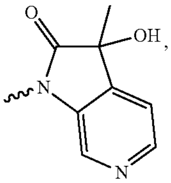,
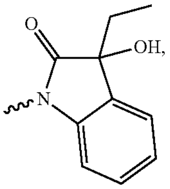,
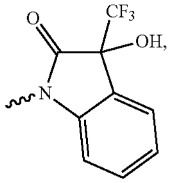,
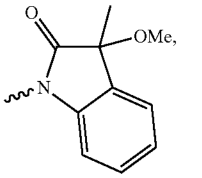, or
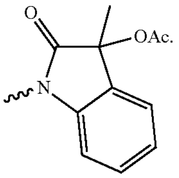.

22. A compound selected from:
4-((5-(3-Hydroxy-3-methyl-2-oxoindolin-1-yl)pyridin-3-yl)methyl)phthalazin-1(2H)-one;
(R)-(+)-4-((5-(3-Hydroxy-3-methyl-2-oxoindolin-1-yl)pyridin-3-yl)methyl)phthalazin-1(2H)-one;
(S)-(−)-4-((5-(3-Hydroxy-3-methyl-2-oxoindolin-1-yl)pyridin-3-yl)methyl)phthalazin-1(2H)-one;
4-(4-Fluoro-3-(3-hydroxy-3-methyl-2-oxoindolin-1-yl)benzyl)phthalazin-1(2H)-one;
4-((5-(3-Ethyl-3-hydroxy-2-oxoindolin-1-yl)pyridin-3-yl)methyl)phthalazin-1(2H)-one;
7-Fluoro-4-((5-(3-hydroxy-3-methyl-2-oxoindolin-1-yl)pyridin-3-yl)methyl)phthalazin-1(2H)-one;
(+)-7-Fluoro-4-((5-(3-hydroxy-3-methyl-2-oxoindolin-1-yl)pyridin-3-yl)methyl)phthalazin-1(2H)-one;
(−)-7-Fluoro-4-((5-(3-hydroxy-3-methyl-2-oxoindolin-1-yl)pyridin-3-yl)methyl)phthalazin-1(2H)-one;
6-Fluoro-4-((5-(3-hydroxy-3-methyl-2-oxoindolin-1-yl)pyridin-3-yl)methyl)phthalazin-1(2H)-one;
7-Fluoro-4-((5-(5-fluoro-3-hydroxy-3-methyl-2-oxoindolin-1-yl)pyridin-3-yl)methyl)phthalazin-1(2H)-one;
(+)-7-Fluoro-4-((5-(5-fluoro-3-hydroxy-3-methyl-2-oxoindolin-1-yl)pyridin-3-yl)methyl)phthalazin-1(2H)-one;

(−)-7-Fluoro-4-((5-(5-fluoro-3-hydroxy-3-methyl-2-oxoindolin-1-yl)pyridin-3-yl)methyl)phthalazin-1(2H)-one;
4-((5-(5-Fluoro-3-hydroxy-3-methyl-2-oxoindolin-1-yl)pyridin-3-yl)methyl)phthalazin-1(2H)-one;
(+)-4-((5-(5-Fluoro-3-hydroxy-3-methyl-2-oxoindolin-1-yl)pyridin-3-yl)methyl)phthalazin-1(2H)-one;
(−)-4-((5-(5-Fluoro-3-hydroxy-3-methyl-2-oxoindolin-1-yl)pyridin-3-yl)methyl)phthalazin-1(2H)-one;
7-Fluoro-4-((5-(6-fluoro-3-hydroxy-3-methyl-2-oxoindolin-1-yl)pyridin-3-yl)methyl)phthalazin-1(2H)-one;
7-Fluoro-4-((5-(6-fluoro-3-hydroxy-3-methyl-2-oxoindolin-1-yl)pyridin-3-yl)methyl)phthalazin-1(2H)-one;
4-((2-(3-hydroxy-3-methyl-2-oxoindolin-1-yl)pyridin-4-yl)methyl)phthalazin-1(2H)-one;
(−)-4-((2-(3-Hydroxy-3-methyl-2-oxoindolin-1-yl)pyridin-4-yl)methyl)phthalazin-1(2H)-one;
(+)-4-((2-(3-Hydroxy-3-methyl-2-oxoindolin-1-yl)pyridin-4-yl)methyl)phthalazin-1(2H)-one;
7-Fluoro-4-((2-(3-hydroxy-3-methyl-2-oxoindolin-1-yl)pyridin-4-yl)methyl)phthalazin-1(2H)-one;
(−)-7-Fluoro-4-((2-(3-hydroxy-3-methyl-2-oxoindolin-1-yl)pyridin-4-yl)methyl)phthalazin-1(2H)-one;
(+)-7-Fluoro-4-((2-(3-hydroxy-3-methyl-2-oxoindolin-1-yl)pyridin-4-yl)methyl)phthalazin-1(2H)-one;
7-Fluoro-4-((2-(5-fluoro-3-hydroxy-3-methyl-2-oxoindolin-1-yl)pyridin-4-yl)methyl)phthalazin-1(2H)-one;
4-((5-(3-Hydroxy-2-oxo-3-(trifluoromethyl)indolin-1-yl)pyridin-3-yl)methyl)phthalazin-1(2H)-one;
(+)-4-((5-(3-Hydroxy-2-oxo-3-(trifluoromethyl)indolin-1-yl)pyridin-3-yl)methyl)phthalazin-1(2H)-one;
(−)-4-((5-(3-Hydroxy-2-oxo-3-(trifluoromethyl)indolin-1-yl)pyridin-3-yl)methyl)phthalazin-1(2H)-one;
4-(3-(3-Hydroxy-3-methyl-2-oxoindolin-1-yl)benzyl)phthalazin-1(2H)-one;
7-Fluoro-4-(4-fluoro-3-(3-hydroxy-3-methyl-2-oxoindolin-1-yl)benzyl)phthalazin-1(2H)-one;
4-((5-(3-methoxy-3-methyl-2-oxoindolin-1-yl)pyridin-3-yl)methyl)phthalazin-1(2H)-one;
4-(3-(3-Hydroxy-3-methyl-2-oxo-2,3-dihydro-1H-pyrrolo[2,3-c]pyridin-1-yl)benzyl)phthalazin-1(2H)-one;
3-Methyl-2-oxo-1-(5-((4-oxo-3,4-dihydrophthalazin-1-yl)methyl)pyridin-3-yl)indolin-3-yl acetate;
4-(4-Fluoro-3-(2-oxoindolin-1-yl)benzyl)phthalazin-1(2H)-one;
4-(3-(3,3-Dimethyl-2-oxoindolin-1-yl)-4-fluorobenzyl)phthalazine-1(2H)-one;
4-((5-(3,3-Dimethyl-2-oxoindolin-1-yl)pyridin-3-yl)methyl)phthalazin-1(2H)-one;
4-((5-(3,3-Dimethyl-2-oxo-2,3-dihydro-1H-pyrrolo[3,2-b]pyridin-1-yl)pyridin-3-yl)methyl)phthalazin-1(2H)-one;
4-(3-(3,3-Dimethyl-2-oxo-2,3-dihydro-1H-pyrrolo[3,2-b]pyridin-1-yl)-4-fluorobenzyl)phthalazin-1(2H)-one; and
1'-(5-((4-Oxo-3,4-dihydrophthalazin-1-yl)methyl)pyridin-3-yl)spiro[cyclopropane-1,3'-indolin]-2'-one;
and pharmaceutically acceptable salts thereof.

23. A pharmaceutical composition comprising a compound of claim 1 and a pharmaceutically acceptable carrier.

24. The pharmaceutical composition of claim 23, further comprising one or more additional therapeutic agents.

25. The pharmaceutical composition of claim 24, wherein the one or more additional therapeutic agents is an anti-cancer agent, anti-inflammatory agent, immunosuppressive agent, steroid, non-steroidal anti-inflammatory agent, antihistamine, analgesic, or any combination of any of the foregoing.

26. The compound of claim 22, wherein the compound is 4-((5-(3-hydroxy-3-methyl-2-oxoindolin-1-yl)pyridin-3-yl)methyl)phthalazin-1(2H)-one or a pharmaceutically acceptable salt thereof.

27. The compound of claim 26, wherein the compound is (R)-(+)-4-((5-(3-hydroxy-3-methyl-2-oxoindolin-1-yl)pyridin-3-yl)methyl)phthalazin-1(2H)-one or a pharmaceutically acceptable salt thereof.

28. The compound of claim 26, wherein the compound is(S)-(−)-4-((5-(3-hydroxy-3-methyl-2-oxoindolin-1-yl)pyridin-3-yl)methyl)phthalazin-1(2H)-one or a pharmaceutically acceptable salt thereof.

* * * * *